US006936696B2

(12) United States Patent
Rapp et al.

(10) Patent No.: US 6,936,696 B2
(45) Date of Patent: Aug. 30, 2005

(54) ENHANCED PROTEINS AND METHODS FOR THEIR USE

(75) Inventors: William D. Rapp, St. Louis, MO (US); Jiexin Peng, St. Louis, MO (US); Gautham Nadig, Bangalore (IN); Tyamagondlu Venkatesh, St. Louis, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 10/245,227

(22) Filed: Sep. 17, 2002

(65) Prior Publication Data

US 2003/0200558 A1 Oct. 23, 2003

Related U.S. Application Data

(60) Provisional application No. 60/322,461, filed on Sep. 17, 2001.

(51) Int. Cl.[7] .................. A61K 35/78; A61K 35/80; C07K 14/00
(52) U.S. Cl. .................. 530/370; 530/377; 530/378; 514/8; 800/278; 800/294; 435/320.1; 435/91.1; 236/23.6
(58) Field of Search ................ 530/370, 377, 530/378; 514/8; 800/278, 294; 435/320.1, 91.1; 136/23.6

(56) References Cited

U.S. PATENT DOCUMENTS

| 5,003,045 A | 3/1991 | Hoffman |
| 5,487,991 A | 1/1996 | Vanderkerckhove et al. |
| 5,576,203 A | 11/1996 | Hoffman |
| 5,811,654 A | 9/1998 | Jaynes et al. |

FOREIGN PATENT DOCUMENTS

| WO | WO 95/27068 | 10/1995 |
| WO | WO 97/35023 | 9/1997 |
| WO | WO 98/13506 | 4/1998 |

OTHER PUBLICATIONS

Hoffman et al., *A Modified Storage Protein is Synthesized, Processed and Degraded in the Seeds of Transgenic Plants*, Plant Molecular Biology 11:717–729 (1988).

Jung et al.,*Site–specific Limited Proteolysis of Legumin Chloramphenicol Acetyl Transferase Fusions* In Vitro *and in Transgenic Tobacco Seeds*, J. Exper. Botany, 44:343–349 (Jan. 1993).

Utsumi et al., *Expression and Accumulation of Normal and Modified Soybean Glycinins in Potato Tubers*, Plant Science 102:181–188 (1994).

Utsumi et al., *Structure–Function Relationships of Soy Proteins*, In: "Food Proteins and Their Applications", Damodaran and Paraf, eds., Marcel ekker, NY, pp 257–291, (1997).

Utsumi et al., *Synthesis, Processing and Accumulation of Modified Glycinins of Soybean in the Seeds, Leaves and Stems of Transgenic Tobacco*; Plant Science, 92:191–202 (1993).

Utsumi, S., Plant Food Protein Entineering, In: "Advances in Food and Nutrition Research, vol. 36",Academic Press, Inc., pp. 89–208 (1992).

Harada et al., *Soybean β–Conglycinin Genes are Clustered in Several DNA Regions and are Regulated by Transcription and Posttranscriptional Processes*, The Plant Cell, 1:415–425 (Apr. 1989).

Maruyama et al., *The Roles of the N–Linked Glycans and Extension Regions of Soybean β–conglycinin in Folding, Assembly and Structural Features;* Eur. J. Biochem., 258:854–862 (1998).

Fukazawa, C., Database NCBI, Accession No. AB030841 (Sep. 2001). Internatioal Search Report, PCT/US02/30373, pp. 1–4 (Dec. 9, 2004).

*Primary Examiner*—Jon Weber
*Assistant Examiner*—Chih-Min Kam
(74) *Attorney, Agent, or Firm*—Renessen LLC

(57) ABSTRACT

The present invention generally relates to the field of plant genetics and protein biochemistry. More specifically, the present invention relates to modified proteins having an increased number of essential amino acids. The invention provides proteins modified to have an increased number of essential amino acids, nucleic acid sequences encoding the enhanced proteins, and methods of designing, producing, and using the same. The invention also includes compositions, transformed host cells, transgenic plants and seeds containing the enhanced proteins, and methods for preparing and using the same.

4 Claims, 3 Drawing Sheets

SEQUENCE LISTING

<160> NUMBER OF SEQ ID NOS: 97

<210> SEQ ID NO 1
<211> LENGTH: 439

```
<212> TYPE: PRT
<213> ORGANISM: Glycine max

<400> SEQUENCE: 1

Met Met Arg Val Arg Phe Pro Leu Leu Val Leu Leu Gly Thr Val Phe
1               5                   10                  15

Leu Ala Ser Val Cys Val Ser Leu Lys Val Arg Glu Asp Glu Asn Asn
            20                  25                  30

Pro Phe Tyr Leu Arg Ser Ser Asn Ser Phe Gln Thr Leu Phe Glu Asn
        35                  40                  45

Gln Asn Gly Arg Ile Arg Leu Leu Gln Arg Phe Asn Lys Arg Ser Pro
    50                  55                  60

Gln Leu Glu Asn Leu Arg Asp Tyr Arg Ile Val Gln Phe Gln Ser Lys
65                  70                  75                  80

Pro Asn Thr Ile Leu Leu Pro His His Ala Asp Ala Asp Phe Leu Leu
                85                  90                  95

Phe Val Leu Ser Gly Arg Ala Ile Leu Thr Leu Val Asn Asn Asp Asp
            100                 105                 110

Arg Asp Ser Tyr Asn Leu His Pro Gly Asp Ala Gln Arg Ile Pro Ala
        115                 120                 125

Gly Thr Thr Tyr Tyr Leu Val Asn Pro His Asp His Gln Asn Leu Lys
    130                 135                 140

Ile Ile Lys Leu Ala Ile Pro Val Asn Lys Pro Gly Arg Tyr Asp Asp
145                 150                 155                 160

Phe Phe Leu Ser Ser Thr Gln Ala Gln Gln Ser Tyr Leu Gln Gly Phe
                165                 170                 175

Ser His Asn Ile Leu Glu Thr Ser Phe His Ser Glu Phe Glu Glu Ile
            180                 185                 190

Asn Arg Val Leu Leu Gly Glu Glu Glu Gln Arg Gln Gln Glu Gly
        195                 200                 205

Val Ile Val Glu Leu Ser Lys Glu Gln Ile Arg Gln Leu Ser Arg Arg
    210                 215                 220

Ala Lys Ser Ser Arg Lys Thr Ile Ser Ser Glu Asp Glu Pro Phe
225                 230                 235                 240

Asn Leu Arg Ser Arg Asn Pro Ile Tyr Ser Asn Asn Phe Gly Lys Phe
                245                 250                 255

Phe Glu Ile Thr Pro Glu Lys Asn Pro Gln Leu Arg Asp Leu Asp Ile
            260                 265                 270

Phe Leu Ser Ser Val Asp Ile Asn Glu Gly Ala Leu Leu Leu Pro His
        275                 280                 285

Phe Asn Ser Lys Ala Ile Val Ile Leu Val Ile Asn Glu Gly Asp Ala
    290                 295                 300

Asn Ile Glu Leu Val Gly Ile Lys Glu Gln Gln Gln Lys Gln Lys Gln
305                 310                 315                 320

Glu Glu Glu Pro Leu Glu Val Gln Arg Tyr Arg Ala Glu Leu Ser Glu
                325                 330                 335

Asp Asp Val Phe Val Ile Pro Ala Ala Tyr Pro Phe Val Val Asn Ala
            340                 345                 350

Thr Ser Asn Leu Asn Phe Leu Ala Phe Gly Ile Asn Ala Glu Asn Asn
        355                 360                 365

Gln Arg Asn Phe Leu Ala Gly Glu Lys Asp Asn Val Val Arg Gln Ile
    370                 375                 380

Glu Arg Gln Val Gln Glu Leu Ala Phe Pro Gly Ser Ala Gln Asp Val
385                 390                 395                 400
```

Glu Arg Leu Leu Lys Lys Gln Arg Glu Ser Tyr Phe Val Asp Ala Gln
                405                 410                 415

Pro Gln Gln Lys Glu Glu Gly Ser Lys Gly Arg Lys Gly Pro Phe Pro
            420                 425                 430

Ser Ile Leu Gly Ala Leu Tyr
        435

<210> SEQ ID NO 2
<211> LENGTH: 390
<212> TYPE: PRT
<213> ORGANISM: Glycine max

<400> SEQUENCE: 2

Val Arg Glu Asp Glu Asn Asn Pro Phe Tyr Phe Arg Ser Ser Asn Ser
1               5                   10                  15

Phe Gln Thr Leu Phe Glu Asn Gln Asn Val Arg Ile Arg Leu Leu Gln
            20                  25                  30

Arg Phe Asn Lys Arg Ser Pro Gln Leu Glu Asn Leu Arg Asp Tyr Arg
        35                  40                  45

Ile Val Gln Phe Gln Ser Lys Pro Asn Thr Ile Leu Leu Pro His His
50                  55                  60

Ala Asp Ala Asp Phe Leu Leu Phe Val Leu Ser Gly Arg Ala Ile Leu
65                  70                  75                  80

Thr Leu Val Asn Asn Asp Asp Arg Asp Ser Tyr Asn Leu His Pro Gly
            85                  90                  95

Asp Ala Gln Arg Ile Pro Ala Gly Thr Thr Tyr Tyr Leu Val Asn Pro
        100                 105                 110

His Asp His Gln Asn Leu Lys Ile Ile Lys Leu Ala Ile Pro Val Asn
    115                 120                 125

Lys Pro Gly Arg Tyr Asp Asp Phe Phe Leu Ser Ser Thr Gln Ala Gln
130                 135                 140

Gln Ser Tyr Leu Gln Gly Phe Ser His Asn Ile Leu Glu Thr Ser Phe
145                 150                 155                 160

His Ser Glu Phe Glu Glu Ile Asn Arg Val Leu Phe Gly Glu Glu Glu
                165                 170                 175

Glu Gln Arg Gln Gln Glu Gly Val Ile Val Glu Leu Ser Lys Glu Gln
            180                 185                 190

Ile Arg Gln Leu Ser Arg Arg Ala Lys Ser Ser Ser Arg Lys Thr Ile
        195                 200                 205

Ser Ser Glu Asp Glu Pro Phe Asn Leu Arg Ser Arg Asn Pro Ile Tyr
210                 215                 220

Ser Asn Asn Phe Gly Lys Phe Glu Ile Thr Pro Glu Lys Asn Pro
225                 230                 235                 240

Gln Leu Arg Asp Leu Asp Ile Phe Leu Ser Ser Val Asp Ile Asn Glu
            245                 250                 255

Gly Ala Leu Leu Leu Pro His Phe Asn Ser Lys Ala Ile Val Ile Leu
        260                 265                 270

Val Ile Asn Glu Gly Asp Ala Asn Ile Glu Leu Val Gly Ile Lys Glu
    275                 280                 285

Gln Gln Gln Lys Gln Lys Gln Glu Glu Pro Leu Glu Val Gln Arg
290                 295                 300

Tyr Arg Ala Glu Leu Ser Glu Asp Asp Val Phe Val Ile Pro Ala Ala
305                 310                 315                 320

Tyr Pro Phe Val Val Asn Ala Thr Ser Asn Leu Asn Phe Leu Ala Phe

```
                    325                 330                 335
        Gly Ile Asn Ala Glu Asn Asn Gln Arg Asn Phe Leu Ala Gly Glu Lys
                340                 345                 350

Asp Asn Val Val Arg Gln Ile Glu Arg Gln Val Gln Glu Leu Ala Phe
                355                 360                 365

Pro Gly Ser Ala Gln Asp Val Glu Arg Leu Leu Lys Lys Gln Arg Glu
                370                 375                 380

Ser Tyr Phe Val Asp Ala
        385                 390

<210> SEQ ID NO 3
<211> LENGTH: 1320
<212> TYPE: DNA
<213> ORGANISM: Glycine max

<400> SEQUENCE: 3
atgatgagag tgcggtttcc tttgttggtg ttgctgggaa ctgttttcct ggcatcagtt      60
tgtgtctcat taaaggtgag agaggatgag aataacccct tctacttgag aagctctaac    120
agcttccaaa ctctctttga gaaccaaaac ggtcgcattc gtctcctcca gagattcaac    180
aaacgctccc cacaacttga gaaccttcga gactaccgga ttgtccagtt tcagtcaaaa    240
cccaacacaa tccttctccc ccaccatgct gacgccgatt tcctcctctt tgtccttagc    300
gggagagcca tacttacctt ggtgaacaac gacgacagag actcctacaa ccttcaccct    360
ggcgatgccc agagaatccc agctggaacc acttactatt tggttaaccc tcacgaccac    420
cagaatctca aaataatcaa acttgccata cccgtcaaca aacctggcag atatgatgat    480
ttcttcttat ctagcactca agcccaacag tcctacttgc aaggcttcag ccataatatt    540
ctagagacct ccttccatag cgaattcgag gagataaaca gggttttgtt gggagaggaa    600
gaggagcaga ggcagcaaga gggagtgatc gtggaactct caaggaaaca aattcggcaa    660
ctgagcagac gtgccaaatc tagttcaagg aaaaccattt cctccgaaga tgaaccattc    720
aacttgagaa gccgcaaccc catctattcc aacaactttg gaaagttctt tgagatcacc    780
cctgagaaaa ccccacagct tcgggacttg gatatcttcc tcagttctgt ggatatcaac    840
gaaggagctc ttcttctacc acacttcaat tcaaaggcca tagtgatact agtgattaat    900
gaaggagatg caaacattga acttgttggc attaaagaac aacaacagaa gcagaaacag    960
gaagaggaac ctttggaagt gcaaaggtac agagctgaat tgtctgaaga cgatgtattt   1020
gtaattccag cagcttatcc atttgtcgtc aacgctacct caaacctcaa tttccttgct   1080
tttggtatca atgctgagaa caaccagagg aacttccttg caggcgagaa agacaatgtg   1140
gtaaggcaga tagaaagaca agtgcaggag cttgcgttcc ctgggtctgc acaagatgtt   1200
gagaggctat taaagaagca gagggaatcc tactttgttg atgctcagcc tcagcagaag   1260
gaggagggga gtaaggaaag aaagggtcct tttccttcaa tcttaggtgc tctctactga   1320

<210> SEQ ID NO 4
<211> LENGTH: 20
<212> TYPE: DNA
<213> ORGANISM: Artificial
<220> FEATURE:
<223> OTHER INFORMATION: primer sequence

<400> SEQUENCE: 4
atactatgat gagagtgcgg                                                  20
```

```
<210> SEQ ID NO 5
<211> LENGTH: 20
<212> TYPE: DNA
<213> ORGANISM: Artificial
<220> FEATURE:
<223> OTHER INFORMATION: primer sequence

<400> SEQUENCE: 5
cactccatgt ttcatcgtcc                                                    20

<210> SEQ ID NO 6
<211> LENGTH: 20
<212> TYPE: DNA
<213> ORGANISM: Artificial
<220> FEATURE:
<223> OTHER INFORMATION: primer sequence

<400> SEQUENCE: 6
gttattcagt agagagcacc                                                    20

<210> SEQ ID NO 7
<211> LENGTH: 20
<212> TYPE: DNA
<213> ORGANISM: Artificial
<220> FEATURE:
<223> OTHER INFORMATION: primer sequence

<400> SEQUENCE: 7
tcacgatgag ctcttacagc                                                    20

<210> SEQ ID NO 8
<211> LENGTH: 24
<212> TYPE: DNA
<213> ORGANISM: Artificial
<220> FEATURE:
<223> OTHER INFORMATION: epitope sequence

<400> SEQUENCE: 8
gactacaagg acgacgatga caag                                               24

<210> SEQ ID NO 9
<211> LENGTH: 8
<212> TYPE: PRT
<213> ORGANISM: Artificial
<220> FEATURE:
<223> OTHER INFORMATION: epitope sequence

<400> SEQUENCE: 9

Asp Tyr Lys Asp Asp Asp Asp Lys
1               5

<210> SEQ ID NO 10
<211> LENGTH: 54
<212> TYPE: DNA
<213> ORGANISM: Artificial
<220> FEATURE:
<223> OTHER INFORMATION: primer sequence

<400> SEQUENCE: 10
atagccatgg actacaagga cgacgatgac aagttaaagg tgagagagga tgag              54

<210> SEQ ID NO 11
<211> LENGTH: 16
<212> TYPE: DNA
<213> ORGANISM: Artificial
<220> FEATURE:
<223> OTHER INFORMATION: primer sequence
```

-continued

<400> SEQUENCE: 11
gtaaaacgac ggccag    16

<210> SEQ ID NO 12
<211> LENGTH: 425
<212> TYPE: PRT
<213> ORGANISM: Artificial
<220> FEATURE:
<223> OTHER INFORMATION: epitope form of beta-conglycinin beta subunit

<400> SEQUENCE: 12

```
Met Asp Tyr Lys Asp Asp Asp Lys Leu Lys Val Arg Glu Asp Glu
1               5                   10                  15

Asn Asn Pro Phe Tyr Leu Arg Ser Ser Asn Ser Phe Gln Thr Leu Phe
            20                  25                  30

Glu Asn Gln Asn Gly Arg Ile Arg Leu Leu Gln Arg Phe Asn Lys Arg
        35                  40                  45

Ser Pro Gln Leu Glu Asn Leu Arg Asp Tyr Arg Ile Val Gln Phe Gln
    50                  55                  60

Ser Lys Pro Asn Thr Ile Leu Leu Pro His His Ala Asp Ala Asp Phe
65                  70                  75                  80

Leu Leu Phe Val Leu Ser Gly Arg Ala Ile Leu Thr Leu Val Asn Asn
                85                  90                  95

Asp Asp Arg Asp Ser Tyr Asn Leu His Pro Gly Asp Ala Gln Arg Ile
            100                 105                 110

Pro Ala Gly Thr Thr Tyr Tyr Leu Val Asn Pro His Asp His Gln Asn
        115                 120                 125

Leu Lys Ile Ile Lys Leu Ala Ile Pro Val Asn Lys Pro Gly Arg Tyr
    130                 135                 140

Asp Asp Phe Phe Leu Ser Ser Thr Gln Ala Gln Gln Ser Tyr Leu Gln
145                 150                 155                 160

Gly Phe Ser His Asn Ile Leu Glu Thr Ser Phe His Ser Glu Phe Glu
                165                 170                 175

Glu Ile Asn Arg Val Leu Leu Gly Glu Glu Glu Gln Arg Gln Gln
            180                 185                 190

Glu Gly Val Ile Val Glu Leu Ser Lys Glu Gln Ile Arg Gln Leu Ser
        195                 200                 205

Arg Arg Ala Lys Ser Ser Ser Arg Lys Thr Ile Ser Ser Glu Asp Glu
    210                 215                 220

Pro Phe Asn Leu Arg Ser Arg Asn Pro Ile Tyr Ser Asn Asn Phe Gly
225                 230                 235                 240

Lys Phe Phe Glu Ile Thr Pro Glu Lys Thr Pro Gln Leu Arg Asp Leu
                245                 250                 255

Asp Ile Phe Leu Ser Ser Val Asp Ile Asn Glu Gly Ala Leu Leu Leu
            260                 265                 270

Pro His Phe Asn Ser Lys Ala Ile Val Ile Leu Val Ile Asn Glu Gly
        275                 280                 285

Asp Ala Asn Ile Glu Leu Val Gly Ile Lys Glu Gln Gln Gln Lys Gln
    290                 295                 300

Lys Gln Glu Glu Glu Pro Leu Glu Val Gln Arg Tyr Arg Ala Glu Leu
305                 310                 315                 320

Ser Glu Asp Asp Val Phe Val Ile Pro Ala Ala Tyr Pro Phe Val Val
                325                 330                 335

Asn Ala Thr Ser Asn Leu Asn Phe Leu Ala Phe Gly Ile Asn Ala Glu
```

-continued

```
                   340              345              350
Asn Asn Gln Arg Asn Phe Leu Ala Gly Glu Lys Asp Asn Val Val Arg
            355              360              365
Gln Ile Glu Arg Gln Val Gln Glu Leu Ala Phe Pro Gly Ser Ala Gln
        370              375              380
Asp Val Glu Arg Leu Leu Lys Lys Gln Arg Glu Ser Tyr Phe Val Asp
385              390              395              400
Ala Gln Pro Gln Gln Lys Glu Glu Gly Ser Lys Gly Arg Lys Gly Pro
                405              410              415
Phe Pro Ser Ile Leu Gly Ala Leu Tyr
            420              425
```

<210> SEQ ID NO 13
<211> LENGTH: 1278
<212> TYPE: DNA
<213> ORGANISM: Artificial
<220> FEATURE:
<223> OTHER INFORMATION: epitope form of beta-conglycinin beta-subunit

<400> SEQUENCE: 13

```
atggactaca aggacgacga tgacaagtta aaggtgagag aggatgagaa taacccttc      60
tacttgagaa gctctaacag cttccaaact ctctttgaga accaaaacgg tcgcattcgt    120
ctcctccaga gattcaacaa cgctccccca caacttgaga accttcgaga ctaccggatt    180
gtccagtttc agtcaaaacc caacacaatc cttctcccc accatgctga cgccgatttc    240
ctcctctttg tccttagcgg gagagccata cttaccttgg tgaacaacga cgacagagac    300
tcctacaacc ttcaccctgg cgatgcccag agaatcccag ctggaaccac ttactatttg    360
gttaaccctc acgaccacca gaatctcaaa ataatcaaac ttgccatacc cgtcaacaaa    420
cctggcagat atgatgattt cttcttatct agcactcaag cccaacagtc ctacttgcaa    480
ggcttcagcc ataatattct agagacctcc ttccatagcg aattcgagga gataaacagg    540
gttttgttgg agaggaaga ggagcagagg cagcaagagg gagtgatcgt ggaactctca    600
aaggaacaaa ttcggcaact gagcagacgt gccaaatcta gttcaaggaa aaccattcc    660
tccgaagatg aaccattcaa cttgagaagc cgcaacccca tctattccaa caactttgga    720
aagttctttg agatcacccc tgagaaaaacc ccacagcttc gggacttgga tatcttcctc    780
agttctgtgg atatcaacga aggagctctt cttctaccac acttcaattc aaaggccata    840
gtgatactag tgattaatga aggagatgca aacattgaac ttgttggcat aaagaacaa    900
caacagaagc agaaacagga gaggaacct ttggaagtgc aaaggtacag agctgaattg    960
tctgaagacg atgtatttgt aattccagca gcttatccat ttgtcgtcaa cgctacctca   1020
aacctcaatt tccttgcttt tggtatcaat gctgagaaca accagaggaa cttccttgca   1080
ggcgagaaag acaatgtggt aaggcagata gaaagacaag tgcaggagct tgcgttccct   1140
gggtctgcac aagatgttga gaggctatta agaagcaga gggaatccta ctttgttgat   1200
gctcagcctc agcagaagga ggaggggagt aagggaagaa agggtccttt tccttcaatc   1260
ttaggtgctc tctactga                                                 1278
```

<210> SEQ ID NO 14
<211> LENGTH: 417
<212> TYPE: PRT
<213> ORGANISM: Artificial
<220> FEATURE:
<223> OTHER INFORMATION: mature form of beta-conglycinin beta-subunit

```
<400> SEQUENCE: 14

Met Leu Lys Val Arg Glu Asp Glu Asn Asn Pro Phe Tyr Leu Arg Ser
1               5                   10                  15

Ser Asn Ser Phe Gln Thr Leu Phe Glu Asn Gln Asn Gly Arg Ile Arg
            20                  25                  30

Leu Leu Gln Arg Phe Asn Lys Arg Ser Pro Gln Leu Glu Asn Leu Arg
        35                  40                  45

Asp Tyr Arg Ile Val Gln Phe Gln Ser Lys Pro Asn Thr Ile Leu Leu
    50                  55                  60

Pro His His Ala Asp Ala Asp Phe Leu Leu Phe Val Leu Ser Gly Arg
65                  70                  75                  80

Ala Ile Leu Thr Leu Val Asn Asn Asp Asp Arg Asp Ser Tyr Asn Leu
                85                  90                  95

His Pro Gly Asp Ala Gln Arg Ile Pro Ala Gly Thr Thr Tyr Tyr Leu
            100                 105                 110

Val Asn Pro His Asp His Gln Asn Leu Lys Ile Ile Lys Leu Ala Ile
        115                 120                 125

Pro Val Asn Lys Pro Gly Arg Tyr Asp Asp Phe Phe Leu Ser Ser Thr
    130                 135                 140

Gln Ala Gln Gln Ser Tyr Leu Gln Gly Phe Ser His Asn Ile Leu Glu
145                 150                 155                 160

Thr Ser Phe His Ser Glu Phe Glu Glu Ile Asn Arg Val Leu Leu Gly
                165                 170                 175

Glu Glu Glu Glu Gln Arg Gln Gln Glu Gly Val Ile Val Glu Leu Ser
            180                 185                 190

Lys Glu Gln Ile Arg Gln Leu Ser Arg Arg Ala Lys Ser Ser Ser Arg
        195                 200                 205

Lys Thr Ile Ser Ser Glu Asp Glu Pro Phe Asn Leu Arg Ser Arg Asn
    210                 215                 220

Pro Ile Tyr Ser Asn Asn Phe Gly Lys Phe Phe Glu Ile Thr Pro Glu
225                 230                 235                 240

Lys Thr Pro Gln Leu Arg Asp Leu Asp Ile Phe Leu Ser Ser Val Asp
                245                 250                 255

Ile Asn Glu Gly Ala Leu Leu Leu Pro His Phe Asn Ser Lys Ala Ile
            260                 265                 270

Val Ile Leu Val Ile Asn Glu Gly Asp Ala Asn Ile Glu Leu Val Gly
        275                 280                 285

Ile Lys Glu Gln Gln Gln Lys Gln Lys Gln Glu Glu Pro Leu Glu
    290                 295                 300

Val Gln Arg Tyr Arg Ala Glu Leu Ser Glu Asp Asp Val Phe Val Ile
305                 310                 315                 320

Pro Ala Ala Tyr Pro Phe Val Val Asn Ala Thr Ser Asn Leu Asn Phe
                325                 330                 335

Leu Ala Phe Gly Ile Asn Ala Glu Asn Asn Gln Arg Asn Phe Leu Ala
            340                 345                 350

Gly Glu Lys Asp Asn Val Val Arg Gln Ile Glu Arg Gln Val Gln Glu
        355                 360                 365

Leu Ala Phe Pro Gly Ser Ala Gln Asp Val Glu Arg Leu Leu Lys Lys
    370                 375                 380

Gln Arg Glu Ser Tyr Phe Val Asp Ala Gln Pro Gln Gln Lys Glu Glu
385                 390                 395                 400

Gly Ser Lys Gly Arg Lys Gly Pro Phe Pro Ser Ile Leu Gly Ala Leu
                405                 410                 415
```

Tyr

<210> SEQ ID NO 15
<211> LENGTH: 1254
<212> TYPE: DNA
<213> ORGANISM: Artificial
<220> FEATURE:
<223> OTHER INFORMATION: mature form of beta-conglycinin beta-subunit

<400> SEQUENCE: 15

| | | | | | |
|---|---|---|---|---|---|
| atgttaaagg | tgagagagga | tgagaataac | cctttctact | tgagaagctc | taacagcttc | 60 |
| caaactctct | ttgagaacca | aaacggtcgc | attcgtctcc | tccagagatt | caacaaacgc | 120 |
| tccccacaac | ttgagaacct | tcgagactac | cggattgtcc | agtttcagtc | aaaacccaac | 180 |
| acaatccttc | tcccccacca | tgctgacgcc | gatttcctcc | tctttgtcct | tagcgggaga | 240 |
| gccatactta | ccttggtgaa | caacgacgac | agagactcct | acaaccttca | ccctggcgat | 300 |
| gcccagagaa | tcccagctgg | aaccacttac | tatttggtta | accctcacga | ccaccagaat | 360 |
| ctcaaaataa | tcaaacttgc | catacccgtc | aacaaacctg | gcagatatga | tgatttcttc | 420 |
| ttatctagca | ctcaagccca | acagtcctac | ttgcaaggct | tcagccataa | tattctagag | 480 |
| acctccttcc | atagcgaatt | cgaggagata | acagggtttc | tgttgggaga | ggaagaggag | 540 |
| cagaggcagc | aagagggagt | gatcgtggaa | ctctcaaagg | aacaaattcg | gcaactgagc | 600 |
| agacgtgcca | aatctagttc | aaggaaaacc | atttcctccg | aagatgaacc | attcaacttg | 660 |
| agaagccgca | accccatcta | ttccaacaac | tttggaaagt | tctttgagat | caccccctgag | 720 |
| aaaaccccac | agcttcggga | cttggatatc | ttcctcagtt | ctgtggatat | caacgaagga | 780 |
| gctcttcttc | taccacactt | caattcaaag | gccatagtga | tactagtgat | taatgaagga | 840 |
| gatgcaaaca | ttgaacttgt | tggcattaaa | gaacaacaac | agaagcagaa | acaggaagag | 900 |
| gaacctttgg | aagtgcaaag | gtacagagct | gaattgtctg | aagacgatgt | atttgtaatt | 960 |
| ccagcagctt | atccatttgt | cgtcaacgct | acctcaaacc | tcaatttcct | tgcttttggt | 1020 |
| atcaatgctg | agaacaacca | gaggaacttc | cttgcaggcg | agaaagacaa | tgtggtaagg | 1080 |
| cagatagaaa | gacaagtgca | ggagcttgcg | ttccctgggt | ctgcacaaga | tgttgagagg | 1140 |
| ctattaaaga | agcagaggga | atcctacttt | gttgatgctc | agcctcagca | gaaggaggag | 1200 |
| gggagtaagg | gaagaaaggg | tccttttcct | tcaatcttag | gtgctctcta | ctga | 1254 |

<210> SEQ ID NO 16
<211> LENGTH: 34
<212> TYPE: DNA
<213> ORGANISM: Artificial
<220> FEATURE:
<223> OTHER INFORMATION: primer sequence

<400> SEQUENCE: 16
gaataaccct ttctggttta gaagctctaa cagc          34

<210> SEQ ID NO 17
<211> LENGTH: 32
<212> TYPE: DNA
<213> ORGANISM: Artificial
<220> FEATURE:
<223> OTHER INFORMATION: primer sequence

<400> SEQUENCE: 17
gaaccttcga gactggcgga ttgtccagtt tc            32

<210> SEQ ID NO 18
<211> LENGTH: 36
<212> TYPE: DNA
<213> ORGANISM: Artificial
<220> FEATURE:
<223> OTHER INFORMATION: primer sequence

<400> SEQUENCE: 18
acaatccttc tccctggca tgctgacgcc gatttc                        36

<210> SEQ ID NO 19
<211> LENGTH: 31
<212> TYPE: DNA
<213> ORGANISM: Artificial
<220> FEATURE:
<223> OTHER INFORMATION: primer sequence

<400> SEQUENCE: 19
acgacagaga ctcctggaac cttcaccctg g                            31

<210> SEQ ID NO 20
<211> LENGTH: 31
<212> TYPE: DNA
<213> ORGANISM: Artificial
<220> FEATURE:
<223> OTHER INFORMATION: primer sequence

<400> SEQUENCE: 20
cagctggaac cacttggtat ttggttaacc c                            31

<210> SEQ ID NO 21
<211> LENGTH: 28
<212> TYPE: DNA
<213> ORGANISM: Artificial
<220> FEATURE:
<223> OTHER INFORMATION: primer sequence

<400> SEQUENCE: 21
ggaaccactt actggttggt taaccctc                                28

<210> SEQ ID NO 22
<211> LENGTH: 34
<212> TYPE: DNA
<213> ORGANISM: Artificial
<220> FEATURE:
<223> OTHER INFORMATION: primer sequence

<400> SEQUENCE: 22
tactatttgg ttaactggca cgaccaccag aatc                         34

<210> SEQ ID NO 23
<211> LENGTH: 28
<212> TYPE: DNA
<213> ORGANISM: Artificial
<220> FEATURE:
<223> OTHER INFORMATION: primer sequence

<400> SEQUENCE: 23
caaacctggc agatgggatg atttcttc                                28

<210> SEQ ID NO 24
<211> LENGTH: 26
<212> TYPE: DNA
<213> ORGANISM: Artificial
<220> FEATURE:
<223> OTHER INFORMATION: primer sequence

<400> SEQUENCE: 24
cccaacagtc ctggttgcaa ggcttc					26

<210> SEQ ID NO 25
<211> LENGTH: 27
<212> TYPE: DNA
<213> ORGANISM: Artificial
<220> FEATURE:
<223> OTHER INFORMATION: primer sequence

<400> SEQUENCE: 25
ttgtttggag agtgggagga gcagagg					27

<210> SEQ ID NO 26
<211> LENGTH: 33
<212> TYPE: DNA
<213> ORGANISM: Artificial
<220> FEATURE:
<223> OTHER INFORMATION: primer sequence

<400> SEQUENCE: 26
tcctccgaag atgaatggtt caacttgaga agc					33

<210> SEQ ID NO 27
<211> LENGTH: 28
<212> TYPE: DNA
<213> ORGANISM: Artificial
<220> FEATURE:
<223> OTHER INFORMATION: primer sequence

<400> SEQUENCE: 27
gcaaccccat ctggtccaac aactttgg					28

<210> SEQ ID NO 28
<211> LENGTH: 33
<212> TYPE: DNA
<213> ORGANISM: Artificial
<220> FEATURE:
<223> OTHER INFORMATION: primer sequence

<400> SEQUENCE: 28
acccctgaga aaaactggca gcttcgggac ttg					33

<210> SEQ ID NO 29
<211> LENGTH: 33
<212> TYPE: DNA
<213> ORGANISM: Artificial
<220> FEATURE:
<223> OTHER INFORMATION: primer sequence

<400> SEQUENCE: 29
aaacaggaag aggaatggtt ggaagtgcaa agg					33

<210> SEQ ID NO 30
<211> LENGTH: 34
<212> TYPE: DNA
<213> ORGANISM: Artificial
<220> FEATURE:
<223> OTHER INFORMATION: primer sequence

<400> SEQUENCE: 30
ttggaagtgc aaaggtggag agctgaattg tctg					34

<210> SEQ ID NO 31

<211> LENGTH: 33
<212> TYPE: DNA
<213> ORGANISM: Artificial
<220> FEATURE:
<223> OTHER INFORMATION: primer sequence

<400> SEQUENCE: 31
gtaattccag cagcttggcc atttgtcgtc aac                    33

<210> SEQ ID NO 32
<211> LENGTH: 30
<212> TYPE: DNA
<213> ORGANISM: Artificial
<220> FEATURE:
<223> OTHER INFORMATION: primer sequence

<400> SEQUENCE: 32
ctgagcatca acaaaccagg attccctctg                       30

<210> SEQ ID NO 33
<211> LENGTH: 25
<212> TYPE: DNA
<213> ORGANISM: Artificial
<220> FEATURE:
<223> OTHER INFORMATION: primer sequence

<400> SEQUENCE: 33
ttgagaacca atggggtcgc attcg                            25

<210> SEQ ID NO 34
<211> LENGTH: 33
<212> TYPE: DNA
<213> ORGANISM: Artificial
<220> FEATURE:
<223> OTHER INFORMATION: primer sequence

<400> SEQUENCE: 34
gaggatgaga atattccttt ctacttgaga agc                   33

<210> SEQ ID NO 35
<211> LENGTH: 20
<212> TYPE: DNA
<213> ORGANISM: Artificial
<220> FEATURE:
<223> OTHER INFORMATION: primer sequence

<400> SEQUENCE: 35
cctttctaca ttagaagctc                                  20

<210> SEQ ID NO 36
<211> LENGTH: 23
<212> TYPE: DNA
<213> ORGANISM: Artificial
<220> FEATURE:
<223> OTHER INFORMATION: primer sequence

<400> SEQUENCE: 36
gagaaccaaa acattcgcat tcg                              23

<210> SEQ ID NO 37
<211> LENGTH: 27
<212> TYPE: DNA
<213> ORGANISM: Artificial
<220> FEATURE:
<223> OTHER INFORMATION: primer sequence

<400> SEQUENCE: 37
cgcattcgtc tcattcagag attcaac                                   27

<210> SEQ ID NO 38
<211> LENGTH: 19
<212> TYPE: DNA
<213> ORGANISM: Artificial
<220> FEATURE:
<223> OTHER INFORMATION: primer sequence

<400> SEQUENCE: 38
tccccacaaa ttgagaacc                                            19

<210> SEQ ID NO 39
<211> LENGTH: 32
<212> TYPE: DNA
<213> ORGANISM: Artificial
<220> FEATURE:
<223> OTHER INFORMATION: primer sequence

<400> SEQUENCE: 39
accttcgaga ctacattatt gtccagtttc ag                             32

<210> SEQ ID NO 40
<211> LENGTH: 36
<212> TYPE: DNA
<213> ORGANISM: Artificial
<220> FEATURE:
<223> OTHER INFORMATION: primer sequence

<400> SEQUENCE: 40
cgagactacc ggattattat tattcagtca aaaccc                         36

<210> SEQ ID NO 41
<211> LENGTH: 36
<212> TYPE: DNA
<213> ORGANISM: Artificial
<220> FEATURE:
<223> OTHER INFORMATION: primer sequence

<400> SEQUENCE: 41
cgagactaca ttattgtcat ttttcagtca aaaccc                         36

<210> SEQ ID NO 42
<211> LENGTH: 17
<212> TYPE: DNA
<213> ORGANISM: primer sequence

<400> SEQUENCE: 42
attgtccaga ttcagtc                                              17

<210> SEQ ID NO 43
<211> LENGTH: 19
<212> TYPE: DNA
<213> ORGANISM: Artificial
<220> FEATURE:
<223> OTHER INFORMATION: primer sequence

<400> SEQUENCE: 43
aacacaatca ttctcccccc                                           19

<210> SEQ ID NO 44
<211> LENGTH: 27
<212> TYPE: DNA
<213> ORGANISM: Artificial
<220> FEATURE:

<223> OTHER INFORMATION: primer sequence

<400> SEQUENCE: 44
atccttctcc ccattcatgc tgacgcc                27

<210> SEQ ID NO 45
<211> LENGTH: 22
<212> TYPE: DNA
<213> ORGANISM: Artificial
<220> FEATURE:
<223> OTHER INFORMATION: primer sequence

<400> SEQUENCE: 45
gacgccgatt tcattctctt tg                22

<210> SEQ ID NO 46
<211> LENGTH: 42
<212> TYPE: DNA
<213> ORGANISM: Artificial
<220> FEATURE:
<223> OTHER INFORMATION: primer sequence

<400> SEQUENCE: 46
gctgacgccg atttcattat tattattctt agcgggagag cc                42

<210> SEQ ID NO 47
<211> LENGTH: 24
<212> TYPE: DNA
<213> ORGANISM: Artificial
<220> FEATURE:
<223> OTHER INFORMATION: primer sequence

<400> SEQUENCE: 47
attattatta ttagcgggag agcc                24

<210> SEQ ID NO 48
<211> LENGTH: 30
<212> TYPE: DNA
<213> ORGANISM: Artificial
<220> FEATURE:
<223> OTHER INFORMATION: primer sequence

<400> SEQUENCE: 48
gtccttagcg ggattgccat acttaccttg                30

<210> SEQ ID NO 49
<211> LENGTH: 19
<212> TYPE: DNA
<213> ORGANISM: Artificial
<220> FEATURE:
<223> OTHER INFORMATION: primer sequence

<400> SEQUENCE: 49
agagccataa ttaccttgg                19

<210> SEQ ID NO 50
<211> LENGTH: 27
<212> TYPE: DNA
<213> ORGANISM: Artificial
<220> FEATURE:
<223> OTHER INFORMATION: primer sequence

<400> SEQUENCE: 50
gccataatta ccattgtgaa caacgac                27

<210> SEQ ID NO 51
<211> LENGTH: 27
<212> TYPE: DNA
<213> ORGANISM: Artificial
<220> FEATURE:
<223> OTHER INFORMATION: primer sequence

<400> SEQUENCE: 51
agagactcct acattcttca ccctggc                                27

<210> SEQ ID NO 52
<211> LENGTH: 20
<212> TYPE: DNA
<213> ORGANISM: Artificial
<220> FEATURE:
<223> OTHER INFORMATION: primer sequence

<400> SEQUENCE: 52
tcctacaaca ttcaccctgg                                        20

<210> SEQ ID NO 53
<211> LENGTH: 27
<212> TYPE: DNA
<213> ORGANISM: Artificial
<220> FEATURE:
<223> OTHER INFORMATION: primer sequence

<400> SEQUENCE: 53
cttcaccctg gcattgccca gagaatc                                27

<210> SEQ ID NO 54
<211> LENGTH: 28
<212> TYPE: DNA
<213> ORGANISM: Artificial
<220> FEATURE:
<223> OTHER INFORMATION: primer sequence

<400> SEQUENCE: 54
cctggcgatg ccattagaat cccagctg                               28

<210> SEQ ID NO 55
<211> LENGTH: 34
<212> TYPE: DNA
<213> ORGANISM: Artificial
<220> FEATURE:
<223> OTHER INFORMATION: primer sequence

<400> SEQUENCE: 55
tggaaccact tactatatta ttaaccctca cgac                        34

<210> SEQ ID NO 56
<211> LENGTH: 27
<212> TYPE: DNA
<213> ORGANISM: Artificial
<220> FEATURE:
<223> OTHER INFORMATION: primer sequence

<400> SEQUENCE: 56
tatttggtta acattcacga ccaccag                                27

<210> SEQ ID NO 57
<211> LENGTH: 26
<212> TYPE: DNA
<213> ORGANISM: Artificial
<220> FEATURE:
<223> OTHER INFORMATION: primer sequence

<400> SEQUENCE: 57
caaaataatc attcttgcca tacccg    26

<210> SEQ ID NO 58
<211> LENGTH: 22
<212> TYPE: DNA
<213> ORGANISM: Artificial
<220> FEATURE:
<223> OTHER INFORMATION: primer sequence

<400> SEQUENCE: 58
ataatcaaaa ttgccatacc cg    22

<210> SEQ ID NO 59
<211> LENGTH: 30
<212> TYPE: DNA
<213> ORGANISM: Artificial
<220> FEATURE:
<223> OTHER INFORMATION: primer sequence

<400> SEQUENCE: 59
aaacttgcca taattgtcaa caaacctggc    30

<210> SEQ ID NO 60
<211> LENGTH: 27
<212> TYPE: DNA
<213> ORGANISM: Artificial
<220> FEATURE:
<223> OTHER INFORMATION: primer sequence

<400> SEQUENCE: 60
cagcaagagg gaattatcgt ggaactc    27

<210> SEQ ID NO 61
<211> LENGTH: 30
<212> TYPE: DNA
<213> ORGANISM: Artificial
<220> FEATURE:
<223> OTHER INFORMATION: primer sequence

<400> SEQUENCE: 61
agaagccgca acattatctg gtccaacaac    30

<210> SEQ ID NO 62
<211> LENGTH: 29
<212> TYPE: DNA
<213> ORGANISM: Artificial
<220> FEATURE:
<223> OTHER INFORMATION: primer sequence

<400> SEQUENCE: 62
aactttggaa agatttttga gatcacccc    29

<210> SEQ ID NO 63
<211> LENGTH: 36
<212> TYPE: DNA
<213> ORGANISM: Artificial
<220> FEATURE:
<223> OTHER INFORMATION: primer sequence

<400> SEQUENCE: 63
atcacccctg agaaaattat tcagcttcgg gacttg    36

<210> SEQ ID NO 64
<211> LENGTH: 18

```
<212> TYPE: DNA
<213> ORGANISM: Artificial
<220> FEATURE:
<223> OTHER INFORMATION: primer sequence

<400> SEQUENCE: 64
aacccacaga ttcgggac                                            18

<210> SEQ ID NO 65
<211> LENGTH: 19
<212> TYPE: DNA
<213> ORGANISM: Artificial
<220> FEATURE:
<223> OTHER INFORMATION: primer sequence

<400> SEQUENCE: 65
ggagctctta ttctaccac                                           19

<210> SEQ ID NO 66
<211> LENGTH: 28
<212> TYPE: DNA
<213> ORGANISM: Artificial
<220> FEATURE:
<223> OTHER INFORMATION: pirmer sequence

<400> SEQUENCE: 66
cgaaggagct cttattattc cacacttc                                 28

<210> SEQ ID NO 67
<211> LENGTH: 21
<212> TYPE: DNA
<213> ORGANISM: Artificial
<220> FEATURE:
<223> OTHER INFORMATION: primer sequence

<400> SEQUENCE: 67
ccacacttca tttcaaaggc c                                        21

<210> SEQ ID NO 68
<211> LENGTH: 28
<212> TYPE: DNA
<213> ORGANISM: Artificial
<220> FEATURE:
<223> OTHER INFORMATION: primer sequence

<400> SEQUENCE: 68
gccatagtga taattgtgat taatgaag                                 28

<210> SEQ ID NO 69
<211> LENGTH: 40
<212> TYPE: DNA
<213> ORGANISM: Artificial
<220> FEATURE:
<223> OTHER INFORMATION: primer sequence

<400> SEQUENCE: 69
caaaggccat agtgataatt attattaatg aaggagatgc                    40

<210> SEQ ID NO 70
<211> LENGTH: 23
<212> TYPE: DNA
<213> ORGANISM: Artificial
<220> FEATURE:
<223> OTHER INFORMATION: primer sequence

<400> SEQUENCE: 70
```

-continued ctagtgatta ttgaaggaga tgc                                       23

<210> SEQ ID NO 71
<211> LENGTH: 21
<212> TYPE: DNA
<213> ORGANISM: Artificial
<220> FEATURE:
<223> OTHER INFORMATION: primer sequence

<400> SEQUENCE: 71
gcaaacattg aaattgttgg c                                         21

<210> SEQ ID NO 72
<211> LENGTH: 30
<212> TYPE: DNA
<213> ORGANISM: Artificial
<220> FEATURE:
<223> OTHER INFORMATION: primer sequence

<400> SEQUENCE: 72
acaggaagag gaaattttgg aagtgcaaag                                30

<210> SEQ ID NO 73
<211> LENGTH: 25
<212> TYPE: DNA
<213> ORGANISM: Artificial
<220> FEATURE:
<223> OTHER INFORMATION: primer sequence

<400> SEQUENCE: 73
tacagagctg aaatttctga agacg                                     25

<210> SEQ ID NO 74
<211> LENGTH: 32
<212> TYPE: DNA
<213> ORGANISM: Artificial
<220> FEATURE:
<223> OTHER INFORMATION: primer sequence

<400> SEQUENCE: 74
tctgaagacg atattttgt aattccagca gc                              32

<210> SEQ ID NO 75
<211> LENGTH: 32
<212> TYPE: DNA
<213> ORGANISM: Artificial
<220> FEATURE:
<223> OTHER INFORMATION: primer sequence

<400> SEQUENCE: 75
tctgaagacg atattattgt aattccagca gc                             32

<210> SEQ ID NO 76
<211> LENGTH: 21
<212> TYPE: DNA
<213> ORGANISM: Artificial
<220> FEATURE:
<223> OTHER INFORMATION: primer sequence

<400> SEQUENCE: 76
gcttatccaa ttgtcgtcaa c                                         21

<210> SEQ ID NO 77
<211> LENGTH: 26
<212> TYPE: DNA
<213> ORGANISM: Artificial

-continued

```
<220> FEATURE:
<223> OTHER INFORMATION: primer sequence

<400> SEQUENCE: 77
tatccatttg tcattaacgc tacctc                                        26

<210> SEQ ID NO 78
<211> LENGTH: 26
<212> TYPE: DNA
<213> ORGANISM: Artificial
<220> FEATURE:
<223> OTHER INFORMATION: primer sequence

<400> SEQUENCE: 78
gctacctcaa acattaattt ccttgc                                        26

<210> SEQ ID NO 79
<211> LENGTH: 20
<212> TYPE: DNA
<213> ORGANISM: Artificial
<220> FEATURE:
<223> OTHER INFORMATION: primer sequence

<400> SEQUENCE: 79
ctcaatttca ttgcttttgg                                               20

<210> SEQ ID NO 80
<211> LENGTH: 48
<212> TYPE: DNA
<213> ORGANISM: Artificial
<220> FEATURE:
<223> OTHER INFORMATION: primer sequence

<400> SEQUENCE: 80
gctacctcaa acctcaatat tattgctatt ggtatcaatg ctgagaac                48

<210> SEQ ID NO 81
<211> LENGTH: 28
<212> TYPE: DNA
<213> ORGANISM: Artificial
<220> FEATURE:
<223> OTHER INFORMATION: primer sequence

<400> SEQUENCE: 81
aatgctgaga acattcagag gaacttcc                                      28

<210> SEQ ID NO 82
<211> LENGTH: 20
<212> TYPE: DNA
<213> ORGANISM: Artificial
<220> FEATURE:
<223> OTHER INFORMATION: primer sequence

<400> SEQUENCE: 82
gaatcctaca ttgttgatgc                                               20

<210> SEQ ID NO 83
<211> LENGTH: 23
<212> TYPE: DNA
<213> ORGANISM: Artificial
<220> FEATURE:
<223> OTHER INFORMATION: primer sequence

<400> SEQUENCE: 83
tcctacttta ttgatgctca gcc                                           23
```

<210> SEQ ID NO 84
<211> LENGTH: 1350
<212> TYPE: DNA
<213> ORGANISM: Glycine max

<400> SEQUENCE: 84

```
atgatgagag tgcggtttcc tttgttggtg ttgctgggaa ctgttttcct ggcatcagtt      60
tgtgtctcat taaaggacta caaggacgac gatgacaagc ttaaggtgag agaggatgag     120
aataacccctt tctacttgag aagctctaac agcttccaaa ctctctttga aaccaaaaac    180
ggtcgcattc gtctcattca gagattcaac aaacgctccc acaacttga gaaccttcga      240
gactaccgga ttgtccagtt tcagtcaaaa cccaacacaa tcattctccc ccaccatgct     300
gacgccgatt tcattattat tattcttagc gggagagcca tacttacctt ggtgaacaac     360
gacgacagag actcctacaa cattcaccct ggcgatgccc agagaatccc agctggaacc     420
acttactata ttattaaccc tcacgaccac cagaatctca aaataatcaa aattgccata     480
cccgtcaaca aacctggcag atatgatgat ttcttcttat ctagcactca agcccaacag     540
tcctacttgc aaggcttcag ccataatatt ctagagacct ccttccatag cgaattcgag     600
gagataaaca gggttttgtt gggagaggaa gaggagcaga ggcagcaaga gggagtgatc     660
gtggaactct caaggaaca aattcggcaa ctgagcagca gtgccaaatc tagttcaagg      720
aaaaccattt cctccgaaga tgaaccattc aacttgagaa gccgcaaccc catctattcc     780
aacaactttg gaagttctt tgagatcacc cctgagaaaa acccacagct tcgggacttg      840
gatatcttcc tcagttctgt ggatatcaac gaaggagctc ttcttctacc acacttcaat     900
tcaaaggcca tagtgatact agtgattaat gaaggagatg caaacattga acttgttggc     960
attaaagaac aacaacagaa gcagaaacag gaagaggaac ctttggaagt gcaaaggtac    1020
agagctgaat tgtctgaaga cgatgtattt gtaattccag cagcttatcc atttgtcgtc    1080
aacgctacct caaacctcaa tttccttgct tttggtatca atgctgagaa caaccagagg    1140
aacttccttg caggcgagaa agacaatgtg gtaaggcaga tagaaagaca agtgcaggag    1200
cttgcgttcc ctgggtctgc acaagatgtt gagaggctat taaagaagca gagggaatcc    1260
tactttgttg atgctcagcc tcagcagaag gaggagggga gtaagggaag aaagggtcct    1320
tttccttcaa tcttaggtgc tctctactga                                     1350
```

<210> SEQ ID NO 85
<211> LENGTH: 1350
<212> TYPE: DNA
<213> ORGANISM: Glycine max

<400> SEQUENCE: 85

```
atgatgagag tgcggtttcc tttgttggtg ttgctgggaa ctgttttcct ggcatcagtt      60
tgtgtctcat taaaggacta caaggacgac gatgacaagc ttaaggtgag agaggatgag     120
aataacccctt tctacttgag aagctctaac agcttccaaa ctctctttga aaccaaaaac    180
ggtcgcattc gtctcattca gagattcaac aaacgctccc acaacttga gaaccttcga      240
gactaccgga ttgtccagat tcagtcaaaa cccaacacaa tcattctccc ccaccatgct     300
gacgccgatt tcattattat tattcttagc gggagagcca tacttacctt ggtgaacaac     360
gacgacagag actcctacaa cattcaccct ggcgatgccc agagaatccc agctggaacc     420
acttactata ttattaaccc tcacgaccac cagaatctca aaataatcaa aattgccata     480
cccgtcaaca aacctggcag atatgatgat ttcttcttat ctagcactca agcccaacag     540
```

-continued

```
tcctacttgc aaggcttcag ccataatatt ctagagacct ccttccatag cgaattcgag      600
gagataaaca gggttttgtt gggagaggaa gaggagcaga ggcagcaaga gggagtgatc      660
gtggaactct caaggaaca aattcggcaa ctgagcagac gtgccaaatc tagttcaagg       720
aaaaccattt cctccgaaga tgaaccattc aacttgagaa gccgcaaccc catctattcc     780
aacaactttg gaaagttctt tgagatcacc cctgagaaaa acccacagct tcggacttg      840 gatatcttcc tcagttctgt ggatatcaac gaaggagctc ttcttctacc acacttcaat     900
tcaaaggcca tagtgatact agtgattaat gaaggagatg caaacattga acttgttggc     960
attaaagaac aacaacagaa gcagaaacag gaagaggaac ctttggaagt gcaaaggtac    1020
agagctgaat tgtctgaaga cgatattatt gtaattccag cagcttatcc atttgtcgtc    1080
aacgctacct caaacctcaa tattattgct attggtatca atgctgagaa caaccagagg    1140
aacttccttg caggcgagaa agacaatgtg taaggcaga tagaaagaca agtgcaggag     1200
cttgcgttcc ctgggtctgc acaagatgtt gagaggctat taaagaagca gagggaatcc    1260
tactttgttg atgctcagcc tcagcagaag gaggagggga gtaagggaag aaagggtcct    1320
tttccttcaa tcttaggtgc tctctactga                                     1350
```

<210> SEQ ID NO 86
<211> LENGTH: 1350
<212> TYPE: DNA
<213> ORGANISM: Glycine max

<400> SEQUENCE: 86

```
atgatgagag tgcggtttcc tttgttggtg ttgctgggaa ctgttttcct ggcatcagtt      60
tgtgtctcat taaggacta caaggacgac gatgacaagc ttaaggtgag agaggatgag     120
ataacccctt tctacttgag aagctctaac agcttccaaa ctctctttga gaaccaaaac     180
ggtcgcattc gtctcattca gagattcaac aaacgctccc cacaacttga gaaccttcga     240
gactaccgga ttgtccagat tcagtcaaaa cccaacacaa tcattctccc ccaccatgct     300
gacgccgatt tcattattat tattcttagc gggagagcca taattaccat tgtgaacaac     360
gacgacagag actcctacaa cattcaccct ggcgatgcca ttagaatccc agctggaacc    420
acttactata ttattaaccc tcacgaccac cagaatctca aaataatcaa aattgccata    480
cccgtcaaca aacctggcag atatgatgat ttcttcttat ctagcactca agcccaacag    540
tcctacttgc aaggcttcag ccataatatt ctagagacct ccttccatag cgaattcgag    600
gagataaaca gggttttgtt gggagaggaa gaggagcaga ggcagcaaga gggagtgatc    660
gtggaactct caaggaaca aattcggcaa ctgagcagac gtgccaaatc tagttcaagg     720
aaaaccattt cctccgaaga tgaaccattc aacttgagaa gccgcaaccc catctattcc   780
aacaactttg gaaagttctt tgagatcacc cctgagaaaa acccacagct tcggacttg    840 gatatcttcc tcagttctgt ggatatcaac gaaggagctc ttcttctacc acacttcaat   900
tcaaaggcca tagtgatact agtgattaat gaaggagatg caaacattga aattgttggc   960
attaaagaac aacaacagaa gcagaaacag gaagaggaac ctttggaagt gcaaaggtac  1020
agagctgaat tgtctgaaga cgatattatt gtaattccag cagcttatcc atttgtcatt  1080
aacgctacct caaacctcaa tattattgct attggtatca atgctgagaa caaccagagg  1140
aacttccttg caggcgagaa agacaatgtg taaggcaga tagaaagaca agtgcaggag   1200
cttgcgttcc ctgggtctgc acaagatgtt gagaggctat taaagaagca gagggaatcc  1260
```

```
tactttgttg atgctcagcc tcagcagaag gaggagggga gtaagggaag aaagggtcct    1320
tttccttcaa tcttaggtgc tctctactga                                    1350
```

<210> SEQ ID NO 87
<211> LENGTH: 1350
<212> TYPE: DNA
<213> ORGANISM: Glycine max

<400> SEQUENCE: 87

```
atgatgagag tgcggtttcc tttgttggtg ttgctgggaa ctgttttcct ggcatcagtt     60
tgtgtctcat taaggactaa caaggacgac gatgacaagc ttggtaccga gctcggatcc    120
actagtaacg gccgccagtg tgctggaatt cggcttatac tatgatgaga gtgcggtttc    180
ctttgttggt gttgctggga actgttttcc tggcatcagt ttgtgtctca cttaaggtga    240
gagaggatga gaataaccct ttctacatta gaagctctaa cagcttccaa actctctttg    300
agaaccaaaa cattcgcatt cgtctcattc agagattcaa caaacgctcc ccacaaattg    360
agaaccttcg agactacatt attgtccaga ttcagtcaaa acccaacaca atcattctcc    420
cccaccatgc tgacgccgat ttcattatta ttattcttag cgggagagcc ataattacca    480
ttgtgaacaa cgacgacaga gactcctaca acattcaccc tggcattgcc attagaatcc    540
cgctggaacc cttactatat tattaaccct cacgaccacc agaatctcaa ataatcaaa     600 attgccatac ccgtcaacaa acctggcaga tatgatgatt tcttcttatc tagcactcaa    660
gcccaacagt cctacttgca aggcttcagc cataatattc tagagacctc cttccatagc    720
gaattcgagg agataaacag ggttttgttg ggagaggaag aggagcagag gcagcaagag    780
ggagtgatcg tggaactctc aaaggaacaa attcggcaac tgagcagacg tgccaaatct    840
agttcaagga aaaccatttc ctccgaagat gaaccattca acttgagaag ccgcaacccc    900
atctattcca caactttggg aaagatttt gagatcaccc ctgagaaaaa cccacagatt    960
cgggacttgg atatcttcat tagttctgtg atatcaacg aaggagctct tattctacca    1020
cacttcaatt caaggccat agtgataatt gtgattaatg aaggagatgc aaacattgaa    1080
attgttggca ttaagaaaca acaacagaag cagaaacagg aagaggaacc tttggaagtg    1140
caaaggtaca gagctgaatt gtctgaagac gatattattg taattccagc agcttatcca    1200
tttgtcgtca acgctacctc aaacctcaat attattgcta ttggtatcaa tgctgagaac    1260
aaccagagga acttccttgc aggcagaaaa gacaatgtgg taaggcagat agaaagacaa    1320
gtgcaggagc ttgcgttccc tgggtctgca                                    1350
```

<210> SEQ ID NO 88
<211> LENGTH: 3808
<212> TYPE: DNA
<213> ORGANISM: Glycine max

<400> SEQUENCE: 88

```
taggatcctt caatagaaaa tgtgttattt cctcatcacc agacaaaggg gcaacagtta     60
acaaaacaaa tttatgtttc atttgagatt aaggaaggta aggaagaaaa aagattaaaa    120
aaaatgtcct tatctctttg tttctgtaat aataatataa gagacttaaa cttttaatat    180
aataattgta attaggtttt ctagtcatga gcaccactca gagacaagat ttcaagaaaa    240
caattttgtt aaacatctta ttagaaactt ttagttaagt cttgaagtta gaattaaaca    300
aaaaaaatta cacacgagaa acacaataaa cccactaccg tcaggttatc ataaggatga    360
aatgttttga tatcattaaa tataacacac acaaaaatac atctaattat aacaatatat    420
```

-continued

```
gttatacata tattttttgta aaaacttaga gtttttcaaa acattctaat acatgattag      480
agtttataga aatacaaata tttaaaaaat ataattttaa aaaaacattc taaagtcatt      540
cagatcctct cacacctgtg tgatcattta gtcatgtatg tagtacaatc attgtagttc      600
acaacagagt aaaataaata aggataaact agggaatata tataatatat acaattaaat      660
aaaaaaggga aaatcaaatt agaatttttg attccccaca tgacacaact caccatgcac      720
gctgccacct cagctccctc ctctccacac atgtctcatg tcactttcga ctttggcttt      780
ttcactatga cacaactcgc catgcatgtt gccacgtgag ctccttcctc ttcccatgat      840
gacaccactg ggcatgcatg ctgccacctc agctcccacc tcttctcatt atgagcctac      900
tggccatgca cactgccacc tcagcactcc tctcacttcc cattgctacc tgccaaaccg      960
cttctctcca taaatatcta tttaaattta aactaattat ttcatatact tttttgatga     1020
cgtggatgca ttgccatcgt tgtttaataa ttgttaattt ggagttgaat aataaaatga     1080
aagaaaaaag ttggaaagat tttgcatttg ttgttgtata aatagagaag agagtgatgg     1140
ttaatgcatg aatgcatgat cagatctggt accatgatga gagtgcggtt cctttgttg      1200 gtgttgctgg gaactgtttt cctggcatca gtttgtgtct cattaaagga ctacaaggac     1260
gacgatgaca agcttaaggt gagagaggat gagaataacc ctttctactt gagaagctct     1320
aacagcttcc aaactctctt tgagaaccaa aacggtcgca ttcgtctcct ccagagattc     1380
aacaaacgct ccccacaact tgagaacctt cgagactacc ggattgtcca gtttcagtca     1440
aaacccaaca caatccttct cccccaccat gctgacgccg atttcctcct ctttgtcctt     1500
agcgggagag ccatacttac cttggtgaac aacgacgaca gagactccta caaccttcac     1560
cctggcgatg cccagagaat cccagctgga accacttact atttggttaa ccctcacgac     1620
caccagaatc tcaaaataat caaacttgcc atacccgtca acaaacctgg cagatatgat     1680
gatttcttct tatctagcac tcaagcccaa cagtcctact gcaaggctt cagccataat      1740 attctagaga cctccttcca tagcgaattc gaggagataa acagggtttt gttgggagag     1800
gaagaggagc agaggcagca agagggagtg atcgtggaac tctcaaagga acaaattcgg     1860
caactgagca gacgtgccaa atctagttca aggaaaacca tttcctccga agatgaacca     1920
ttcaacttga gaagccgcaa ccccatctat tccaacaact ttggaaagtt ctttgagatc     1980 accctgaga aaacccaca gcttcgggac ttggatatct tcctcagttc tgtggatatc      2040
aacgaaggag ctcttcttct accacacttc aattcaaagg ccatagtgat actagtgatt     2100
aatgaaggag atgcaaacat tgaacttgtt ggcattaaag aacaacaaca gaagcagaaa     2160
caggaagagg aacctttgga agtgcaaagg tacagagctg aattgtctga agacgatgta     2220
tttgtaattc cagcagctta tccatttgtc gtcaacgcta cctcaaacct caatttcctt     2280
gcttttggta tcaatgctga gaacaaccag aggaacttcc ttgcaggcga aaagacaat      2340 gtggtaaggc agatagaaag acaagtgcag gagcttgcgt tccctgggtc tgcacaagat     2400
gttgagaggc tattaaagaa gcagagggaa tcctactttg ttgatgctca gcctcagcag     2460
aaggaggagg ggagtaaggg aagaaagggt ccttttcctt caatcttagg tgctctctac     2520
tgaataacaa gccgaattct gcagaattca ctcccaaaac caccttccct gtgacagtta     2580
aaccctgctt ataccttttcc tcctaataat gttcatctgt cacacaaact aaaataaata     2640
aaatgggagc aataaataaa atgggagctc atatatttac accatttaca ctgtctatta     2700
ttcaccatgc caattattac ttcataattt taaaattatg tcatttttaa aaattgctta     2760
```

-continued

```
atgatggaaa ggattattat aagttaaaag tataacatag ataaactaac cacaaaacaa    2820
atcaatataa actaacttac tctcccatct aatttttatt taaatttctt tacacttctc    2880
ttccatttct atttctacaa cattatttaa cattttta tt gtattttct tactttctaa    2940 ctctattcat ttcaaaaatc aatatatgtt tatcaccacc tctctaaaaa aaactttaca    3000
atcattggtc cagaaaagtt aaatcacgag atggtcattt tagcattaaa acaacgattc    3060
ttgtatcact attttcagc atgtagtcca ttctcttcaa acaaagacag cggctatata     3120
atcgttgtgt tatattcagt ctaaaacaat tgttatggta aaagtcgtca ttttacgcct    3180
ttttaaaaga tataaaatga caattatggt taaaagtcat catgttagat cctccttaaa    3240
gatataaaat gacagttttg ataaaaagtg gtcattttat acgctcttga agatataaaa    3300
acgacggtta tggtaaaagc tgccatttta aatgaaatat ttttgtttta gttcattttg    3360
tttaatgcta atcccattta aattgacttg tacaattaaa actcacccac ccagatacaa    3420
tataaactaa cttactctca cagctaagtt ttatttaaat ttcttacac ttcttttcca     3480 tttctatttc tatgacatta actaacattt ttctcgtaat ttttttcttt attttctaac    3540
tctatccatt tcaaatcgat atatgtttat caccaccact ttaaaagaa aatttacaat     3600 ttctcgtgca aaaaagctaa atcatgaccg tcattttagc attaaaacaa cgattcttgt    3660
atcgttgttt ttcagcatgt agtccattct tttcaagcaa agacaacagc tatataatca    3720
tcgtgttata ttcagtctaa aacaacagta atgataaaag tcatcatttt aggcctttct    3780
gaaatatata gaacgacatt catggtaa                                       3808
```

<210> SEQ ID NO 89
<211> LENGTH: 449
<212> TYPE: PRT
<213> ORGANISM: Glycine max

<400> SEQUENCE: 89

```
Met Met Arg Val Arg Phe Pro Leu Leu Val Leu Leu Gly Thr Val Phe
1               5                   10                  15

Leu Ala Ser Val Cys Val Ser Leu Lys Asp Tyr Lys Asp Asp Asp Asp
                20                  25                  30

Lys Leu Lys Val Arg Glu Asp Glu Asn Asn Pro Phe Tyr Leu Arg Ser
            35                  40                  45

Ser Asn Ser Phe Gln Thr Leu Phe Glu Asn Gln Asn Gly Arg Ile Arg
        50                  55                  60

Leu Leu Gln Arg Phe Asn Lys Arg Ser Pro Gln Leu Glu Asn Leu Arg
65                  70                  75                  80

Asp Tyr Arg Ile Val Gln Phe Gln Ser Lys Pro Asn Thr Ile Leu Leu
                85                  90                  95

Pro His His Ala Asp Ala Asp Phe Leu Leu Phe Val Leu Ser Gly Arg
            100                 105                 110

Ala Ile Leu Thr Leu Val Asn Asn Asp Asp Arg Asp Ser Tyr Asn Leu
        115                 120                 125

His Pro Gly Asp Ala Gln Arg Ile Pro Ala Gly Thr Thr Tyr Tyr Leu
    130                 135                 140

Val Asn Pro His Asp His Gln Asn Leu Lys Ile Ile Lys Leu Ala Ile
145                 150                 155                 160

Pro Val Asn Lys Pro Gly Arg Tyr Asp Asp Phe Phe Leu Ser Ser Thr
                165                 170                 175

Gln Ala Gln Gln Ser Tyr Leu Gln Gly Phe Ser His Asn Ile Leu Glu
            180                 185                 190
```

```
Thr Ser Phe His Ser Glu Phe Glu Glu Ile Asn Arg Val Leu Leu Gly
            195                 200                 205

Glu Glu Glu Glu Gln Arg Gln Gln Gly Val Ile Val Glu Leu Ser
        210                 215                 220

Lys Glu Gln Ile Arg Gln Leu Ser Arg Arg Ala Lys Ser Ser Ser Arg
225                 230                 235                 240

Lys Thr Ile Ser Ser Glu Asp Glu Pro Phe Asn Leu Arg Ser Arg Asn
                245                 250                 255

Pro Ile Tyr Ser Asn Asn Phe Gly Lys Phe Glu Ile Thr Pro Glu
            260                 265                 270

Lys Asn Pro Gln Leu Arg Asp Leu Asp Ile Phe Leu Ser Ser Val Asp
        275                 280                 285

Ile Asn Glu Gly Ala Leu Leu Leu Pro His Phe Asn Ser Lys Ala Ile
            290                 295                 300

Val Ile Leu Val Ile Asn Glu Gly Asp Ala Asn Ile Glu Leu Val Gly
305                 310                 315                 320

Ile Lys Glu Gln Gln Gln Lys Gln Lys Gln Glu Glu Pro Leu Glu
                325                 330                 335

Val Gln Arg Tyr Arg Ala Glu Leu Ser Glu Asp Asp Val Phe Val Ile
            340                 345                 350

Pro Ala Ala Tyr Pro Phe Val Val Asn Ala Thr Ser Asn Leu Asn Phe
            355                 360                 365

Leu Ala Phe Gly Ile Asn Ala Glu Asn Asn Gln Arg Asn Phe Leu Ala
        370                 375                 380

Gly Glu Lys Asp Asn Val Val Arg Gln Ile Glu Arg Gln Val Gln Glu
385                 390                 395                 400

Leu Ala Phe Pro Gly Ser Ala Gln Asp Val Glu Arg Leu Leu Lys Lys
                405                 410                 415

Gln Arg Glu Ser Tyr Phe Val Asp Ala Gln Pro Gln Gln Lys Glu Glu
            420                 425                 430

Gly Ser Lys Gly Arg Lys Gly Pro Phe Pro Ser Ile Leu Gly Ala Leu
        435                 440                 445

Tyr

<210> SEQ ID NO 90
<211> LENGTH: 3808
<212> TYPE: DNA
<213> ORGANISM: Glycine max

<400> SEQUENCE: 90
taggatcctt caatagaaaa tgtgttattt cctcatcacc agacaaaggg gcaacagtta      60
acaaaacaaa tttatgtttc atttgagatt aaggaaggta aggaagaaaa aagattaaaa     120
aaaatgtcct tatctctttg tttctgtaat aataatataa gagacttaaa cttttaatat     180
aataattgta attaggtttt ctagtcatga gcaccactca gagacaagat ttcaagaaaa     240
caattttgtt aaacatctta ttagaaactt ttagttaagt cttgaagtta gaattaaaca     300
aaaaaaatta cacgagaa acacaataaa cccactaccg tcaggttatc ataaggatga      360
aatgttttga tatcattaaa tataacacac acaaaaatac atctaattat aacaatatat     420
gttatacata tatttttgta aaacttaga gttttcaaa acattctaat acatgattag      480 agttttataga aatacaaata tttaaaaaat ataatttaa aaaaacattc taaagtcatt     540
cagatcctct cacacctgtg tgatcattta gtcatgtatg tagtacaatc attgtagttc     600
```

-continued

| | |
|---|---|
| acaacagagt aaaataaata aggataaact agggaatata tataatatat acaattaaat | 660 |
| aaaaaaggga aaatcaaatt agaatttttg attccccaca tgacacaact caccatgcac | 720 |
| gctgccacct cagctccctc ctctccacac atgtctcatg tcactttcga ctttggcttt | 780 |
| ttcactatga cacaactcgc catgcatgtt gccacgtgag ctccttcctc ttcccatgat | 840 |
| gacaccactg gcatgcatg ctgccacctc agctcccacc tcttctcatt atgagcctac | 900 |
| tggccatgca cactgccacc tcagcactcc tctcacttcc cattgctacc tgccaaaccg | 960 |
| cttctctcca taaatatcta tttaaattta aactaattat ttcatatact tttttgatga | 1020 |
| cgtggatgca ttgccatcgt tgtttaataa ttgttaattt ggagttgaat aataaaatga | 1080 |
| aagaaaaaag ttggaaagat tttgcatttg ttgttgtata aatagagaag agagtgatgg | 1140 |
| ttaatgcatg aatgcatgat cagatctggt accatgatga gagtgcggtt tcctttgttg | 1200 |
| gtgttgctgg gaactgtttt cctggcatca gtttgtgtct cattaaagga ctacaaggac | 1260 |
| gacgatgaca agcttaaggt gagagaggat gagaataacc ctttctactt gagaagctct | 1320 |
| aacagcttcc aaactctctt tgagaaccaa aacggtcgca ttcgtctcat tcagagattc | 1380 |
| aacaaacgct ccccacaact tgagaaccctt cgagactacc ggattgtcca gtttcagtca | 1440 |
| aaacccaaca caatcattct cccccaccat gctgacgccg atttcattat tattattctt | 1500 |
| agcgggagag ccatacttac cttggtgaac aacgacgaca gagactccta caacattcac | 1560 |
| cctggcgatg cccagagaat cccagctgga accacttact atattattaa ccctcacgac | 1620 |
| caccagaatc tcaaaataat caaaattgcc atacccgtca acaaacctgg cagatatgat | 1680 |
| gatttcttct tatctagcac tcaagcccaa cagtcctact tgcaaggctt cagccataat | 1740 |
| attctagaga cctccttcca tagcgaattc gaggagataa acagggtttt gttgggagag | 1800 |
| gaagaggagc agaggcagca agagggagtg atcgtggaac tctcaaagga acaaaattcgg | 1860 |
| caactgagca gacgtgccaa atctagttca aggaaaacca tttcctccga agatgaacca | 1920 |
| ttcaacttga gaagccgcaa ccccatctat tccaacaact ttggaaagtt ctttgagatc | 1980 |
| acccctgaga aaaacccaca gcttcgggac ttggatatct tcctcagttc tgtggatatc | 2040 |
| aacgaaggag ctcttcttct accacacttc aattcaaagg ccatagtgat actagtgatt | 2100 |
| aatgaaggag atgcaaacat tgaacttgtt ggcattaaag aacaacaaca gaagcagaaa | 2160 |
| caggaagagg aacctttgga agtgcaaagg tacagagctg aattgtctga agacgatgta | 2220 |
| tttgtaattc cagcagctta tccatttgtc gtcaacgcta cctcaaacct caatttcctt | 2280 |
| gcttttggta tcaatgctga gaacaaccag aggaacttcc ttgcaggcga gaaagacaat | 2340 |
| gtggtaaggc agatagaaag acaagtgcag gagcttgcgt tccctgggtc tgcacaagat | 2400 |
| gttgagaggc tattaaagaa gcagagggaa tcctactttg ttgatgctca gcctcagcag | 2460 |
| aaggaggagg ggagtaaggg aagaaagggt ccttttcctt caatcttagg tgctctctac | 2520 |
| tgaataacaa gccgaattct gcagaattca ctcccaaaac caccttccct gtgacagtta | 2580 |
| aaccctgctt atacctttcc tcctaataat gttcatctgt cacacaaact aaaataaata | 2640 |
| aaatgggagc aataaataaa atgggagctc atatatttac accatttaca ctgtctatta | 2700 |
| ttcaccatgc caattattac ttcataattt taaaattatg tcattttaa aaattgctta | 2760 |
| atgatgaaa ggattattat aagttaaaag tataacatag ataaactaac cacaaaacaa | 2820 |
| atcaatataa actaacttac tctcccatct aatttttatt taaatttctt tacacttctc | 2880 |
| ttccatttct atttctacaa cattatttaa catttttatt gtattttct tactttctaa | 2940 |
| ctctattcat ttcaaaaatc aatatatgtt tatcaccacc tctctaaaaa aaactttaca | 3000 |

```
atcattggtc cagaaaagtt aaatcacgag atggtcattt tagcattaaa acaacgattc    3060
ttgtatcact attttcagc atgtagtcca ttctcttcaa acaaagacag cggctatata     3120
atcgttgtgt tatattcagt ctaaaacaat tgttatggta aaagtcgtca ttttacgcct    3180 tttaaaaga tataaaatga caattatggt taaaagtcat catgttagat cctccttaaa     3240
gatataaaat gacagttttg ataaaaagtg gtcattttat acgctcttga aagatataaa   3300
acgacggtta tggtaaaagc tgccatttta aatgaaatat ttttgtttta gttcattttg    3360
tttaatgcta atcccattta aattgacttg tacaattaaa actcacccac ccagatacaa    3420
tataaactaa cttactctca cagctaagtt ttattttaaat ttctttacac ttcttttcca   3480
tttctatttc tatgcattta actaacattt ttctcgtaat ttttttttctt attttctaac   3540 tctatccatt tcaaatcgat atatgtttat caccaccact ttaaaaagaa aatttacaat    3600
ttctcgtgca aaaaagctaa atcatgaccg tcattttagc attaaaacaa cgattcttgt   3660
atcgttgttt ttcagcatgt agtccattct tttcaagcaa agacaacagc tatataatca    3720
tcgtgttata ttcagtctaa aacaacagta atgataaaag tcatcatttt aggcctttct    3780
gaaatatata gaacgacatt catggtaa                                       3808
```

<210> SEQ ID NO 91
<211> LENGTH: 449
<212> TYPE: PRT
<213> ORGANISM: Glycine max

<400> SEQUENCE: 91

```
Met Met Arg Val Arg Phe Pro Leu Leu Val Leu Leu Gly Thr Val Phe
 1               5                  10                  15

Leu Ala Ser Val Cys Val Ser Leu Lys Asp Tyr Lys Asp Asp Asp
            20                  25                  30

Lys Leu Lys Val Arg Glu Asp Glu Asn Asn Pro Phe Tyr Leu Arg Ser
        35                  40                  45

Ser Asn Ser Phe Gln Thr Leu Phe Glu Asn Gln Asn Gly Arg Ile Arg
    50                  55                  60

Leu Ile Gln Arg Phe Asn Lys Arg Ser Pro Gln Leu Glu Asn Leu Arg
65                  70                  75                  80

Asp Tyr Arg Ile Val Gln Phe Gln Ser Lys Pro Asn Thr Ile Ile Leu
                85                  90                  95

Pro His His Ala Asp Ala Asp Phe Ile Ile Ile Leu Ser Gly Arg
            100                 105                 110

Ala Ile Leu Thr Leu Val Asn Asn Asp Asp Arg Asp Ser Tyr Asn Ile
        115                 120                 125

His Pro Gly Asp Ala Gln Arg Ile Pro Ala Gly Thr Thr Tyr Tyr Ile
    130                 135                 140

Ile Asn Pro His Asp His Gln Asn Leu Lys Ile Lys Ile Ala Ile
145                 150                 155                 160

Pro Val Asn Lys Pro Gly Arg Tyr Asp Asp Phe Phe Leu Ser Ser Thr
                165                 170                 175

Gln Ala Gln Gln Ser Tyr Leu Gln Gly Phe Ser His Asn Ile Leu Glu
            180                 185                 190

Thr Ser Phe His Ser Glu Phe Glu Glu Ile Asn Arg Val Leu Leu Gly
        195                 200                 205

Glu Glu Glu Glu Gln Arg Gln Gln Glu Gly Val Ile Val Glu Leu Ser
    210                 215                 220
```

```
Lys Glu Gln Ile Arg Gln Leu Ser Arg Arg Ala Lys Ser Ser Ser Arg
225                 230                 235                 240

Lys Thr Ile Ser Ser Glu Asp Glu Pro Phe Asn Leu Arg Ser Arg Asn
            245                 250                 255

Pro Ile Tyr Ser Asn Asn Phe Gly Lys Phe Phe Glu Ile Thr Pro Glu
        260                 265                 270

Lys Asn Pro Gln Leu Arg Asp Leu Asp Ile Phe Leu Ser Ser Val Asp
    275                 280                 285

Ile Asn Glu Gly Ala Leu Leu Leu Pro His Phe Asn Ser Lys Ala Ile
290                 295                 300

Val Ile Leu Val Ile Asn Glu Gly Asp Ala Asn Ile Glu Leu Val Gly
305                 310                 315                 320

Ile Lys Glu Gln Gln Gln Lys Gln Lys Gln Glu Glu Pro Leu Glu
                325                 330                 335

Val Gln Arg Tyr Arg Ala Glu Leu Ser Glu Asp Asp Val Phe Val Ile
            340                 345                 350

Pro Ala Ala Tyr Pro Phe Val Val Asn Ala Thr Ser Asn Leu Asn Phe
        355                 360                 365

Leu Ala Phe Gly Ile Asn Ala Glu Asn Asn Gln Arg Asn Phe Leu Ala
370                 375                 380

Gly Glu Lys Asp Asn Val Val Arg Gln Ile Glu Arg Gln Val Gln Glu
385                 390                 395                 400

Leu Ala Phe Pro Gly Ser Ala Gln Asp Val Glu Arg Leu Leu Lys Lys
            405                 410                 415

Gln Arg Glu Ser Tyr Phe Val Asp Ala Gln Pro Gln Gln Lys Glu Glu
        420                 425                 430

Gly Ser Lys Gly Arg Lys Gly Pro Phe Pro Ser Ile Leu Gly Ala Leu
    435                 440                 445

Tyr

<210> SEQ ID NO 92
<211> LENGTH: 3808
<212> TYPE: DNA
<213> ORGANISM: Glycine max

<400> SEQUENCE: 92
taggatcctt caatagaaaa tgtgttattt cctcatcacc agacaaaggg gcaacagtta    60
acaaaacaaa tttatgtttc atttgagatt aaggaaggta aggaagaaaa aagattaaaa   120
aaaatgtcct tatctctttg tttctgtaat aataatataa gagacttaaa cttttaatat   180 ataattgta attaggtttt ctagtcatga gcaccactca gagacaagat ttcaagaaaa   240
caattttgtt aaacatctta ttagaaactt ttagttaagt cttgaagtta gaattaaaca   300 aaaaaatta cacacgagaa acacaataaa cccactaccg tcaggttatc ataaggatga   360
aatgttttga tatcattaaa tataacacac acaaaaatac atctaattat aacaatatat   420
gttatacata tatttttgta aaaacttaga gttttcaaa acattctaat acatgattag   480
agtttataga aatacaaata tttaaaaaat ataattttaa aaaaacattc taaagtcatt   540
cagatcctct cacacctgtg tgatcattta gtcatgtatg tagtacaatc attgtagttc   600
acaacagagt aaaataaata aggataaact agggaatata tataatatat acaattaaat   660
aaaaaaggga aaatcaaatt agaatttttg attccccaca tgacacaact caccatgcac   720
gctgccacct cagctcccct ctctccacac atgtctcatg tcactttcga ctttggcttt   780
ttcactatga cacaactcgc catgcatgtt gccacgtgag ctccttcctc ttcccatgat   840
```

```
gacaccactg ggcatgcatg ctgccacctc agctcccacc tcttctcatt atgagcctac    900
tggccatgca cactgccacc tcagcactcc tctcacttcc cattgctacc tgccaaaccg    960
cttctctcca taaatatcta tttaaattta aactaattat ttcatatact tttttgatga   1020
cgtggatgca ttgccatcgt tgtttaataa ttgttaattt ggagttgaat aataaaatga   1080
aagaaaaaag ttggaaagat tttgcatttg ttgttgtata aatagagaag agagtgatgg   1140
ttaatgcatg aatgcatgat cagatctggt accatgatga gagtgcggtt tcctttgttg   1200
gtgttgctgg gaactgtttt cctggcatca gtttgtgtct cattaaagga ctacaaggac   1260
gacgatgaca agcttaaggt gagagaggat gagaataacc ctttctactt gagaagctct   1320
aacagcttcc aaactctctt tgagaaccaa aacggtcgca ttcgtctcat tcagagattc   1380
aacaaacgct ccccacaact tgagaacctt cgagactacc ggattgtcca gattcagtca   1440
aaacccaaca caatcattct cccccaccat gctgacgccg atttcattat tattattctt   1500
agcgggagag ccatacttac cttggtgaac aacgacgaca gagactccta caacattcac   1560
cctggcgatg cccagagaat cccagctgga accacttact atattattaa ccctcacgac   1620
caccagaatc tcaaaataat caaaattgcc atacccgtca caaacctgg cagatatgat    1680
gatttcttct tatctagcac tcaagcccaa cagtcctact tgcaaggctt cagccataat   1740
attctagaga cctccttcca tagcgaattc gaggagataa acagggtttt gttgggagag   1800
gaagaggagc agaggcagca agagggagtg atcgtggaac tctcaaagga acaaattcgg   1860
caactgagca gacgtgccaa atctagttca aggaaaacca tttcctccga agatgaacca   1920
ttcaacttga gaagccgcaa ccccatctat tccaacaact ttggaaagtt ctttgagatc   1980
accccctgaga aaacccaca gcttcgggac ttggatatct tcctcagttc tgtggatatc   2040
aacgaaggag ctcttcttct accacacttc aattcaaagg ccatagtgat actagtgatt   2100
aatgaaggag atgcaaacat tgaacttgtt ggcattaaag aacaacaaca gaagcagaaa   2160
caggaagagg aacctttgga agtgcaaagg tacagagctg aattgtctga agacgatatt   2220
attgtaattc cagcagctta tccatttgtc gtcaacgcta cctcaaacct caatattatt   2280
gctattggta tcaatgctga gaacaaccag aggaacttcc ttgcaggcga aaagacaat    2340
gtggtaaggc agatagaaag acaagtgcag gagcttgcgt tccctgggtc tgcacaagat   2400
gttgagaggc tattaaagaa gcagagggaa tcctactttg ttgatgctca gcctcagcag   2460
aaggaggagg ggagtaaggg aagaaagggt ccttttcctt caatcttagg tgctctctac   2520
tgaataacaa gccgaattct gcagaattca ctcccaaaac caccttccct gtgacagtta   2580
aaccctgctt atacctttcc tcctaataat gttcatctgt cacacaaact aaaataaata   2640
aaatgggagc aataaataaa atgggagctc atatatttac accatttaca ctgtctatta   2700
ttcaccatgc caattattac ttcataattt taaaattatg tcatttttaa aaattgctta   2760
atgatggaaa ggattattat aagttaaaag tataacatag ataaactaac cacaaaacaa   2820
atcaatataa actaacttac tctcccatct aattttatt taaatttctt tacacttctc    2880
ttccatttct atttctacaa cattatttaa catttttatt gtattttct tactttctaa     2940
ctctattcat ttcaaaaatc aatatatgtt tatcaccacc tctctaaaaa aactttaca    3000
atcattggtc cagaaaagtt aaatcacgag atggtcattt tagcattaaa acaacgattc   3060
ttgtatcact atttttcagc atgtagtcca ttctcttcaa acaaagacag cggctatata   3120
atcgttgtgt tatattcagt ctaaaacaat tgttatggta aaagtcgtca ttttacgcct   3180
```

-continued

```
ttttaaaaga tataaaatga caattatggt taaaagtcat catgttagat cctccttaaa    3240
gatataaaat gacagttttg ataaaaagtg gtcatttttat acgctcttga aagatataaa    3300
acgacggtta tggtaaaagc tgccatttta aatgaaatat ttttgtttta gttcattttg    3360
tttaatgcta atcccattta aattgacttg tacaattaaa actcacccac ccagatacaa    3420
tataaactaa cttactctca cagctaagtt ttatttaaat ttctttacac ttcttttcca    3480
tttctatttc tatgacatta actaacattt ttctcgtaat ttttttttctt attttctaac    3540 tctatccatt tcaaatcgat atatgtttat caccaccact ttaaaaagaa aatttacaat    3600
ttctcgtgca aaaagctaa atcatgaccg tcattttagc attaaaacaa cgattcttgt    3660
atcgttgttt ttcagcatgt agtccattct tttcaagcaa agacaacagc tatataatca    3720
tcgtgttata ttcagtctaa aacaacagta atgataaaag tcatcatttt aggcctttct    3780
gaaatatata gaacgacatt catggtaa                                        3808
```

<210> SEQ ID NO 93
<211> LENGTH: 449
<212> TYPE: PRT
<213> ORGANISM: Glycine max

<400> SEQUENCE: 93

```
Met Met Arg Val Arg Phe Pro Leu Leu Val Leu Leu Gly Thr Val Phe
  1               5                  10                  15

Leu Ala Ser Val Cys Val Ser Leu Lys Asp Tyr Lys Asp Asp Asp Asp
                 20                  25                  30

Lys Leu Lys Val Arg Glu Asp Glu Asn Asn Pro Phe Tyr Leu Arg Ser
             35                  40                  45

Ser Asn Ser Phe Gln Thr Leu Phe Glu Asn Gln Asn Gly Arg Ile Arg
         50                  55                  60

Leu Ile Gln Arg Phe Asn Lys Arg Ser Pro Gln Leu Glu Asn Leu Arg
 65                  70                  75                  80

Asp Tyr Arg Ile Val Gln Ile Gln Ser Lys Pro Asn Thr Ile Ile Leu
                 85                  90                  95

Pro His His Ala Asp Ala Asp Phe Ile Ile Ile Leu Ser Gly Arg
            100                 105                 110

Ala Ile Leu Thr Leu Val Asn Asn Asp Asp Arg Asp Ser Tyr Asn Ile
        115                 120                 125

His Pro Gly Asp Ala Gln Arg Ile Pro Ala Gly Thr Thr Tyr Tyr Ile
    130                 135                 140

Ile Asn Pro His Asp His Gln Asn Leu Lys Ile Ile Lys Ile Ala Ile
145                 150                 155                 160

Pro Val Asn Lys Pro Gly Arg Tyr Asp Asp Phe Phe Leu Ser Ser Thr
                165                 170                 175

Gln Ala Gln Gln Ser Tyr Leu Gln Gly Phe Ser His Asn Ile Leu Glu
            180                 185                 190

Thr Ser Phe His Ser Glu Phe Glu Glu Ile Asn Arg Val Leu Leu Gly
        195                 200                 205

Glu Glu Glu Gln Arg Gln Gln Glu Gly Val Ile Val Glu Leu Ser
    210                 215                 220

Lys Glu Gln Ile Arg Gln Leu Ser Arg Arg Ala Lys Ser Ser Ser Arg
225                 230                 235                 240

Lys Thr Ile Ser Ser Glu Asp Glu Pro Phe Asn Leu Arg Ser Arg Asn
                245                 250                 255

Pro Ile Tyr Ser Asn Asn Phe Gly Lys Phe Phe Glu Ile Thr Pro Glu
```

-continued

```
                260             265             270
Lys Asn Pro Gln Leu Arg Asp Leu Asp Ile Phe Leu Ser Ser Val Asp
            275                 280                 285
Ile Asn Glu Gly Ala Leu Leu Leu Pro His Phe Asn Ser Lys Ala Ile
    290                 295                 300
Val Ile Leu Val Ile Asn Glu Gly Asp Ala Asn Ile Glu Leu Val Gly
305                 310                 315                 320
Ile Lys Glu Gln Gln Gln Lys Gln Lys Gln Glu Glu Pro Leu Glu
                325                 330                 335
Val Gln Arg Tyr Arg Ala Glu Leu Ser Glu Asp Asp Ile Ile Val Ile
            340                 345                 350
Pro Ala Ala Tyr Pro Phe Val Val Asn Ala Thr Ser Asn Leu Asn Ile
            355                 360                 365
Ile Ala Ile Gly Ile Asn Ala Glu Asn Asn Gln Arg Asn Phe Leu Ala
            370                 375                 380
Gly Glu Lys Asp Asn Val Val Arg Gln Ile Glu Arg Gln Val Gln Glu
385                 390                 395                 400
Leu Ala Phe Pro Gly Ser Ala Gln Asp Val Glu Arg Leu Leu Lys Lys
                405                 410                 415
Gln Arg Glu Ser Tyr Phe Val Asp Ala Gln Pro Gln Gln Lys Glu Glu
            420                 425                 430
Gly Ser Lys Gly Arg Lys Gly Pro Phe Pro Ser Ile Leu Gly Ala Leu
            435                 440                 445
Tyr
```

<210> SEQ ID NO 94
<211> LENGTH: 3808
<212> TYPE: DNA
<213> ORGANISM: Glycine max

<400> SEQUENCE: 94

```
taggatcctt caatagaaaa tgtgttattt cctcatcacc agacaaaggg gcaacagtta      60
acaaaacaaa tttatgtttc atttgagatt aaggaaggta aggaagaaaa aagattaaaa     120
aaaatgtcct tatctctttg tttctgtaat aataatataa gagacttaaa cttttaatat     180
aataattgta attaggtttt ctagtcatga gcaccactca gagacaagat ttcaagaaaa     240
caattttgtt aaacatctta ttagaaactt ttagttaagt cttgaagtta gaattaaaca     300
aaaaaaatta cacacgagaa acacaataaa cccactaccg tcaggttatc ataaggatga     360
aatgttttga tatcattaaa tataacacac acaaaaatac atctaattat aacaatatat     420
gttatacata tattttttgta aaacttaga gtttttcaaa acattctaat acatgattag     480
agtttataga aatacaaata tttaaaaaat ataatttttaa aaaacattc taaagtcatt     540
cagatcctct cacacctgtg tgatcattta gtcatgtatg tagtacaatc attgtagttc     600
acaacagagt aaaataaata aggataaact agggaatata tataatatat acaattaaat     660
aaaaaaggga aaatcaaatt agaatttttg attccccaca tgacacaact caccatgcac     720
gctgccacct cagctccctc ctctccacac atgtctcatg tcactttcga ctttggcttt     780
ttcactatga cacaactcgc catgcatgtt gccacgtgag ctccttcctc ttcccatgat     840
gacaccactg ggcatgcatg ctgccacctc agctcccacc tcttctcatt atgagcctac     900
tggccatgca cactgccacc tcagcactcc tctcacttcc cattgctacc tgccaaaccg     960
cttctctcca taaatatcta tttaaattta aactaattat ttcatatact ttttgatga   1020
```

```
cgtggatgca ttgccatcgt tgtttaataa ttgttaattt ggagttgaat aataaaatga    1080
aagaaaaaag ttggaaagat tttgcatttg ttgttgtata aatagagaag agagtgatgg    1140
ttaatgcatg aatgcatgat cagatctggt accatgatga gagtgcggtt tcctttgttg    1200
gtgttgctgg gaactgtttt cctggcatca gtttgtgtct cattaaagga ctacaaggac    1260
gacgatgaca agcttaaggt gagagaggat gagaataacc ctttctactt gagaagctct    1320
aacagcttcc aaactctctt tgagaaccaa aacggtcgca ttcgtctcat tcagagattc    1380
aacaaacgct ccccacaact tgagaacctt cgagactacc ggattgtcca gattcagtca    1440
aaacccaaca caatcattct cccccaccat gctgacgccg atttcattat tattattctt    1500
agcgggagag ccataattac cattgtgaac aacgacgaca gagactccta caacattcac    1560
cctggcgatg ccattagaat cccagctgga accacttact atattattaa ccctcacgac    1620
caccagaatc tcaaaataat caaaattgcc atcccgtca acaaacctgg cagatatgat    1680
gatttcttct tatctagcac tcaagcccaa cagtcctact gcaaggctt cagccataat    1740 attctagaga cctccttcca tagcgaattc gaggagataa acagggtttt gttgggagag    1800
gaagaggagc agaggcagca agagggagtg atcgtggaac tctcaaagga acaaattcgg    1860
caactgagca gacgtgccaa atctagttca aggaaaacca tttcctccga agatgaacca    1920
ttcaacttga gaagccgcaa ccccatctat tccaacaact ttggaaagtt ctttgagatc    1980
acccctgaga aaacccaca gcttcgggac ttggatatct tcctcagttc tgtggatatc    2040
aacgaaggag ctcttcttct accacacttc aattcaaagg ccatagtgat actagtgatt    2100
aatgaaggag atgcaaacat tgaaattgtt ggcattaaag aacaacaaca gaagcagaaa    2160
caggaagagg aacctttgga agtgcaaagg tacagagctg aattgtctga agacgatatt    2220
attgtaattc cagcagctta tccatttgtc attaacgcta cctcaaacct caatattatt    2280
gctattggta tcaatgctga gaacaaccag aggaacttcc ttgcaggcga gaaagacaat    2340
gtggtaaggc agatagaaag acaagtgcag gagcttgcgt tccctgggtc tgcacaagat    2400
gttgagaggc tattaaagaa gcagagggaa tcctactttg ttgatgctca gcctcagcag    2460
aaggaggagg ggagtaaggg aagaaagggt ccttttcctt caatcttagg tgctctctac    2520
tgaataacaa gccgaattct gcagaattca ctcccaaaac caccttccct gtgacagtta    2580
aaccctgctt ataccttcc tcctaataat gttcatctgt cacacaaact aaaataaata    2640
aaatgggagc aataaataaa atgggagctc atatatttac accatttaca ctgtctatta    2700
ttcaccatgc caattattac ttcataattt taaaattatg tcattttaa aaattgctta    2760 atgatggaaa ggattattat aagttaaaag tataacatag ataaactaac cacaaaacaa    2820
atcaatataa actaacttac tctcccatct aattttatt taaatttctt tacacttctc    2880
ttccatttct atttctacaa cattatttaa cattttatt gtattttct tactttctaa    2940 ctctattcat ttcaaaaatc aatatatgtt tatcaccacc tctctaaaaa aactttaca    3000 atcattggtc cagaaaagtt aaatcacgag atggtcattt tagcattaaa acaacgattc    3060
ttgtatcact atttttcagc atgtagtcca ttctcttcaa acaagacag cggctatata    3120 atcgttgtgt tatattcagt ctaaaacaat tgttatggta aaagtcgtca ttttacgcct    3180 tttaaaaga tataaaatga caattatggt taaaagtcat catgttagat cctccttaaa    3240
gatataaaat gacagttttg ataaaaagtg gtcattttat acgctcttga agatataaa    3300 acgacggtta tggtaaaagc tgccatttta aatgaaatat ttttgtttta gttcattttg    3360
tttaatgcta atcccatttta aattgacttg tacaattaaa actcacccac ccagatacaa    3420
```

-continued

```
tataaactaa cttactctca cagctaagtt ttatttaaat ttctttacac ttcttttcca      3480
tttctatttc tatgacatta actaacattt ttctcgtaat tttttttctt attttctaac      3540
tctatccatt tcaaatcgat atatgtttat caccaccact ttaaaaagaa aatttacaat      3600
ttctcgtgca aaaaagctaa atcatgaccg tcattttagc attaaaacaa cgattcttgt      3660
atcgttgttt ttcagcatgt agtccattct tttcaagcaa agacaacagc tataatca       3720 tcgtgttata ttcagtctaa aacaacagta atgataaaag tcatcatttt aggcctttct      3780
gaaatatata gaacgacatt catggtaa                                          3808
```

<210> SEQ ID NO 95
<211> LENGTH: 449
<212> TYPE: PRT
<213> ORGANISM: Glycine max

<400> SEQUENCE: 95

```
Met Met Arg Val Arg Phe Pro Leu Leu Val Leu Leu Gly Thr Val Phe
1               5                   10                  15

Leu Ala Ser Val Cys Val Ser Leu Lys Asp Tyr Lys Asp Asp Asp Asp
            20                  25                  30

Lys Leu Lys Val Arg Glu Asp Glu Asn Asn Pro Phe Tyr Leu Arg Ser
        35                  40                  45

Ser Asn Ser Phe Gln Thr Leu Phe Glu Asn Gln Asn Gly Arg Ile Arg
    50                  55                  60

Leu Ile Gln Arg Phe Asn Lys Arg Ser Pro Gln Leu Glu Asn Leu Arg
65                  70                  75                  80

Asp Tyr Arg Ile Val Gln Ile Gln Ser Lys Pro Asn Thr Ile Ile Leu
                85                  90                  95

Pro His His Ala Asp Ala Asp Phe Ile Ile Ile Ile Leu Ser Gly Arg
            100                 105                 110

Ala Ile Ile Thr Ile Val Asn Asn Asp Asp Arg Asp Ser Tyr Asn Ile
        115                 120                 125

His Pro Gly Asp Ala Ile Arg Ile Pro Ala Gly Thr Thr Tyr Tyr Ile
    130                 135                 140

Ile Asn Pro His Asp His Gln Asn Leu Lys Ile Ile Lys Ile Ala Ile
145                 150                 155                 160

Pro Val Asn Lys Pro Gly Arg Tyr Asp Asp Phe Phe Leu Ser Ser Thr
                165                 170                 175

Gln Ala Gln Gln Ser Tyr Leu Gln Gly Phe Ser His Asn Ile Leu Glu
            180                 185                 190

Thr Ser Phe His Ser Glu Phe Glu Glu Ile Asn Arg Val Leu Leu Gly
        195                 200                 205

Glu Glu Glu Glu Gln Arg Gln Gln Glu Gly Val Ile Val Glu Leu Ser
    210                 215                 220

Lys Glu Gln Ile Arg Gln Leu Ser Arg Arg Ala Lys Ser Ser Ser Arg
225                 230                 235                 240

Lys Thr Ile Ser Ser Glu Asp Glu Pro Phe Asn Leu Arg Ser Arg Asn
                245                 250                 255

Pro Ile Tyr Ser Asn Asn Phe Gly Lys Phe Glu Ile Thr Pro Glu
            260                 265                 270

Lys Asn Pro Gln Leu Arg Asp Leu Asp Ile Phe Leu Ser Ser Val Asp
        275                 280                 285

Ile Asn Glu Gly Ala Leu Leu Leu Pro His Phe Asn Ser Lys Ala Ile
    290                 295                 300
```

```
Val Ile Leu Val Ile Asn Glu Gly Asp Ala Asn Ile Glu Ile Val Gly
305                 310                 315                 320

Ile Lys Glu Gln Gln Gln Lys Gln Lys Gln Glu Glu Pro Leu Glu
            325                 330                 335

Val Gln Arg Tyr Arg Ala Glu Leu Ser Glu Asp Asp Ile Ile Val Ile
            340                 345                 350

Pro Ala Ala Tyr Pro Phe Val Ile Asn Ala Thr Ser Asn Leu Asn Ile
            355                 360                 365

Ile Ala Ile Gly Ile Asn Ala Glu Asn Asn Gln Arg Asn Phe Leu Ala
        370                 375                 380

Gly Glu Lys Asp Asn Val Val Arg Gln Ile Glu Arg Gln Val Gln Glu
385                 390                 395                 400

Leu Ala Phe Pro Gly Ser Ala Gln Asp Val Glu Arg Leu Leu Lys Lys
                405                 410                 415

Gln Arg Glu Ser Tyr Phe Val Asp Ala Gln Pro Gln Gln Lys Glu Glu
            420                 425                 430

Gly Ser Lys Gly Arg Lys Gly Pro Phe Pro Ser Ile Leu Gly Ala Leu
        435                 440                 445

Tyr

<210> SEQ ID NO 96
<211> LENGTH: 3808
<212> TYPE: DNA
<213> ORGANISM: Glycine max

<400> SEQUENCE: 96
taggatcctt caatagaaaa tgtgttattt cctcatcacc agacaaaggg gcaacagtta      60
acaaaacaaa tttatgtttc atttgagatt aaggaaggta aggaagaaaa aagattaaaa     120
aaaatgtcct tatctctttg tttctgtaat aataatataa gagacttaaa cttttaatat     180
aataattgta attaggtttt ctagtcatga gcaccactca gagacaagat ttcaagaaaa     240
caattttgtt aaacatctta ttagaaactt ttagttaagt cttgaagtta gaattaaaca     300
aaaaaaatta cacgagaaa acacaataaa cccactaccg tcaggttatc ataaggatga     360
aatgttttga tatcattaaa tataacacac acaaaaatac atctaattat aacaatatat     420
gttatacata tattttgta aaacttaga gtttttcaaa acattctaat acatgattag      480
agtttataga aatacaaata tttaaaaaat ataattttaa aaaaacattc taaagtcatt     540
cagatcctct cacacctgtg tgatcattta gtcatgtatg tagtacaatc attgtagttc     600
acaacagagt aaaataaata aggataaact agggaatata tataatatat acaattaaat     660
aaaaaaggga aaatcaaatt agaattttg attccccaca tgacacaact caccatgcac     720
gctgccacct cagctccctc ctctccacac atgtctcatg tcactttcga ctttggcttt     780
ttcactatga cacaactcgc catgcatgtt gccacgtgag ctccttcctc ttcccatgat     840
gacaccactg ggcatgcatg ctgccacctc agctcccacc tcttctcatt atgagcctac     900
tggccatgca cactgccacc tcagcactcc tctcacttcc cattgctacc tgccaaaccg     960
cttctctcca taaatatcta tttaaattta aactaattat ttcatatact tttttgatga    1020
cgtggatgca ttgccatcgt tgtttaataa ttgttaattt ggagttgaat aataaaatga    1080
aagaaaaaag ttggaaagat tttgcatttg ttgttgtata aatagagaag agagtgatgg    1140
ttaatgcatg aatgcatgat cagatctggt accatgatga gagtgcggtt ccctttgttg    1200
gtgttgctgg gaactgtttt cctggcatca gtttgtgtct cattaaagga ctacaaggac    1260
```

-continued

```
gacgatgaca agcttaaggt gagagaggat gagaataacc ctttctactt gagaagctct      1320
aacagcttcc aaactctctt tgagaaccaa aacggtcgca ttcgtctcat tcagagattc      1380
aacaaacgct ccccacaact tgagaacctt cgagactacc ggattgtcca gattcagtca      1440
aaacccaaca caatcattct cccccaccat gctgacgccg atttcattat tattattctt      1500
agcgggagag ccataattac cattgtgaac aacgacgaca gagactccta caacattcac      1560
cctggcgatg ccattagaat cccagctgga accacttact atattattaa ccctcacgac      1620
caccagaatc tcaaaataat caaaattgcc atacccgtca acaaacctgg cagatatgat      1680
gatttcttct tatctagcac tcaagcccaa cagtcctact tgcaaggctt cagccataat      1740
attctagaga cctccttcca tagcgaattc gaggagataa acagggtttt gttgggagag      1800
gaagaggagc agaggcagca agaggagtg atcgtggaac tctcaaagga acaaattcgg      1860
caactgagca gacgtgccaa atctagttca aggaaaacca tttcctccga agatgaacca      1920
ttcaacttga gaagccgcaa ccccatctat tccaacaact ttggaaagtt ctttgagatc      1980
acccctgaga aaacccaca gcttcgggac ttggatatct tcctcagttc tgtggatatc      2040
aacgaaggag ctcttcttct accacacttc aattcaaagg ccatagtgat actagtgatt      2100
aatgaaggag atgcaaacat tgaaattgtt ggcattaaag aacaacaaca gaagcagaaa      2160
caggaagagg aacctttgga agtgcaaagg tacagagctg aattgtctga agacgatatt      2220
attgtaattc cagcagctta tccatttgtc attaacgcta cctcaaacct caatattatt      2280
gctattggta tcaatgctga gaacaaccag aggaacttcc ttgcaggcga aaagacaat      2340 gtggtaaggc agatagaaag acaagtgcag gagcttgcgt tccctgggtc tgcacaagat      2400
gttgagaggc tattaaagaa gcagagggaa tcctactttg ttgatgctca gcctcagcag      2460
aaggaggagg ggagtaaggg aagaaagggt ccttttcctt caatcttagg tgctctctac      2520
tgaataacaa gccgaattct gcagaattca ctcccaaaac caccttccct gtgacagtta      2580
aaccctgctt atacctttcc tcctaataat gttcatctgt cacacaaact aaaataaata      2640
aaatgggagc aataaataaa atgggagctc atatatttac accatttaca ctgtctatta      2700
ttcaccatgc caattattac ttcataattt taaaattatg tcattttttaa aaattgctta      2760 atgatggaaa ggattattat aagttaaaag tataacatag ataaactaac cacaaaacaa      2820
atcaatataa actaacttac tctcccatct aatttttatt taaatttctt tacacttctc      2880
ttccatttct atttctacaa cattatttaa catttttatt gtattttttct tactttctaa      2940 ctctattcat ttcaaaaatc aatatatgtt tatcaccacc tctctaaaaa aactttaca      3000 atcattggtc cagaaaagtt aaatcacgag atggtcattt tagcattaaa acaacgattc      3060
ttgtatcact attttttcagc atgtagtcca ttctcttcaa acaaagacag cggctatata      3120
atcgttgtgt tatattcagt ctaaaacaat tgttatggta aaagtcgtca ttttacgcct      3180
ttttaaaaga tataaaatga caattatggt taaaagtcat catgttagat cctccttaaa      3240
gatataaaat gacagttttg ataaaaagtg gtcattttat acgctcttga agatatataaa      3300 acgacggtta tggtaaaagc tgccatttta aatgaaatat ttttgtttta gttcattttg      3360
tttaatgcta atcccatttta aattgacttg tacaattaaa actcacccac ccagatacaa      3420
tataaactaa cttactctca cagctaagtt ttatttaaat ttctttacac ttcttttcca      3480
tttctatttc tatgacatta actaacattt ttctcgtaat ttttttttctt atttctaac      3540 tctatccatt tcaaatcgat atatgtttat caccaccact ttaaaaagaa aatttacaat      3600
```

```
ttctcgtgca aaaaagctaa atcatgaccg tcattttagc attaaaacaa cgattcttgt    3660
atcgttgttt ttcagcatgt agtccattct tttcaagcaa agacaacagc tatataatca    3720
tcgtgttata ttcagtctaa aacaacagta atgataaaag tcatcatttt aggcctttct    3780
gaaatatata gaacgacatt catggtaa                                       3808
```

<210> SEQ ID NO 97
<211> LENGTH: 449
<212> TYPE: PRT
<213> ORGANISM: Glycine max

<400> SEQUENCE: 97

```
Met Met Arg Val Arg Phe Pro Leu Leu Val Leu Leu Gly Thr Val Phe
  1               5                  10                  15

Leu Ala Ser Val Cys Val Ser Leu Lys Asp Tyr Lys Asp Asp Asp Asp
             20                  25                  30

Lys Leu Lys Val Arg Glu Asp Glu Asn Asn Pro Phe Tyr Leu Arg Ser
         35                  40                  45

Ser Asn Ser Phe Gln Thr Leu Phe Glu Asn Gln Asn Gly Arg Ile Arg
 50                  55                  60

Leu Ile Gln Arg Phe Asn Lys Arg Ser Pro Gln Leu Glu Asn Leu Arg
 65                  70                  75                  80

Asp Tyr Arg Ile Val Gln Ile Gln Ser Lys Pro Asn Thr Ile Ile Leu
                 85                  90                  95

Pro His His Ala Asp Ala Asp Phe Ile Ile Ile Ile Leu Ser Gly Arg
            100                 105                 110

Ala Ile Ile Thr Ile Val Asn Asn Asp Asp Arg Asp Ser Tyr Asn Ile
        115                 120                 125

His Pro Gly Asp Ala Ile Arg Ile Pro Ala Gly Thr Thr Tyr Tyr Ile
    130                 135                 140

Ile Asn Pro His Asp His Gln Asn Leu Lys Ile Ile Lys Ile Ala Ile
145                 150                 155                 160

Pro Val Asn Lys Pro Gly Arg Tyr Asp Asp Phe Phe Leu Ser Ser Thr
                165                 170                 175

Gln Ala Gln Gln Ser Tyr Leu Gln Gly Phe Ser His Asn Ile Leu Glu
            180                 185                 190

Thr Ser Phe His Ser Glu Phe Glu Glu Ile Asn Arg Val Leu Leu Gly
        195                 200                 205

Glu Glu Glu Glu Gln Arg Gln Gln Glu Gly Val Ile Val Glu Leu Ser
    210                 215                 220

Lys Glu Gln Ile Arg Gln Leu Ser Arg Arg Ala Lys Ser Ser Ser Arg
225                 230                 235                 240

Lys Thr Ile Ser Ser Glu Asp Glu Pro Phe Asn Leu Arg Ser Arg Asn
                245                 250                 255

Pro Ile Tyr Ser Asn Asn Phe Gly Lys Phe Phe Glu Ile Thr Pro Glu
            260                 265                 270

Lys Asn Pro Gln Leu Arg Asp Leu Asp Ile Phe Leu Ser Ser Val Asp
        275                 280                 285

Ile Asn Glu Gly Ala Leu Leu Leu Pro His Phe Asn Ser Lys Ala Ile
    290                 295                 300

Val Ile Leu Val Ile Asn Glu Gly Asp Ala Asn Ile Glu Ile Val Gly
305                 310                 315                 320

Ile Lys Glu Gln Gln Gln Lys Gln Lys Gln Glu Glu Pro Leu Glu
                325                 330                 335
```

-continued

```
Val Gln Arg Tyr Arg Ala Glu Leu Ser Glu Asp Asp Ile Ile Val Ile
            340                 345                 350

Pro Ala Ala Tyr Pro Phe Val Ile Asn Ala Thr Ser Asn Leu Asn Ile
        355                 360                 365

Ile Ala Ile Gly Ile Asn Ala Glu Asn Asn Gln Arg Asn Phe Leu Ala
    370                 375                 380

Gly Glu Lys Asp Asn Val Val Arg Gln Ile Glu Arg Gln Val Gln Glu
385                 390                 395                 400

Leu Ala Phe Pro Gly Ser Ala Gln Asp Val Glu Arg Leu Leu Lys Lys
                405                 410                 415

Gln Arg Glu Ser Tyr Phe Val Asp Ala Gln Pro Gln Gln Lys Glu Glu
            420                 425                 430

Gly Ser Lys Gly Arg Lys Gly Pro Phe Pro Ser Ile Leu Gly Ala Leu
        435                 440                 445

Tyr
```

ENHANCED PROTEINS AND METHODS FOR THEIR USE

The application claims the benefits of and priority to U.S. Provisional Application No. 60/322,461, filed Sep. 17, 2001. The content of the foregoing application is herein incorporated by reference in its entirety.

The present invention generally relates to the field of plant genetics and protein biochemistry. More specifically, the present invention relates to the field of modified proteins having an increased number of essential amino acids.

A full complement of amino acids is nutritionally important for all animals, including humans, and is often important to produce high quality livestock and animal products. However a typical animal diet can be deficient in one or more amino acids that the particular animal is unable to synthesize itself. Accordingly, essential amino acids are required by all animals for normal growth and development. Amino acid requirements vary from one animal species to the next. Typical essential amino acids include threonine, isoleucine, tryptophan, valine, arginine, lysine, methionine, and histidine.

Addition of essential amino acids to the diet of livestock can increase the commercial value of animals. The availability and absorption of sufficient nutrients is critical to an animal's production of commercially important products. The addition of essential amino acids to the diets of humans can prevent certain diseases caused by malnutrition or protein deficiency and promote normal growth and development.

Attempts have been made to modify animal diets to increase the amount of essential amino acids in the animal feed and human food (hereafter collectively referred to as food). For example, food is often supplemented with additional protein.

Genetic engineering techniques provide a more efficient approach to creating enhanced food containing increased amounts of essential amino acids. For example, essential amino acids may be substituted into a food protein in place of non-essential amino acids, thus increasing the nutritive value of that protein in the food. Furthermore, such an enhanced protein may be constitutively expressed in plants or seeds that are incorporated into food. Consequently, the enhanced protein will be present at relatively high levels in the food, providing significant nutritive improvement to an animal's diet, for example.

Clearly there exists a need in the art for enhanced proteins that contain an increased amount of essential amino acids. Such proteins would significantly improve the nutritive value of animal feed, leading to improved quality and quantity of commercial animal products. Such proteins would also significantly improve the nutritive value of human food, leading to a decreased incidence of malnutrition and associated health problems and improving the overall growth and development of infants and children.

SUMMARY OF THE INVENTION

The present invention includes and provides a modified polypeptide comprising a substitution of 1 or more essential amino acids selected from the group consisting of isoleucine and tryptophan into an unmodified polypeptide having an amino acid sequence of SEQ ID NO: 1, wherein the modified polypeptide is capable of accumulating in a seed.

The present invention includes and provides a modified polypeptide comprising a substitution of 1 or more essential amino acids selected from the group consisting of threonine, isoleucine, tryptophan, valine, arginine, lysine, methionine, and histidine into the unmodified amino acid sequence of SEQ ID NO: 1, wherein the modified polypeptide is capable of accumulating in a seed.

The present invention includes and provides a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed.

The present invention includes and provides a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a cell.

The present invention includes and provides a cell containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed.

The present invention includes and provides a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of forming trimers.

The present invention includes and provides a seed from a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed, and wherein the plant is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius*, Southern pine, soybean, spinach, strawberry, sugarbeet, sugarcane, sunflower, Sweetgum, tea, tobacco, tomato, turf, or wheat plant.

The present invention includes and provides a plant from a seed from a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of forming trimers, and wherein the transgenic plant is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius*, Southern pine, soybean, spinach, strawberry, sugarbeet, sugarcane, sunflower, Sweetgum, tea, tobacco, tomato, turf, or wheat plant.

The present invention includes and provides animal feed comprising a seed from a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed, and wherein the plant is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius,* Southern pine, soybean, spinach, strawberry, sugarbeet, sugarcane, sunflower, Sweetgum, tea, tobacco, tomato, turf, or wheat plant.

The present invention includes and provides animal feed comprising a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed, and wherein the plant is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius,* Southern pine, soybean, spinach, strawberry, sugarbeet, sugarcane, sunflower, Sweetgum, tea, tobacco, tomato, turf, or wheat plant.

The present invention includes and provides animal feed comprising a plant from a seed from a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed, and wherein the transgenic plant is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius*, Southern pine, soybean, spinach, strawberry, sugarbeet, sugarcane, sunflower, Sweetgum, tea, tobacco, tomato, turf, or wheat plant.

The present invention includes and provides human food comprising a seed from a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed, and wherein the plant is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius,* Southern pine, soybean, spinach, strawberry, sugarbeet, sugarcane, sunflower, Sweetgum, tea, tobacco, tomato, turf, or wheat plant.

The present invention includes and provides human food comprising a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed, and wherein the plant is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius*, Southern pine, soybean, spinach, strawberry, sugarbeet, sugarcane, sunflower, Sweetgum, tea, tobacco, tomato, turf, or wheat plant.

The present invention includes and provides human food comprising a plant from a seed from a transgenic plant containing, in the 5' to 3' direction, a heterologous promoter operably linked to a recombinant nucleic acid molecule encoding a modified β-conglycinin polypeptide comprising a substitution of 1 or more essential amino acids selected from the group consisting of threonine, isoleucine, tryptophan, valine, arginine, lysine, methionine, and histidine into an unmodified β-conglycinin polypeptide having an amino acid sequence of SEQ ID NO: 1, wherein the modified β-conglycinin polypeptide is capable of accumulating in a seed, and wherein the transgenic plant is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius*, Southern pine, soybean, spinach, strawberry, sugarbeet, sugarcane, sunflower, Sweetgum, tea, tobacco, tomato, turf, or wheat plant.

BRIEF DESCRIPTION OF THE SEQUENCES

Figure 1:
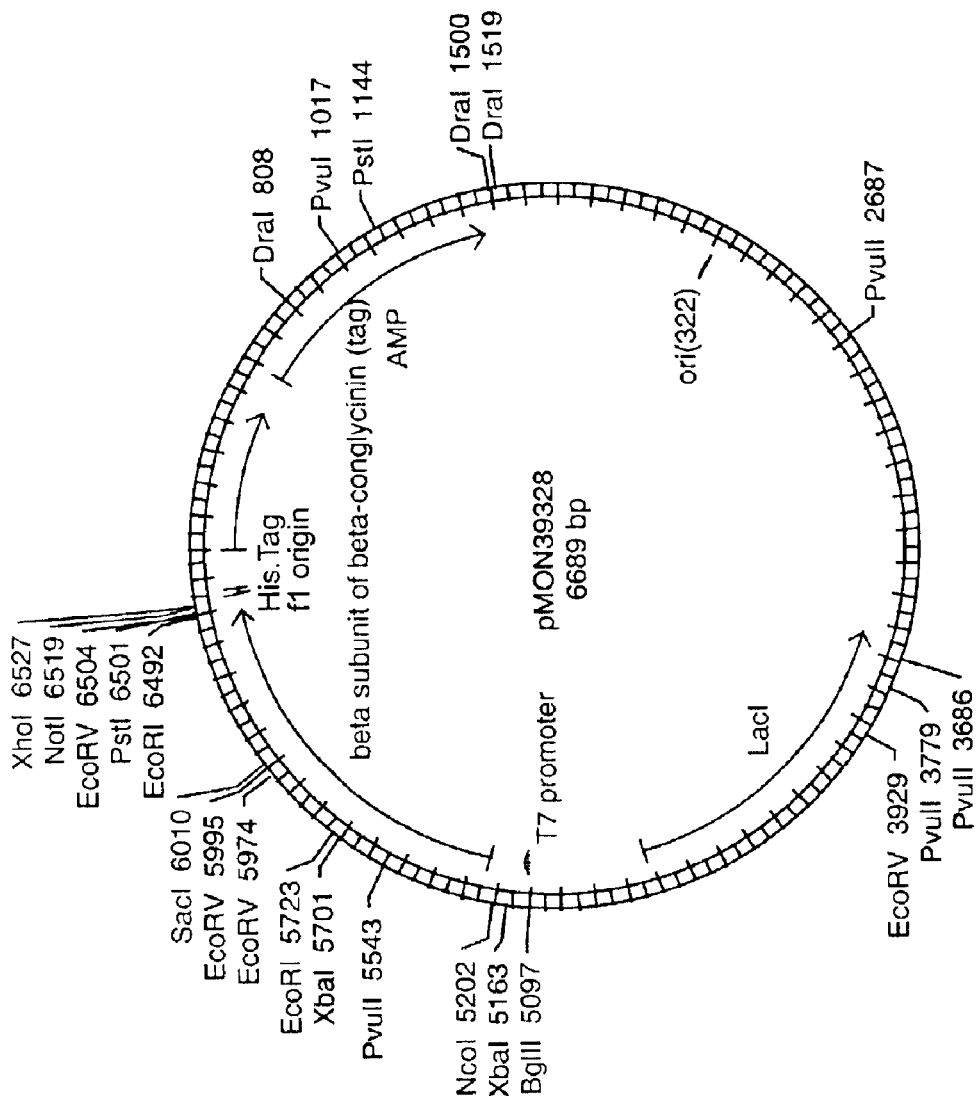
FIG. 1 is a map of pMON39328.

SEQ ID NO: 1 is a wild-type Glycine max 7S-beta-conglycinin β subunit pre-protein amino acid sequence.

SEQ ID NO: 2 is a wild-type Glycine max 7S-beta-conglycinin β subunit pre-protein as in SEQ ID NO: 1 with residues 1–25 and 416–439 not shown.

SEQ ID NO: 3 is a wild-type Glycine max 7S-beta-conglycinin β subunit cDNA sequence.

SEQ ID NO: 4 is an oligonucleotide primer.
SEQ ID NO: 5 is an oligonucleotide primer.
SEQ ID NO: 6 is an oligonucleotide primer.
SEQ ID NO: 7 is an oligonucleotide primer.
SEQ ID NO: 8 is a DNA sequence encoding a FLAG epitope.
SEQ ID NO: 9 is a FLAG amino acid epitope sequence.
SEQ ID NO: 10 is an oligonucleotide primer.
SEQ ID NO: 11 is an oligonucleotide primer.
SEQ ID NO: 12 is an amino acid sequence of the epitope (FLAG)-tagged form of the β-conglycinin β subunit encoded by pMON39328.

SEQ ID NO: 13 is the nucleotide sequence in pMON39328 encoding the epitope (FLAG)-tagged form of the β-conglycinin 1 subunit.

SEQ ID NO: 14 is the mature form of the amino acid sequence (plus additional methionine encoded by start codon) of the β-conglycinin β subunit encoded by pMON39329 without a FLAG epitope.

SEQ ID NO: 15 is the nucleotide sequence in pMON39329 encoding the mature form of the β-conglycinin β subunit without a FLAG epitope.

SEQ ID NOs: 16–83 are oligonucleotide primer sequences.

SEQ ID NO: 84 is the coding sequence for the mutant designated as 39335-14.

SEQ ID NO: 85 is the coding sequence for the mutant designated as 39335-41.

SEQ ID NO: 86 is the coding sequence for the mutant designated as 39335-58.

SEQ ID NO: 87 is the coding sequence for the mutant designated as 39335-78.

SEQ ID NO: 88 is the nucleotide sequence in pMON69616.

SEQ ID NO: 89 is the amino acid sequence of pMON69616.

SEQ ID NO: 90 is the nucleotide sequence in pMON64016.

SEQ ID NO: 91 is the amino acid sequence of pMON64016.

SEQ ID NO: 92 is the nucleotide sequence in pMON64015.

SEQ ID NO: 93 is the amino acid sequence of pMON64015.

SEQ ID NO: 94 is the nucleotide sequence in pMON64019.

SEQ ID NO: 95 is the amino acid sequence of pMON019.

SEQ ID NO: 96 is the nucleotide sequence in pMON69621.

SEQ ID NO: 97 is the amino acid sequence of pMON69621.

Definitions

The following definitions are provided as an aid to understanding the detailed description of the present invention.

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. "Percent identity" is the identity fraction times 100.

"Essential amino acids" are, for a given organism, amino acids that the organism itself is unable to synthesize and which the organism therefore must obtain through the organism's diet. Essential amino acids vary among different animals depending on the animal species, and may include one or more of the group of amino acids threonine, isoleucine, tryptophan, valine, arginine, lysine, methionine, histidine, leucine, and phenylalanine.

"Antigenic epitope" refers to any discrete segment of a molecule, protein, or nucleic acid capable of eliciting an immune response, where the immune response results in the production of antibodies reactive with the antigenic epitope.

The phrases "coding sequence," "open reading frame," "structural sequence," and "structural nucleic acid sequence" refer to a physical structure comprising an orderly arrangement of nucleic acids. The nucleic acids are arranged in a series of nucleic acid triplets that each form a codon. Each codon encodes for a specific amino acid. Thus the coding sequence, structural sequence, and structural nucleic acid sequence encode a series of amino acids forming a protein, polypeptide, or peptide sequence. The coding sequence, structural sequence, and structural nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The phrases "DNA sequence," "nucleic acid sequence," and "nucleic acid molecule" refer to a physical structure comprising an orderly arrangement of nucleic acids. The DNA sequence or nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The term "expression of antisense RNA" refers to the transcription of a DNA to produce a first RNA molecule capable of hybridizing to a second RNA molecule.

The term "gene" refers to chromosomal DNA, plasmid DNA, cDNA, synthetic DNA, or other DNA that encodes a peptide, polypeptide, protein, or RNA molecule.

"Homology" refers to the level of similarity between two or more nucleic acid or amino acid sequences in terms of percent of positional identity (i.e., sequence similarity or identity).

The phrase "heterologous" refers to the relationship between two or more nucleic acid or protein sequences that are derived from different sources. For example, a promoter is heterologous with respect to a coding sequence if such a combination is not normally found in nature. In addition, a particular sequence may be "heterologous" with respect to a cell or organism into which it is inserted (i.e., does not naturally occur in that particular cell or organism).

"Hybridization" refers to the ability of a strand of nucleic acid to join with a complementary strand via base pairing. Hybridization occurs when complementary nucleic acid sequences in the two nucleic acid strands contact one another under appropriate conditions.

"Nucleic acid" refers to deoxyribonucleic acid (DNA) and ribonucleic acid (RNA).

"Phenotype" refers to traits exhibited by an organism resulting from the interaction of genotype and environment.

"Polyadenylation signal" or "polyA signal" refers to a nucleic acid sequence located 3' to a coding region that promotes the addition of adenylate nucleotides to the 3' end of the mRNA transcribed from the coding region.

The phrase "operably linked" refers to the functional spatial arrangement of two or more nucleic acid regions or nucleic acid sequences. For example, a promoter region may be positioned relative to a nucleic acid sequence such that transcription of the nucleic acid sequence is directed by the promoter region. Thus, a promoter region is "operably linked" to the nucleic acid sequence.

The term "promoter" or "promoter region" refers to a nucleic acid sequence, usually found upstream (5') to a coding sequence, that directs transcription of the nucleic acid sequence into mRNA. The promoter or promoter region typically provide a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

The terms "recombinant nucleic acid vector" and "recombinant vector" refer to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source, is capable of genomic integration or autonomous replication, and comprises a promoter nucleic acid sequence operably linked to one or more nucleic acid sequences. A recombinant vector is typically used to introduce such operably linked sequences into a suitable host.

"Regeneration" refers to the process of growing a plant from a plant cell or plant tissue (e.g., plant protoplast or explant).

"Selectable marker" refers to a nucleic acid sequence whose expression confers a phenotype facilitating identification of cells containing the nucleic acid sequence. Selectable markers include those which confer resistance to toxic chemicals (e.g., ampicillin resistance, kanamycin resistance), complement a nutritional deficiency (e.g., uracil, histidine, leucine), or impart a visually distinguishing characteristic (e.g., color changes or fluorescence).

"Transcription" refers to the process of producing an RNA copy from a DNA template.

"Transgenic" refers to organisms into which exogenous nucleic acid sequences are integrated.

"Vector" refers to a plasmid, cosmid, bacteriophage, or virus that carries exogenous DNA into a host organism.

"Regulatory sequence" refers to a nucleotide sequence located upstream (5'), within, or downstream (3') to a coding sequence. Transcription and expression of the coding sequence is typically impacted by the presence or absence of the regulatory sequence.

The term "substantially homologous" refers to two sequences which are at least 90% identical in sequence, as measured by the BestFit program described herein (Version 10; Genetics Computer Group, Inc., University of Wisconsin Biotechnology Center, Madison, Wis.), using default parameters.

The term "transformation" refers to the introduction of nucleic acid into a recipient host. The term "host" refers to bacteria cells, fungi, animals or animal cells, plants or seeds, or any plant parts or tissues including protoplasts, calli, roots, tubers, seeds, stems, leaves, seedlings, embryos, and pollen.

As used herein, the term "transgenic plant" refers to a plant where an introduced nucleic acid is stably introduced into a genome of the plant, for example, the nuclear or plastid genomes.

As used herein, the term "substantially purified" refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

DETAILED DESCRIPTION OF THE PREFERRED EMBODIMENTS

The present invention includes and provides modified polypeptides having increased levels of essential amino acids, and methods for their use, design, and production. The modified polypeptides are characterized by improved nutritional content relative to the unmodified polypeptide from which they are engineered.

Polypeptide Sequences

The present invention includes and provides a modified polypeptide having increased levels of essential amino acids. The modified polypeptide is characterized in having improved nutritional content relative to the unmodified polypeptide. The modified polypeptide generally comprises an addition or substitution of at least one essential amino acid into the amino acid sequence of the unmodified polypeptide. Such essential amino acids are preferably selected from the group consisting of threonine, isoleucine, tryptophan, valine, arginine, lysine, methionine, and histidine. In a preferred embodiment, the modified polypeptide generally comprises a substitution of at least one essential amino acid into the amino acid sequence of the unmodified polypeptide. In a more preferred embodiment, the modified polypeptide generally comprises a substitution of at least one tryptophan or isoleucine residue in the amino acid sequence of the unmodified polypeptide.

As used herein, a "substitution" of an amino acid means the replacement of an amino acid in a protein with a different amino acid. A "substitution" does not therefore change the total number of amino acids in the modified protein. In a preferred embodiment, the modified polypeptide is capable of accumulating in a cell. In another preferred embodiment, the modified polypeptide is capable of accumulating in a seed. As used herein, "accumulates in a seed" or "cell" means the polypeptide is generated and maintained at a rate greater than the rate of degradation in the seed or cell. In yet another preferred embodiment, the modified polypeptide is capable of forming trimers. As used herein, a protein is "capable of forming trimers" when the protein is able to self-assemble and trimerize when translated in a cellular environment. In a preferred embodiment, the level of trimerization of the modified polypeptide is 10% of the level of trimerization of the unmodified polypeptide, and more preferably 20, 30, 40, 50, 60, 70, 80, 90, 95, and 99% of the level of trimerization of the unmodified polypeptide as determined in Example 6, below.

The modified polypeptide may generally be any polypeptide that is suitable for incorporation into the diet of an animal. The polypeptide is preferably selected from the group of polypeptides that are expressed at relatively high concentrations in a given plant tissue, such as seed storage proteins, vegetative storage proteins, enzymes, or structural proteins. The modified polypeptide is more preferably a modified β-conglycinin, glycinin, 7S storage globulin, 11S storage globulin, albumin, prolamin, arcelin, or leghemoglobin polypeptide.

In one embodiment of the present invention, the modified polypeptide has lysine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has methionine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has threonine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has valine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has arginine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has histidine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In a preferred embodiment of the present invention, the modified polypeptide has tryptophan residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In a preferred embodiment of the present invention, the modified polypeptide has isoleucine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In a more preferred aspect, the modified polypeptide is a β-conglycinin polypeptide (SEQ ID NO: 1) having the essential amino acid tryptophan substituted in place of at least 1, and more preferably in place of at least 2, 3, 4, 5, 6, 7, 8, 9, 10, 11, 12, 13, 14, 15, 16, 17, 18, 19, 20, 21, or 22 of the amino acids selected from the group consisting of N32; Y35; N40; N50; Y72; H88; Y116; H119; Y132; Y133; P137; Y158; Y172; E200; P239; Y249; P265; P324; Y330; Y346; N368; and Y411, with respect to the unmodified β-conglycinin sequence (SEQ ID NO: 1, as shown without termini as SEQ ID NO: 2).

The modified polypeptide is preferably a β-conglycinin polypeptide (SEQ ID NO: 1) having the essential amino acid isoleucine substituted in place of at least two, and more preferably in place of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74, 75, 76, 77, 78, 79, 80, 81, 82, 83, or 84 of the amino acids selected from the group consisting of N32; L36; F46; G51; L56; F59; Q65; L66; Y72; R73; V75; Q76; L85; H88; F94; L95; L96; F97; V98; L99; R102; L105; L107; N17; L118; D121; Q124; R125; P127; Y132; Y133; L134; V135; P137; L143; K147; L148; P151; Y158; F162; Q169; L173; L181; V209; P239; F240; P247; F256; E258; T264; P265; L267; F273; L274; L285; L286; H288; N290; V295; L297; V298; N300; L308; V309; K317; K319; P324; L334; V339; F340; Y341; Y346; F348; Y350; L356; F358; L359; F361; N368; F372; F393; Y411; F412; and V413, with respect to the unmodified β-conglycinin sequence (SEQ ID NO: 1, as shown without termini as SEQ ID NO: 2).

In a preferred embodiment, the modified polypeptide is further modified to have an increased content of at least one, and more preferably 2, 3, or 4 of the essential amino acids selected from the group consisting of histidine, lysine, methionine, and phenylalanine. Other amino acid substitutions may also be made, as needed, for structural and nutritive enhancement of the polypeptide.

In another preferred embodiment of the present invention, the modified polypeptide has the essential amino acid tryptophan substituted in place of at least 1, and more preferably in place of at least 2, 3, 4, 5, 6, 7, 8, 9, 10, 11, 12, 13, 14, 15, 16, 17, 18, 19, 20, 21, or 22 of the amino acids selected from the group consisting of N32; Y35; N40; N50; Y72; H88; Y116; H119; Y132; Y133; P137; Y158; Y172; E200; P239; Y249; P265; P324; Y330; Y346; N368; and Y411 and the essential amino acid isoleucine substituted in place of at least 1 and preferably in place of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74, 75, 76, 77, 78, 79, 80, 81, 82, 83, or 84 of the amino acids selected from the group consisting of N32; L36; F46; G51; L56; F59; Q65; L66; Y72; R73; V75; Q76; L85; H88; F94; L95; L96; F97; V98; L99; R102; L105; L107; N117; L118; D121; Q124; R125; P127; Y132; Y133; L134; V135; P137; L143; K147; L148; P151; Y158; F162; Q169; L173; L181; V209; P239; F240; P247; F256; E258; T264; P265; L267; F273; L274; L285; L286; H288; N290; V295; L297; V298; N300; L308; V309; K317; K319; P324; L334; V339; F340; V341; Y346; F348; V350; L356; F358; L359; F361; N368; F372; F393; Y411; F412; and V413 with respect to the unmodified β-conglycinin sequence.

In a preferred aspect, the modified β-conglycinin polypeptide includes one or more essential amino acid substitutions relative to the unmodified β-conglycinin polypeptide. In an even more preferred aspect, the modified β-conglycinin polypeptide includes two or more essential amino acid substitutions, where the essential amino acids are both tryptophan and isoleucine. In a preferred aspect, the modified polypeptide has at least 1, more preferably 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106 tryptophan or isoleucine substitutions, in any combination, where the tryptophan substitutions are one or more of N32; Y35; N40; N50; Y72; H88; Y116; H119; Y132; Y133; P137; Y158; Y172; E200; P239; Y249; P265; P324; Y330; Y346; N368; and Y411, and the isoleucine substitutions are one or more of N32; L36; F46; G51; L56; F59; Q65; L66; Y72; R73; V75; Q76; L85; H88; F94; L95; L96; F97; V98; L99; R102; L105; L107; N117; L118; D121; Q124; R125; P127; Y132; Y133; L134; V135; P137; L143; K147; L148; P151; Y158; F162; Q169; L173; L181; V209; P239; F240; P247; F256; E258; T264; P265; L267; F273; L274; L285; L286; H288; N290; V295; L297; V298; N300; L308; V309; K317; K319; P324; L334; V339; F340; V341; Y346; F348; V350; L356; F358; L359; F361; N368; F372; F393; Y411; F412; and V413.

The modified polypeptide may be further modified to provide additional desirable features. For example the modified polypeptide may be further modified to increase the content of other essential amino acids, enhance translation of the amino acid sequence, alter post-translational modifications (e.g., phosphorylation or glycosylation sites), transport the polypeptide to a compartment inside or outside of the cell, insert or delete cell signaling motifs, etc.

In another embodiment of the present invention, the modified polypeptide has one or more, two or more, or three or more of the amino acid residues selected from the group consisting of isoleucine, lysine, methionine, threonine, tryptophan, valine, arginine, and histidine, substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, about 30, about 35, about 40, about 45, or about 50 amino acids relative to the unmodified polypeptide.

In a preferred embodiment, a modified protein comprises greater than a 0.25%, greater than a 0.5%, greater than a 1%, greater than a 2%, greater than a 3%, greater than a 5%, greater than a 7%, greater than a 10%, greater than a 15%, or greater than a 20% (weight per weight) increase of threonine, isoleucine, tryptophan, valine, or arginine, or any combination thereof, relative to the unmodified polypeptide.

In a preferred embodiment, a modified β-conglycinin polypeptide comprises greater than a 0.25%, greater than a 0.5%, greater than a 1%, greater than a 2%, greater than a 3%, greater than a 5%, greater than a 7%, greater than a 10%, greater than a 15%, or greater than a 20% (weight per weight) increase of threonine, isoleucine, tryptophan, valine, or arginine, or any combination thereof, relative to the unmodified β-conglycinin polypeptide.

Nucleic Acid Molecules

The present invention includes and provides a recombinant nucleic acid molecule encoding a modified polypeptide of the present invention having increased levels of essential amino acids.

Nucleic acid hybridization is a technique well known to those of skill in the art of DNA manipulation. The hybridization properties of a given pair of nucleic acids is an indication of their similarity or identity.

The nucleic acid molecules preferably hybridize, under low, moderate, or high stringency conditions, with any of the nucleic acid sequences of the present invention.

The hybridization conditions typically involve nucleic acid hybridization in about 0.1× to about 10×SSC (diluted from a 20×SSC stock solution containing 3 M sodium chloride and 0.3 M sodium citrate, pH 7.0 in distilled water), about 2.5× to about 5× Denhardt's solution (diluted from a 50×stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 20° C. to about 70° C. for several hours to overnight. The hybridization conditions are preferably provided by 6×SSC, 5× Denhardt's solution, 100 mg/mL fish sperm DNA, and 0.1% (w/v) SDS, with an incubation at 55° C. for several hours.

The hybridization is generally followed by several wash steps. The wash compositions generally comprise 0.1× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Low stringency conditions may be used to select nucleic acid sequences with lower sequence identities to a target nucleic acid sequence. One may wish to employ conditions such as about 6.0×SSC to about 10×SSC, at temperatures ranging from about 20° C. to about 55° C., and preferably a nucleic acid molecule will hybridize to one or more nucleic acid molecules of the present invention under low stringency conditions of about 6.0×SSC and about 45° C. In a preferred embodiment, a nucleic acid molecule will hybridize to one or more nucleic acid molecules of the present invention under moderately stringent conditions, for example at about 2.0×SSC and about 65° C. In a particularly preferred embodiment, a nucleic acid molecule of the present invention will hybridize to one or more of the above-described nucleic acid molecules under high stringency conditions such as 0.2×SSC and about 65° C.

A nucleic acid sequence of the present invention preferably hybridizes with a complementary nucleic acid sequence encoding any of the polypeptides described herein, the complement thereof, or any fragments thereof.

A nucleic acid sequence of the present invention preferably hybridizes under low stringency conditions with a complementary nucleic acid sequence encoding any of the polypeptides described herein, the complement thereof, or any fragments thereof.

A nucleic acid sequence of the present invention preferably hybridizes under high stringency conditions with a complementary nucleic acid sequence encoding any of the polypeptides described herein, the complement thereof, or any fragments thereof.

The percent of sequence identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, 1981; Smith et al., 1983). The percent identity is most preferably determined using the "Best Fit" program using default parameters.

In an embodiment, the fragments are between 3000 and 1000 consecutive nucleotides, 1800 and 150 consecutive nucleotides, 1500 and 500 consecutive nucleotides, 1300 and 250 consecutive nucleotides, 1000 and 200 consecutive nucleotides, 800 and 150 consecutive nucleotides, 500 and 100 consecutive nucleotides, 300 and 75 consecutive nucleotides, 100 and 50 consecutive nucleotides, 50 and 25 consecutive nucleotides, or 20 and 10 consecutive nucleotides long of a nucleic molecule of the present invention.

In another embodiment, the fragment comprises at least 20, 30, 40 or 50 consecutive nucleotides of a nucleic acid sequence of the present invention.

Promoters

In a preferred embodiment any of the disclosed nucleic acid molecules may be operably linked to a promoter. In a particularly preferred embodiment, the promoter is selected from the group consisting of an 11S glycinin promoter, a USP Vicia faba promoter, and a 7Sα promoter. In another embodiment, the promoter is tissue specific, and preferably seed specific.

In one aspect, a promoter is considered tissue or organ specific if the level of an mRNA in that tissue or organ is expressed at a level that is at least 10 fold higher, preferably at least 100 fold higher or at least 1,000 fold higher than another tissue or organ. The level of mRNA can be measured either at a single time point or at multiple time points and as such the fold increase can be average fold increase or an extrapolated value derived from experimentally measured values. As it is a comparison of levels, any method that measures mRNA levels can be used. In a preferred aspect, the tissue or organs compared are a seed or seed tissue with a leaf or leaf tissue. In another preferred aspect, multiple tissues or organs are compared. A preferred multiple comparison is a seed or seed tissue compared with two, three, four or more tissues or organs selected from the group consisting of floral tissue, floral apex, pollen, leaf, embryo, shoot, leaf primodia, shoot apex, root, root tip, vascular tissue and cotyledon. As used herein, examples of plant organs are seed, leaf, root, etc. and examples of tissues are leaf primodia, shoot apex, vascular tissue, etc.

The activity or strength of a promoter may be measured in terms of the amount of mRNA or protein accumulation it specifically produces, relative to the total amount of mRNA or protein. The promoter preferably expresses an operably linked nucleic acid sequence at a level greater than 2.5%; more preferably greater than 5, 6, 7, 8, or 9%; even more preferably greater than 10, 11, 12, 13, 14, 15, 16, 17, 18, or 19%; and most preferably greater than 20% of the total mRNA.

Alternatively, the activity or strength of a promoter may be expressed relative to a well-characterized promoter (for which transcriptional activity was previously assessed). For example, a promoter of interest may be operably linked to a reporter sequence (e.g., GUS) and introduced into a specific cell type. A known promoter may be similarly prepared and introduced into the same cellular context. Transcriptional activity of the promoter of interest is then determined by comparing the amount of reporter expression, relative to the known promoter. The cellular context is preferably soybean.

Modified Structural Nucleic Acid Sequences

The nucleic acids of the present invention may also be operably linked to a modified structural nucleic acid sequence that is heterologous with respect to the nucleic acids of the present invention. The structural nucleic acid sequence may be modified to provide various desirable features. For example, a structural nucleic acid sequence may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

Codon Usage in Nucleic Acid Sequences

Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the above described nucleic acid and amino acid sequences may be modified to reflect the preferred codon usage of a host cell or organism in which they are contained. Modification of a structural nucleic acid sequence for optimal codon usage in plants is described in U.S. Pat. No. 5,689,052.

Other Modifications of Structural Nucleic Acid Sequences

Additional variations in the structural nucleic acid sequences described above may encode proteins having equivalent or superior characteristics when compared to the proteins from which they are engineered. Mutations may include deletions, insertions, truncations, substitutions, fusions, shuffling of motif sequences, and the like.

Mutations to a structural nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a structural nucleic acid sequence. Examples include single strand rescue (Kunkel et al., 1985), unique site elimination (Deng and Nickloff, 1992), nick protection (Vandeyar et al., 1988), and PCR (Costa et al., 1996). Random or non-specific mutations may be generated by chemical agents (for a general review, see Singer and Kusmierek, 1982) such as nitrosoguanidine (Cerda-Olmedo et al., 1968; Guerola et al, 1971) and 2-aminopurine (Rogan and Bessman, 1970); or by biological methods such as passage through mutator strains (Greener et al., 1997).

Modifications to a nucleic acid sequence may or may not result in changes in the amino acid sequence. Changes that, because of the degeneracy of the genetic code, do not affect the amino acid encoded by the changed codon can occur. In a preferred embodiment, the nucleic acid encoding the modified protein has between 5 and 500 of these changes, more preferably between 10 and 300 changes, even more preferably between 25 and 150 changes, and most preferably between 1 and 25 changes. In a further preferred embodiment, nucleic acid molecules of the present invention include nucleic acid molecules that have 80, 85, 90, 95 or 99% sequence identity with nucleic acid molecules modified in this way. In a further preferred embodiment, nucleic acid molecules of the present invention include nucleic acid molecules that hybridize to nucleic acid molecules modified in this way, as well as nucleic acid molecules that hybridize under low or high stringency conditions to nucleic acid molecules modified in this way.

A second type of change includes additions, deletions, and substitutions in the nucleic acid sequence which result in an altered amino acid sequence. In a preferred embodiment, the nucleic acid encoding the modified protein has between 5 and 500 of these nucleic acid changes, more preferably between 10 and 300 changes, even more preferably between 25 and 150 changes, and most preferably between 1 and 25 of these changes. In a further preferred embodiment, nucleic acid molecules of the present invention include nucleic acid molecules that have 80, 85, 90, 95 or 99% sequence identity with nucleic acid molecules modified in this way. In a further preferred embodiment, nucleic acid molecules of the present invention include nucleic acid molecules that hybridize to nucleic acid molecules modified in this way, as well as nucleic acid molecules that hybridize under low or high stringency conditions to nucleic acid molecules modified in this way.

Additional methods of making the alterations described above are described by Ausubel et al. (1995); Bauer et al. (1985); Craik (1985); Frits Eckstein et al. (1982); Sambrook et al. (1989); Smith et al. (1981); and Osuna et al. (1994).

Modifications may be made to the protein sequences described herein and the nucleic acid sequences which encode them that maintain the desired properties of the molecule. The following is a discussion based upon changing the amino acid sequence of a protein to create an equivalent, or possibly an improved, second-generation molecule. The amino acid changes may be achieved by changing the codons of the structural nucleic acid sequence, according to the codons given in Table 1.

TABLE 1

Codon degeneracy of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |

TABLE 1-continued

Codon degeneracy of amino acids

| Amino acid | One letter | Three letter | Codons |
|---|---|---|---|
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciable loss of the desired activity. It is thus contemplated that various changes may be made in the peptide sequences of the disclosed protein sequences, or their corresponding nucleic acid sequences without appreciable loss of the biological activity. In making such changes, the hydropathic index of amino acids may be considered.

The importance of the hydropathic amino acid index in conferring interactive biological function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics. These are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp, issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0+1); serine (+0.3); asparagine/glutamine (+0.2); glycine (0); threonine (−0.4); proline (−0.5+1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted proteins have improved rumen resistance, increased resistance to proteolytic degradation, or both improved rumen resistance and increased resistance to proteolytic degradation, relative to the unmodified polypeptide from which they are engineered.

Recombinant Vectors

Any of the promoters and structural nucleic acid sequences described above may be provided in a recombinant vector. A recombinant vector typically comprises, in a 5' to 3' orientation: a promoter to direct the transcription of a structural nucleic acid sequence and a structural nucleic acid sequence. Suitable promoters and structural nucleic acid sequences are described herein. The recombinant vector may further comprise a 3' transcriptional terminator, a 3' polyadenylation signal, other untranslated nucleic acid sequences, transit and targeting nucleic acid sequences, selectable markers, enhancers, and operators, as desired.

Means for preparing recombinant vectors are well known in the art. Methods for making recombinant vectors particularly suited to plant transformation are described in U.S. Pat. Nos. 4,971,908; 4,940,835; 4,769,061 and 4,757,011. These types of vectors have also been reviewed (Rodriguez et al., 1988; Glick et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaMVCN transfer control vector, have also been described (Fromm et al., 1985).

Additional Promoters in the Recombinant Vector

One or more additional promoters may also be provided in the recombinant vector. These promoters may be operably linked, for example, without limitation, to any of the structural nucleic acid sequences described above. Alternatively, the promoters may be operably linked to other nucleic acid sequences, such as those encoding transit peptides, selectable marker proteins, or antisense sequences.

These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity. In plants, promoters that are inducible, of viral or synthetic origin, constitutively active, temporally regulated, and spatially regulated have been described (Poszkowski et al., 1989; Odell et al., 1985; Chau et al., 1989).

Often-used constitutive promoters include the CaMV 35S promoter (Odell et al., 1985), the enhanced CaMV 35S promoter, the Figwort Mosaic Virus (FMV) promoter (Richins et al., 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1; Williams et al, 1992), induced by application of safeners (substituted benzenesulfonamide herbicides; Hershey and Stoner, 1991), heat-shock promoters (Ou-Lee et al., 1986; Ainley et al., 1990), a nitrate-inducible promoter derived from the spinach nitrite reductase structural nucleic acid sequence (Back et al., 1991), hormone-inducible promoters (Yamaguchi-Shinozaki et al., 1990; Kares et al., 1990), and light-inducible promoters associated with the small subunit of RuBP carboxylase and LHCP families (Kuhlemcier et al., 1989; Feinbaum et al., 1991; Weisshaar et al., 1991; Lam and Chua, 1990; Castresana et al., 1988; Schulze-Lefert et al., 1989).

Examples of useful tissue or organ specific promoters include β-conglycinin, (Doyle et al., 1986; Slighton and Beachy, 1987), and other seed specific promoters (Knutzon et al., 1992; Bustos et al., 1991; Lam and Chua, 1991). Plant functional promoters useful for preferential expression in seed plastid include those from plant storage proteins and from proteins involved in fatty acid biosynthesis in oilseeds. Examples of such promoters include the 5' regulatory regions from such structural nucleic acid sequences as napin (Kridl et al., 1991), phaseolin, zein, soybean trypsin inhibitor, ACP, stearoyl-ACP desaturase, and oleosin. Seed-specific regulation is further discussed in EP Application No. 0 255 378.

Another exemplary seed specific promoter is a lectin promoter. The lectin protein in soybean seeds is encoded by a single structural nucleic acid sequence (Le1) that is only expressed during seed maturation. A lectin structural nucleic acid sequence and seed-specific promoter have been characterized and used to direct seed specific expression in transgenic tobacco plants (Vodkin et al., 1983; Lindstrom et al., 1990.)

Particularly preferred additional promoters in the recombinant vector include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBlSCO); the EIF-4A promoter from tobacco (Mandel et al., 1995); corn sucrose synthetase 1 (Yang and Russell, 1990); corn alcohol dehydrogenase 1 (Vogel et al., 1989); corn light harvesting complex (Simpson, 1986); corn heat shock protein (Odell et al., 1985); the chitinase promoter from *Arabidopsis* (Samac et al., 1991); the LTP (Lipid Transfer Protein) promoters from broccoli (Pyee et al., 1995); *petunia* chalcone isomerase (Van Tunen et al., 1988); bean glycine rich protein 1 (Keller et al., 1989); potato patatin (Wenzler et al., 1989); the ubiquitin promoter from maize (Christensen et al., 1992); and the actin promoter from rice (McElroy et al., 1990).

An additional promoter is preferably seed selective, tissue selective, constitutive, or inducible. The promoter is most preferably the nopaline synthase (nos), octopine synthase (ocs), mannopine synthase (mas), cauliflower mosaic virus 19S and 35S (CaMV19S, CaMV35S), enhanced CaMV (eCaMV), ribulose 1,5-bisphosphate carboxylase (ssRUBISCO), figwort mosaic virus (FMV), CaMV derived AS4, tobacco RB7, wheat POX1, tobacco EIF-4, lectin protein (Le1), or rice RC2 promoter.

Recombinant Vectors Having Additional Structural Nucleic Acid Sequences

A recombinant vector may also contain one or more additional structural nucleic acid sequences. These additional structural nucleic acid sequences may generally be any sequences suitable for use in a recombinant vector. Such structural nucleic acid sequences include any of the structural nucleic acid sequences, and modified forms thereof, described above. Additional structural nucleic acid sequences may also be operably linked to any of the above described promoters. One or more structural nucleic acid sequences may each be operably linked to separate promoters. Alternatively, the structural nucleic acid sequences may be operably linked to a single promoter (i.e., a single operon).

Additional structural nucleic acid sequences preferably encode seed storage proteins, herbicide resistance proteins, disease resistance proteins, fatty acid biosynthetic enzymes, tocopherol biosynthetic enzymes, amino acid biosynthetic enzymes, or insecticidal proteins. Preferred structural nucleic acid sequences include, but are not limited to, gamma methyltransferase, phytyl prenyltransferase, beta-ketoacyl-CoA synthase, fatty acyl-CoA reductase, fatty acyl CoA:fatty alcohol transacylase, anthranilate synthase, threonine deaminase, acetohydroxy acid synthase, aspartate kinase, dihydroxy acid synthase, aspartate kinase, dihydropicolinate synthase, thioesterase, 7Sα seed storage protein, 11S seed storage protein, glycinin, beta-conglycinin, phaseolin, corn globulin-1, corn zeins, seed albumin, and seed lectin.

Alternatively, a second structural nucleic acid sequence may be designed to down-regulate a specific nucleic acid sequence. This is typically accomplished by operably linking the second structural amino acid, in an antisense orientation, with a promoter. One of ordinary skill in the art is familiar with such antisense technology. Any nucleic acid sequence may be negatively regulated in this manner. Preferable target nucleic acid sequences contain a low content of essential amino acids, yet are expressed at relatively high levels in particular tissues. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived foodstuffs.

Selectable Markers

The recombinant vector may further comprise a selectable marker. A nucleic acid sequence serving as the selectable marker functions to produce a phenotype in cells which facilitates their identification relative to cells not containing the marker.

Examples of selectable markers include, but are not limited to: a neo gene (Potrykus et al., 1985), which codes for kanamycin resistance and can be selected for using kanamycin, G418, etc.; a bar gene which codes for bialaphos resistance; a mutant EPSP synthase gene (Hinchee et al., 1988) which encodes glyphosate resistance; a nitrilase gene which confers resistance to bromoxynil (Stalker et al., 1988); a mutant acetolactate synthase gene (ALS) which confers imidazolinone or sulphonylurea resistance (EP Application No. 0 154 204); green fluorescent protein (GFP); and a methotrexate resistant DHFR gene (Thillet et al., 1988).

Other exemplary selectable markers include: a β-glucuronidase or uidA gene (GUS), which encodes an enzyme for which various chromogenic substrates are known (Jefferson (I), 1987; Jefferson (II) et al., 1987); an R-locus gene, which encodes a product that regulates the production of anthocyanin pigments (red color) in plant tissues (Dellaporta et al., 1988); a β-lactamase gene (Sutcliffe et al., 1978), which encodes an enzyme for which various chromogenic substrates are known (e.g., PADAC, a chromogenic cephalosporin); a luciferase gene (Ow et al., 1986); a xylE gene (Zukowsky et al., 1983) which encodes a catechol dioxygenase that can convert chromogenic catechols; an α-amylase gene (Ikatu et al., 1990); a tyrosinase gene (Katz et al., 1983), which encodes an enzyme capable of oxidizing tyrosine to DOPA and dopaquinone (which in turn condenses to melanin); and an α-galactosidase, which will alter the color of a chromogenic α-galactose substrate.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable marker genes will be apparent to those of skill in the art.

The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

Other Elements in the Recombinant Vector

Various cis-acting untranslated 5' and 3' regulatory sequences may be included in the recombinant nucleic acid vector. Any such regulatory sequences may be provided in a recombinant vector with other regulatory sequences. Such combinations can be designed or modified to produce desirable regulatory features.

A 3' non-translated region typically provides a transcriptional termination signal, and a polyadenylation signal which functions in plants to cause the addition of adenylate nucleotides to the 3' end of the mRNA. These may be obtained from the 3' regions of the nopaline synthase (nos) coding sequence, the soybean 7Sα storage protein coding sequence, the arcelin-5 coding sequence, the albumin coding sequence, and the pea ssRUBISCO E9 coding sequence. Particularly preferred 3' nucleic acid sequences include Arcelin-5 3', nos 3', E9 3', adr12 3', 7Sα 3', 11S 3', USP 3', and albumin 3'.

Typically, nucleic acid sequences located a few hundred base pairs downstream of the polyadenylation site serve to terminate transcription. These regions are required for efficient polyadenylation of transcribed mRNA.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5'.

The recombinant vector may further comprise a nucleic acid sequence encoding a transit peptide. This peptide may be useful for directing a protein to the extracellular space, a chloroplast, or to some other compartment inside or outside of the cell (EP Application No. 0 218 571).

The structural nucleic acid sequence in the recombinant vector may comprise introns. The introns may be heterologous with respect to the structural nucleic acid sequence. Preferred introns include the rice actin intron and the corn HSP70 intron.

Fusion Proteins

Any of the above described structural nucleic acid sequences, and modified forms thereof, may be linked with additional nucleic acid sequences to encode fusion proteins. The additional nucleic acid sequence preferably encodes at least 1 amino acid, peptide, or protein. Production of fusion proteins is routine in the art and many possible fusion combinations exist.

For instance, the fusion protein may provide a "tagged" epitope to facilitate detection of the fusion protein, such as GST, GFP, FLAG, or polyHIS. Such fusions preferably encode between 1 and 50 amino acids, more preferably between 5 and 30 additional amino acids, and even more preferably between 5 and 20 amino acids.

Alternatively, the fusion may provide regulatory, enzymatic, cell signaling, or intercellular transport functions. For example, a sequence encoding a chloroplast transit peptide may be added to direct a fusion protein to the chloroplasts within seeds. Such fusion partners preferably encode between 1 and 1000 additional amino acids, more preferably between 5 and 500 additional amino acids, and even more preferably between 10 and 250 amino acids.

Sequence Analysis

In the present invention, sequence similarity or identity is preferably determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith et al., 1983).

The Sequence Analysis Software Package described above contains a number of other useful sequence analysis tools for identifying homologues of the presently disclosed nucleotide and amino acid sequences. For example, the "BLAST" program (Altschul et al., 1990) searches for sequences similar to a query sequence (either peptide or nucleic acid) in a specified database (e.g., sequence databases maintained at the National Center for Biotechnology Information (NCBI) in Bethesda, Md., USA); "FastA" (Lipman and Pearson, 1985; see also Pearson and Lipman, 1988; Pearson, 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic acid sequence before performing the comparison).

Probes and Primers

Short nucleic acid sequences having the ability to specifically hybridize to complementary nucleic acid sequences may be produced and utilized in the present invention. These short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed.

Any of the nucleic acid sequences disclosed herein may be used as a primer or probe. Use of these probes or primers may greatly facilitate the identification of transgenic plants which contain the presently disclosed promoters and structural nucleic acid sequences. Probes may also be used to screen cDNA or genomic libraries for additional nucleic acid sequences related to or sharing homology with the presently disclosed promoters and structural nucleic acid sequences.

Alternatively, short nucleic acid sequences may be used as oligonucleotide primers to amplify or mutate a complementary nucleic acid sequence using PCR technology. These primers may also facilitate the amplification of related complementary nucleic acid sequences (e.g., related nucleic acid sequences from other species).

Short nucleic acid sequences may be used as probes and specifically as PCR probes. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www.genome.wi.mit.edu/ cgi-bin/primer/primer3.cgi), STSPipeline (www-genome.wi.mit.edu/cgi-bin/www.STS_Pipeline), or GeneUp (Pesole et al., 1998), for example, can be used to identify potential PCR primers.

A primer or probe is generally complementary to a portion of a nucleic acid sequence that is to be identified, amplified, or mutated, and should be of sufficient length to form a stable and sequence-specific duplex molecule with its complement. A primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may, for example, be prepared by direct chemical synthesis, by PCR (U.S. Pat. Nos. 4,683,195 and 4,683,202), or by excising the nucleic acid specific fragment from a larger nucleic acid molecule.

Transgenic Plants and Transformed Plant Host Cells

The invention is also directed to transgenic plants and transformed host cells which comprise, in a 5' to 3' orientation, any of the nucleic acids disclosed herein. Other nucleic acid sequences may also be introduced into the plant or host cell along with the nucleic acid sequence of the present invention. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

Means for preparing such recombinant vectors are well known in the art. For example, methods for making recombinant vectors particularly suited to plant transformation are described in U.S. Pat. Nos. 4,971,908; 4,940,835; 4,769,061 and 4,757,011. These vectors have also been reviewed (Rodriguez et al., 1988; Glick et al., 1993) and are described above.

Typical vectors useful for expression of nucleic acids in cells and higher plants are well known in the art and include vectors derived from the tumor-inducing (Ti) plasmid of *Agrobacterium tumefaciens* (Rogers et al., 1987). Other recombinant vectors useful for plant transformation, have also been described (Fromm et al., 1985). Elements of such recombinant vectors are discussed above.

A transformed plant cell or plant may generally be any cell or plant which is compatible with the present invention.

The plant or plant cell preferably is an alfalfa, apple, banana, barley, bean, broccoli, cabbage, carrot, castorbean, celery, citrus, clover, coconut, coffee, corn, cotton, cucumber, Douglas fir, *Eucalyptus*, garlic, grape, linseed, Loblolly pine, melon, oat, olive, onion, palm, parsnip, pea, peanut, pepper, poplar, potato, radish, *Radiata* pine, rapeseed, rice, rye, sorghum, *Lupinus angustifolius*, Southern pine, soybean, spinach, strawberry, sugarbeet, sugarcane, sunflower, Sweetgum, tea, tobacco, tomato, turf, or wheat plant or cell. In a more preferred embodiment, the plant or plant cell is soybean, corn, or wheat. In an even more preferred embodiment, the plant or plant cell is soybean.

The soybean cell or plant is preferably an elite soybean cell line. An "elite line" is any line that has resulted from breeding and selection for superior agronomic performance. Examples of elite lines are lines that are commercially available to farmers or soybean breeders such as HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™ variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 Roundup Ready™, HARTZ™ variety H4994 Roundup Ready™, HARTZ™ variety H4988 Roundup Ready™, HARTZ™ variety H5000 Roundup Ready™, HARTZ™ variety H5147 Roundup Ready™, HARTZ™ variety H5247 Roundup Ready™, HARTZ™ variety H5350 Roundup Ready™, HARTZ™ variety H5545 Roundup Ready™, HARTZ™ variety H5855 Roundup Ready™, HARTZ™ variety H5088 Roundup Ready™, HARTZ™ variety H5164 Roundup Ready™, HARTZ™ variety H5361 Roundup Ready™, HARTZ™ variety H5566 Roundup Ready™, HARTZ™ variety H5181 Roundup Ready™, HARTZ™ variety H5889 Roundup Ready™, HARTZ™ variety H5999 Roundup Ready™, HARTZ™ variety H6013 Roundup Ready™, HARTZ™ variety H6255 Roundup Ready™, HARTZ™ variety H6454 Roundup Ready™, HARTZ™ variety H6686 Roundup Ready™, HARTZ™ variety H7152 Roundup Ready™, HARTZ™ variety H7550 Roundup Ready™, and HARTZ™ variety H8001 Roundup Ready™ (HARTZ SEED, Stuttgart, Ark., U.S.A.); A0868, AG0901, A1553, A1900, AG1901, A1923, A2069, AG2101, AG2201, A2247, AG2301, A2304, A2396, AG2401, AG2501, A2506, A2553, AG2701, AG2702, A2704, A2833, A2869, AG2901, AG2902, AG3001, AG3002, A3204, A3237, A3244, AG3301, AG3302, A3404, A3469, AG3502, A3559, AG3601, AG3701, AG3704, AG3750, A3834, AG3901, A3904, A4045, AG4301, A4341, AG4401, AG4501, AG4601, AG4602, A4604, AG4702, AG4901, A4922, AG5401, A5547, AG5602, A5704, AG5801, AG5901, A5944, A5959, AG6101, QR4459 and QP4544 (Asgrow Seeds, Des Moines, Iowa, U.S.A.); DeKalb variety CX445 (DeKalb, Ill.).

The invention is also directed to a method of producing transformed plants which comprise, in a 5' to 3' orientation, a nucleic acid sequence of the present invention. Other sequences may also be introduced into plants along with the promoter and structural nucleic acid sequence. These other sequences may include, without limitation, 3' transcriptional terminators, 3' polyadenylation signals, other untranslated sequences, transit or targeting sequences, selectable markers, enhancers, and operators. Preferred recombinant vectors, structural nucleic acid sequences, promoters, and other regulatory elements are described herein.

The method generally comprises the steps of selecting a suitable plant, transforming the plant with a recombinant vector, and obtaining the transformed host cell.

There are many methods for introducing nucleic acids into plants. Suitable methods include bacterial infection (e.g., *Agrobacterium*), binary bacterial artificial chromosome vectors, direct delivery of nucleic acids (e.g., via PEG-mediated transformation), desiccation/inhibition-mediated nucleic acid uptake, electroporation, agitation with silicon carbide fibers, and acceleration of nucleic acid coated particles, etc. (reviewed in Potrykus et al., 1991).

Technology for introduction of nucleic acids into cells is well known to those of skill in the art. Methods can generally be classified into four categories: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253), and particle acceleration (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992). Alternatively, nucleic acids can be directly introduced into pollen by directly injecting a plant's reproductive organs (Zhou et al., 1983; Hess, 1987; Luo et al., 1988; Pena et al., 1987). Nucleic acids may also be injected into immature embryos (Neuhaus et al., 1987).

A recombinant vector used to transform the host cell typically comprises, in a 5' to 3' orientation: a promoter to direct the transcription of a structural nucleic acid sequence, a structural nucleic acid sequence, a 3' transcriptional terminator, and a 3' polyadenylation signal. The recombinant vector may further comprise untranslated nucleic acid sequences, transit and targeting nucleic acid sequences, selectable markers, enhancers, or operators.

Suitable recombinant vectors, structural nucleic acid sequences, promoters, and other regulatory elements are described above.

Regeneration, development, and cultivation of plants from transformed plant protoplast or explants is taught in the art (Weissbach and Weissbach, 1988; Horsch et al., 1985). In this method, transformants are generally cultured in the presence of a selective media which selects for the successfully transformed cells and induces the regeneration of plant shoots (Fraley et al., 1983). These shoots are typically obtained within two to four months.

Shoots are then transferred to an appropriate root-inducing medium containing the selective agent and an antibiotic to prevent bacterial growth. Many of the shoots will develop roots. These are then transplanted to soil or other media to allow the continued development of roots. A method will generally vary depending on the particular plant strain employed.

Preferably, the regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the nucleic acid sequence encoding the enhanced gene expression to its progeny. The transgenic plant is preferably homozygous for the nucleic acid encoding the enhanced gene expression and transmits that sequence to all of its offspring upon as a result of sexual reproduction. Progeny may be grown from seeds produced by the transgenic plant. These additional plants may then be self-pollinated to generate a true breeding line of plants.

The progeny from these plants are evaluated, among other things, for gene expression. The gene expression may be detected by several common methods such as western blotting, northern blotting, immunoprecipitation, and ELISA.

Seed Containers

Seeds of a plant or plants of the present invention may be placed a container. As used herein, a container is any object capable of holding such seeds. A container preferably contains greater than 1,000, 5,000, or 25,000 seeds where at least 10, 25, 50, 75 or 100% of the seeds are derived from a plant of the present invention.

Feed, Meal, Protein and Oil Preparations

Any of the plants or parts thereof of the present invention may be processed to produce a feed, meal, protein or oil preparation. A particularly preferred plant part for this purpose is a seed. In a preferred embodiment the feed, meal, protein or oil preparation is designed for ruminant animals. Methods to produce feed, meal, protein and oil preparations are known in the art. See, for example, U.S. Pat. Nos. 4,957,748; 5,100,679; 5,219,596; 5,936,069; 6,005,076; 6,146,669 and 6,156,227. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. In another embodiment, the oil preparation may be blended and can constitute greater than 10, 25, 35, 50 or 75% of the blend by volume.

Other Organisms

Any of the above described nucleic acid sequences may be introduced into any cell or organism such as a mammalian cell, mammal, fish cell, fish, bird cell, bird, algae cell, algae, fungal cell, fungi, or bacterial cell. Preferred hosts and transformants include: fungal cells such as *Aspergillus*, yeasts, mammals (particularly bovine and porcine), insects, bacteria and algae. Particularly preferred bacteria cells are *Agrobacterium* and *E. coli*.

In another particularly preferred embodiment, the cell is selected from the group consisting of a bacteria cell, a mammalian cell, an insect cell, and a fungal cell.

Methods to transform such cells or organisms are known in the art (EP Application No. 0 238 023; Yelton et al., 1984; Malardier et al., 1989; Becker and Guarente; Ito et al., 1983; Hinnen et al., 1978; and Bennett and LaSure, 1991). Methods to produce proteins of the present invention from such organisms are also known (Kudla et al., 1990; Jarai and Buxton, 1994; Verdier, 1990; MacKenzie et al., 1993; Hartl et al., 1994; Bergeron et al., 1994; Demolder et al., 1994; Craig, 1993; Gething and Sambrook, 1992; Puig and Gilbert, 1994; Wang and Tsou, 1993; Robinson et al., 1994; Enderlin and Ogrydziak, 1994; Fuller et al., 1989; Julius et al., 1984; and Julius et al., 1983).

Exemplary Uses of the Invention:

Uses of the present invention include nutritional supplementation for animals, including humans. The supplementation forms for animals include feed rations, meal, and protein prep from grain. The supplementation forms for humans include soy protein prep and infant formula.

In a preferred embodiment, proteins, seeds, and plants of the present invention are used in human food. As used herein, "human food" refers to any food fit for human consumption. In a preferred embodiment, human food is any food that is derived from agricultural sources, whether directly in the form of plant products or indirectly in the form of animal products that are derived from animals that fed on plants from agricultural sources. In a further preferred embodiment, human food is any food that is derived from plants or seeds of the present invention, whether directly in the form of plant products or indirectly in the form of animal products that are derived from animals that fed on plants from agricultural sources. In another embodiment, human food is any food that is derived from soybean plants or seeds of the present invention, whether directly in the form of soybean plant products of the present invention or indirectly in the form of animal products that are derived from animals that fed on soybean plants of the present invention.

The following examples are illustrative only. It is not intended that the present invention be limited to the illustrative embodiments.

EXAMPLES

The following examples are exemplary only, and do not limit the scope of the invention.

Example 1

Preparation of Early Soybean Seed mRNA

Total cellular RNA, containing mRNA transcribed from a β-conglycinin β subunit gene, is isolated from soybean seeds. Immature soybean seeds are ground (~180 mg) into a powder and added to a 50 ml microcentrifuge tube. 2.5 ml of TRIZOL™ (Invitrogen, Carlsbad, Calif.) are added and the mixture is homogenized in a Polytron™ (Model PT 1200, Brinkmann Instruments, Inc., Westbury, N.Y.) for 20 to 30 seconds. The homogenized mixture is incubated at room temperature for 5 minutes. 0.5 ml of chloroform is added to the homogenate and the tube is capped securely. The tube is shaken vigorously and left standing for 2 to 3 minutes at room temperature. The samples are centrifuged at 12,000×g for 15 minutes at 4° C. The clear aqueous phase is transferred to a fresh 50 ml tube and the cloudy organic phase is discarded. 1.25 ml of isopropyl alcohol is added to the aqueous phase, mixed well, and incubated at room temperature for 10 minutes. The tube is centrifuged at 12,000×g for 10 minutes at 4° C. The supernatant is removed and the pellet is washed with 2.5 ml of 75% ethanol. The pellet is mixed in ethanol by vortexing. The tube is centrifuged at 7,500×g for 5 minutes at 4° C. The supernatant is removed and the pellet is air dried for 5 to 10 minutes. The pellet is resuspended in 400 µl of DEPC H$_2$O. The sample is diluted 1:100 and the concentration of the RNA is determined by measuring the OD$_{260/280}$. The presence of RNA is confirmed by non-denaturing gel electrophoresis and visualization under UV light.

Example 2

RT-PCR of the β-Conglycinin β Subunit Gene from Early Soybean Seed mRNA

A DNA sequence complementary to the β-conglycinin β subunit mRNA present in the total cellular RNA isolated in Example 1 is prepared using the Titan™ One Tube RT-PCR system (Boehringer Mannheim, Indianapolis, Ind.). The following oligonucleotide primers are prepared by desalting, lyophilizing, and resuspending in water at a final concentration of 100 mM as a stock solution.

```
BetaC-5'A:
5'-ATA CTA TGA TGA GAG TGC GG-3'    (SEQ ID NO: 4)

BetaC-5'B:
5'-CAC TCC ATG TTT CAT CGT CC-3'    (SEQ ID NO: 5)

BetaC-3'A:
5'-GTT ATT CAG TAG AGA GCA CC-3'    (SEQ ID NO: 6)

BetaC-3'B:
5'-TCA CGA TGA GCT CTT ACA GC-3'    (SEQ ID NO: 7)
```

For the RT-PCR, the primers are diluted to a final working concentration of 20 mM. The following reaction mixtures are prepared for the RT-PCR reaction:

| Master Mix 1 | | | | |
| --- | --- | --- | --- | --- |
| | 1 | 2 | 3 | 4 |
| DNTP (10 mM each) | 1 µl | 1 µl | 1 µl | 1 µl |
| BetaC-5'A primer or BetaC-5'B primer (20 µg/µl) | 1 µl 5'A | 1 µl 5'A | 1 µl 5'B | 1 µl 5'B |
| BetaC-3'A primer or BetaC-3'B primer (20 µg/µl) | 1 µl 3'A | 1 µl 3'B | 1 µl 3'A | 1 µl 3'B |
| Template RNA (0.7 µg/µl) | 1 µl | 1 µl | 1 µl | 1 µl |
| DTT (100 µM) | 2.5 µl | 2.5 µl | 2.5 µl | 2.5 µl |
| H$_2$O | 18.5 µl | 18.5 µl | 18.5 µl | 18.5 µl |
| TOTAL | 25 µl | 25 µl | 25 µl | 25 µl |

| Master Mix 2 | |
| --- | --- |
| 5X RT-PCR buffer | 80 µl |
| H$_2$O | 112 µl |
| Enzyme Mix | 8 µl |
| Total | 200 µl |

Each Master Mix 1 sample is added to 0.2 ml thin well PCR tubes. A duplicate reaction mixture that does not contain any template RNA is prepared as a control. 24 µl of Master Mix 2 is added to each of the tubes. An RT-PCR is performed on a PTC-200 Peltier Thermocycler with the following program sequence: 1) 50° C. for 30 minutes; 2) 94° C. for 2 minutes; 3) 94° C. for 30 seconds; 4) 45° C. for 30 seconds; 5) 68° C. for 90 seconds; 6) Go to step (3) and repeat for 9 additional cycles; 7) 94° C. for 30 seconds; 8) 45° C. for 30 seconds; 9) 68° C. for 90 seconds; 10) Go to step 7, repeat for 9 additional cycles plus 5 seconds each cycle; 11) 68° C. for 7 minutes; 12) Cool to 4° C. and end program.

The PCR reaction products are separated on an agarose gel. PCR fragments from the gel are excised and purified using standard protocols. One exemplary resulting cDNA is SEQ ID NO: 3. The translation product of the cDNA is given as SEQ ID NO: 1.

Example 3

Preparation of Recombinant Nucleic Acid Vector Containing a Sequence Encoding a β-Conglycinin β Subunit The PCR products isolated in Example 2 are ligated into the pCRII™ vector using the TA™ cloning kit (Invitrogen, Carlsbad, Calif.). Ligation is performed according to the manufacturer's protocol using the following 10 µl ligation reaction mixtures:

| | | | | |
| --- | --- | --- | --- | --- |
| PCR Product | 6 µl[1] | 10 µl[1] | 2 µl[2] | 0 µl |
| 10x Ligation B | 1 µl | 2 µl | 1 µl | 1 µl |
| PCRII Vector | 2 µl | 2 µl | 2 µl | 2 µl |
| H$_2$O | 0 µl | 4 µl | 4 µl | 4 µl |
| T4 DNA Ligase | 1 µl | 1 µl | 1 µl | 1 µl |

[1]gel purified PCR product
[2]direct PCR product (not gel purified)

Example 4

Preparation of Transformed Host Cells Containing a Vector Encoding a Wild-Type β-Conglycinin β Subunit The ligated pCRII vectors containing the PCR products are transformed into One Shot™ competent cells (*E. coli* INVαF'strain) (Invitrogen, Carlsbad, Calif.) and are centrifuged according to the manufacturer's protocol.

DNA is prepared from a QIAprep™ (Qiagen Inc., Valencia, Calif.) miniprep kit, according to the manufacturer's protocols. A sample from each of the DNA minipreps is digested with EcoRI/XbaI to generate DNA fragments. The EcoRI digestion yields 3.9, 0.58, and 0.75 kb fragments. The XbaI digestion yields either 0.59 and 4.62 kb fragments (pMON54419), or 0.72 and 4.44 kb fragments (pMON54418). The presence of the correct sized fragments corresponding to DNA fragments from the β-conglycinin β subunit gene is confirmed by gel electrophoresis. DNA minipreps and transformed cells having the β-conglycinin β subunit gene are selected. The sequence of the β-conglycinin β subunit DNA is compared with the published wild-type sequence. Sequences exhibiting a 100% match to the published wild-type β-conglycinin β subunit gene sequence are selected.

Example 5

Preparation of Transgenic Plants and Seeds

Transformation vectors capable of introducing nucleic acid sequences encoding the modified β-conglycinin β subunit are designed and generally contain one or more nucleic acid coding sequences of interest under the transcriptional control of 5' and 3' regulatory sequences. Such vectors comprise, operatively linked in sequence in the 5' to 3' direction, a promoter sequence that directs the transcription of a downstream structural nucleic acid sequence in a plant; a 5' non-translated leader sequence; a nucleic acid sequence that encodes a modified β-conglycinin β subunit sequence and a 3' non-translated region that provides a polyadenylation signal and termination signal.

Each of the modified β-conglycinin sequences are inserted into plant transformation vectors and transformed into plant tissue, e.g., soybean cotyledons. The transformed plant tissue is cultured in suitable selection and growth media to generate a transgenic plant containing the modified β-conglycinin sequence.

A variety of different methods can be employed to introduce such vectors into plant protoplasts, cells, callus tissue, leaf discs, meristems, and other plant tissues, to generate transgenic plants. The plant cells or plant tissue is transformed with the plant vector by Agrobacterium-mediated transformation, particle gun delivery, microinjection, electroporation, polyethylene glycol-mediated protoplast transformation, liposome-mediated transformation, etc. (reviewed in Potrykus, 1991). Plant cells or tissues are thus transformed with the plant vector containing the β-conglycinin β subunit sequence.

Transgenic plants are produced by transforming plant cells with a plant vector, as described above; selecting plant cells or tissues that have been transformed; regenerating plant cells that have been transformed to produce transgenic plants; and selecting the transgenic plants that express the desired β-conglycinin β subunit sequence.

The transgenic plants are screened for protein expression of the desired polypeptide having increased content of essential amino acids. The plants may also be screened for polypeptides having increased content of other essential amino acids, such as histidine, lysine, methionine, and phenylalanine.

Example 6

Expression and Self-Assembly of Epitope-Tagged β-Conglycinin β Subunit in E. coli In order to distinguish modified forms of β-conglycinin β subunit from the endogenous form that accumulates in non-transformed soybeans, a "FLAG" epitope coding sequence is attached to the coding sequence representing the amino-terminus of the mature form (lacking signal peptide) of the β subunit. The FLAG epitope consists of the 8 residue sequence Asp-Tyr-Lys-Asp-Asp-Asp-Asp-Lys (SEQ ID NO: 9)(5'GAC TAC AAG GAC GAC GAT GAC AAG 3' (SEQ ID NO: 8). The FLAG coding sequence, plus an additional methionine codon to serve as a translation start codon, is added onto the amino-terminus of the mature β subunit coding sequence by standard PCR technology using pMON54418 as a template according to the manufacturer's directions (Boehringer Mannheim, Indianapolis, Ind., Expand High Fidelity PCR System) and using the following primers: 5'ATAGCCATGGACTACAAGGACGACGAT-GACAAGTTAAAGGTGAGAGAGGATG AG 3' (SEQ ID NO: 10) and 5'GTAAAACGACGGCCAG 3' (SEQ ID NO: 11). The resulting 1.4 kb PCR product is digested with NcoI+NotI and cloned into the NcoI and NotI sites of E. coli expression vector, pET21d(+) (Novagen, Madison, Wis.), to create pMON39328, which is shown in FIG. 1.

The epitope (FLAG)-tagged form of the β-conglycinin β subunit encoded by pMON39328 has the amino acid sequence of SEQ ID NO: 12.

The nucleotide sequence in pMON39328 encoding the epitope (FLAG)-tagged form of the β-conglycinin β subunit has the sequence of SEQ ID NO: 13.

Figure 2:
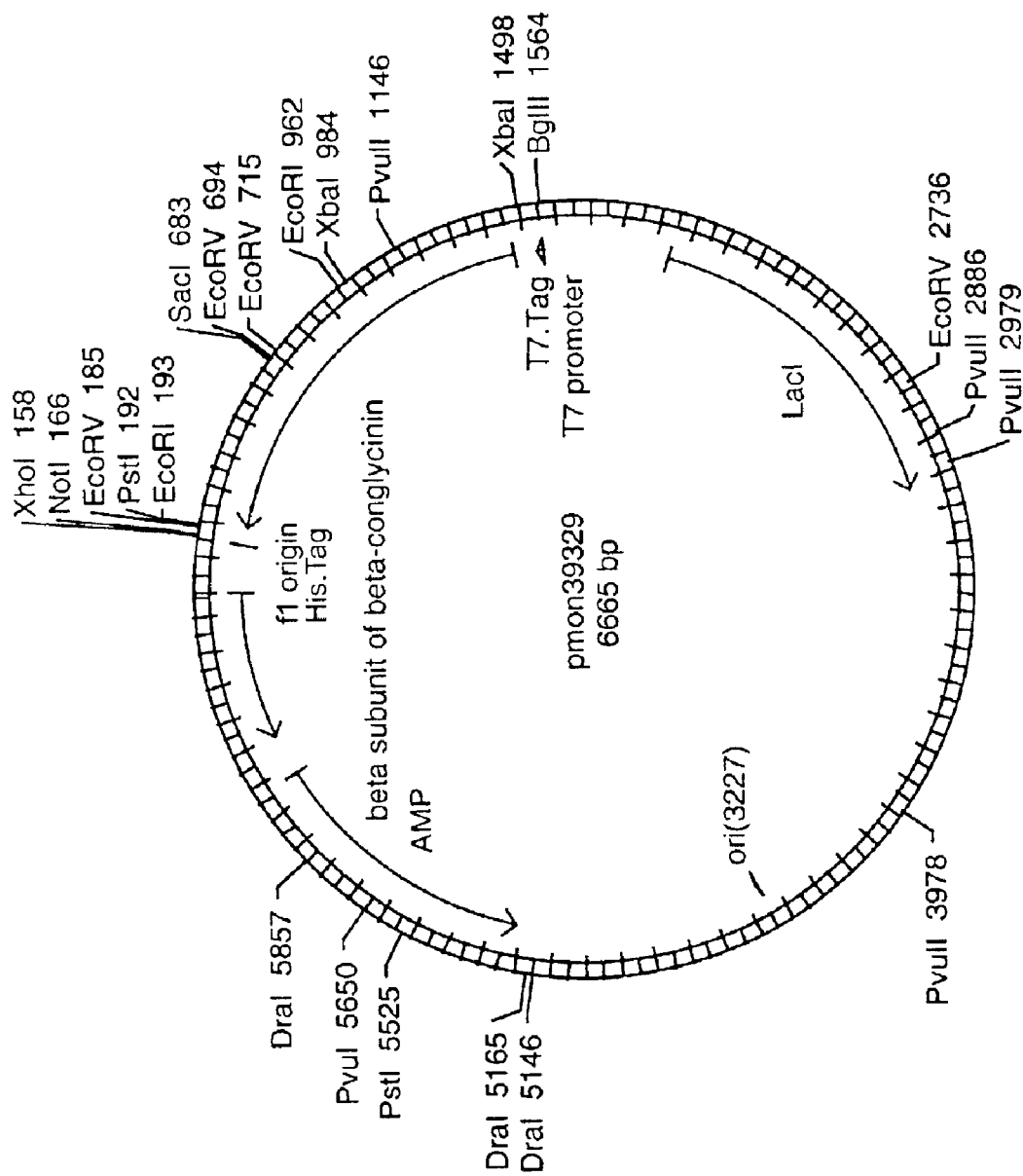
FIG. 2 is a map of pMON39329.

A second plasmid, pMON39329, shown in FIG. 2, is created that contains the coding sequence for the mature form of the β subunit (without the FLAG epitope) in pET21d(+).

The mature form (plus additional methionine encoded by start codon) of the β-conglycinin β subunit encoded by pMON39329 has the amino acid sequence of SEQ ID NO: 14.

The nucleotide sequence in pMON39329 encoding the mature form of the β-conglycinin β subunit has the sequence of SEQ ID NO: 15.

Plasmids pMON39328 and pMON39329 are transformed into E. coli BL21 (DE3) according to manufacturer's instructions (Strategene, La Jolla Calif.). A single colony is used to inoculate 2 ml LB medium. The culture is grown at 37° C. until a cell density corresponding to $A_{600}$=0.6 is achieved. An amount corresponding to a final concentration of 1 mM isopropyl-1-thio-β-D-galactopyranoside (IPTG) is added to induce protein expression and the culture is incubated at temperatures ranging from 20° to 37° C. at 225 rpm for time periods up to 20 hours. Cells are harvested by centrifugation at 5,000 rpm for 15 minutes at 4° C. The cell pellet is re-suspended in protein extraction buffer consisting of 20 mM Tris-HCl, pH 7.4, 0.4 M NaCl, 0.1% TritonX-100, 40 µl/ml Protease Inhibitor Cocktail, (stock: 1 tablet/2 ml, Boehringer Mannheim, Indianapolis, Ind.). The cells are then disrupted by sonication (Branson Sonifier 450, Branson Precision Processing, Danbury, Conn.) while maintaining at cold temperature with ice. Soluble proteins are separated from the insoluble fraction by centrifugation at 13,000 rpm for 5 minutes. Results from coomassie staining and a Western blotting with Anti-FLAG antibody show that the solubility and expression level of the native and the FLAG-tagged forms are indistinguishable. When expression is induced at 37° C., both proteins accumulated primarily in an insoluble form, while induction at 20° or 30° C. results in about 50% of the protein accumulating in the soluble fraction.

To determine if the recombinant forms of β subunit expressed in E. coli from pMON39328 and pMON39329 could self-assemble to form trimers, aliquots of the soluble protein fraction from E. coli lysates are layered onto 12 ml of a 5–25% sucrose density gradient and centrifuged at 36,000 rpm for 17.5 hours at 20° C. (Sorvall TH-641 rotor; Sorvall Ultra Pro 80 ultracentrifuge). Following centrifugation, the gradient is divided into fractions using a Labconco Autodensi-Flow instrument (Labconco, Kansas City, Mo.), and each fraction is analyzed by western blot analysis using Anti-FLAG M2 antibody (Stratagene Corporation, LaJolla, Calif.) to determine which fractions contained β-conglycinin β subunit. 7S and 1 IS soy protein fractions, as well as ovalbumin (45 kD) and aldolase (158 kD), are run as size markers on separate gradients. Results show that both the native and the FLAG-tagged forms co-sedimented with the 7S fraction isolated from soybean and with the aldolase standard, which indicates that both recombinant proteins had self-assembled to form trimers.

Example 7

Modification of the β-Conglycinin β Subunit Sequence to Encode Increased Levels of Tryptophan Site-directed mutagenesis reactions are carried out to substitute tryptophan codons at one or more of the following positions in the β-conglycinin β subunit sequence: N32; Y35; N40; N50; Y72; H88; Y116; H119; Y132; Y133; P137; Y158; Y172; E200; P239; Y249; P265; P324; Y330; Y346; N368; and Y411. The primers used in these reactions are listed in the table below, with sequence ID numbers and corresponding amino acid and codon subsititutions given in the right column. Substitutions for amino acids are substitutions in the unmodified β-conglycinin β subunit sequence given by SEQ ID NO: 1 and are represented in the following format: replaced amino acid single letter code/location in SEQ ID NO: 1/added amino acid single letter code. For example, SEQ ID NO: 16 is a change from tyrosine to tryptophan at amino acid 35 of SEQ ID NO: 1. The nucleotide substitutions in parenthesis are formatted similarly, with the change in nucleotide sequence of SEQ ID NO: 3, β-conglycinin β subunit cDNA, shown as a triplet substitution in the following format: unmodified triplet/position of first nucleotide of the triplet in SEQ ID NO: 3/modified triplet. For example, SEQ ID NO: 16 is a change from the triplet TAC to TGG at positions 103, 104, and 105 of SEQ ID NO: 3:

| Primer Sequence for Each Tryptophan Substitution | |
|---|---|
| Sequence ID | Substitution Sites |
| SEQ ID NO:16 | Y35W (TAC103TGG) |
| SEQ ID NO:17 | Y72W (TAC214TGG) |
| SEQ ID NO:18 | H88W (CAC262TGG) |
| SEQ ID NO:19 | Y116W (TAC316TGG) |
| SEQ ID NO:20 | Y132W (TAC394TGG) |
| SEQ ID NO:21 | Y133W (TAT397TGG) |

-continued

| Primer Sequence for Each Tryptophan Substitution | |
|---|---|
| Sequence ID | Substitution Sites |
| SEQ ID NO:22 | P137W (CCT409TGG) |
| SEQ ID NO:23 | Y158W (TAT472TGG) |
| SEQ ID NO:24 | Y172W (TAC514TGG) |
| SEQ ID NO:25 | E200W (GAA598TGG) |
| SEQ ID NO:26 | P239W (CCA715TGG) |
| SEQ ID NO:27 | Y249W (TAT745TGG) |
| SEQ ID NO:28 | P265W (CCA793TGG) |
| SEQ ID NO:29 | P324W (CCT970TGG) |
| SEQ ID NO:30 | Y330W (TAC988TGG) |
| SEQ ID NO:31 | Y346W (TAT1036TGG) |
| SEQ ID NO:32 | Y411W (TAC1128TGG) |
| SEQ ID NO:33 | N50W (AAC148TGG) |

Plasmid pMON39328 is used as as a template in all of these reactions. Mutants with IDs 39328-1 through 39328-28 are made using the QuickChange™ Site-Directed Mutagenesis Kit (Stratagene Corporation, La Jolla, Calif.) essentially according to the manufacture's directions and mutants with IDs 39328-31 through 39328-66 are made using the GeneEditor™ in vitro Site-Directed Mutagenesis System Kit (Promega Corporation, Madison, Wis.). Each mutagenic primer is designed to incorporate nucleotides encoding a tryptophan residue at those positions listed above. Primers are obtained from Invitrogen (Invitrogen, Carlsbad, Calif.) and are phosphorylated at the 5' terminus and purified by polyacrylamide gel electrophoresis. The tryptophan mutants and the sites of mutation, with notation as described above, are given in the table below:

| Mutant ID | Amino Acid and Nucleotide Substitutions |
|---|---|
| 39328-1 | Y35W (TAC103TGG) |
| 39328-2 | Y72W (TAC214TGG) |
| 39328-3 | H88W (CAC262TGG) |
| 39328-4 | Y116W (TAC316TGG) |
| 39328-5 | Y132W (TAC394TGG) |
| 39328-6 | Y133W (TAT397TGG) |
| 39328-7 | P137W (CCT409TGG) |
| 39328-8 | Y158W (TAT472TGG) |
| 39328-9 | Y172W (TAC514TGG) |
| 39328-10 | P239W (CCA715TGG) |
| 39328-11 | Y249W (TAT745TGG) |
| 39328-12 | P265W (CCA793TGG) |
| 39328-13 | P324W (CCT970TGG) |
| 39328-14 | Y330W (TAC988TGG) |
| 39328-15 | Y346W (TAT1036TGG) |
| 39328-16 | Y411W (TAC1128TGG) |
| 39328-17 | Y35W (TAC103TGG); Y72W (TAC214TGG) |
| 39328-18 | P239W (CCA715TGG); Y249W (TAT745TGG) |
| 39328-19 | P324W (CCT970TGG); Y330W (TAC988TGG) |
| 39328-20 | P239W (CCA715TGG); Y249W (TAT745TGG); P265W (CCA793TGG) |
| 39328-21 | Y133W (TAT397TGG); Y158W (TAT472TGG); Y172W (TAC514TGG) |
| 39328-22 | Y35W (TAC103TGG); Y72W (TAC214TGG); H88W (CAC262TGG); Y116W (TAC316TGG) |
| 39328-23 | Y35W (TAC103TGG); Y72W (TAC214TGG); Y116W (TAC316TGG); Y132W (TAC394TGG) |
| 39328-24 | P324W (CCT970TGG); Y330W (TAC988TGG); Y346W (TAT1036TGG); Y411W (TAC1128TGG) |
| 39328-25 | Y133W (TAT397TGG); P137W (CCT409TGG); Y158W (TAT472TGG); Y172W (TAC514TGG) |
| 39328-26 | Y35W (TAC103TGG); Y72W (TAC214TGG); H88W (CAC262TGG); Y116W (TAC316TGG); Y132W (TAC394TGG) |
| 39328-27 | Y35W (TAC103TGG); Y72W (TAC214TGG); H88W (CAC262TGG); Y116W (TAC316TGG); Y132W (TAC394TGG); Y133W (TAT397TGG) |

-continued

| Mutant ID | Amino Acid and Nucleotide Substitutions |
|---|---|
| 39328-28 | P239W (CCA715TGG); Y249W (TAT745TGG); P265W (CCA793TGG); P324W (CCT970TGG); Y330W (TAC988TGG); Y346W (TAT1036TGG); Y411W (TAC1128TGG) |
| 39328-31 | Y35W (TAC103TGG); Y72W (TAC214TGG); Y116W (TAC316TGG); Y132W (TAC394TGG); Y411W (TAC1128TGG) |
| 39328-32 | Y35W (TAC103TGG); Y72W (TAC214TGG); Y116W (TAC316TGG); P137W (CCT409TGG); Y158W (TAT472TGG); Y172W (TAC514TGG); Y330W (TAC988TGG); Y411W (TAC1128TGG) |
| 39328-33 | Y35W (TAC103TGG); Y72W (TAC214TGG); Y116W (TAC316TGG); Y132W (TAC394TGG); Y158W (TAT472TGG); Y172W (TAC514TGG); Y411W (TAC1128TGG) |
| 39328-34 | Y35W (TAC103TGG); Y72W (TAC214TGG); Y116W (TAC316TGG); P137W (CCT409TGG); Y158W (TAT472TGG); Y172W (TAC514TGG); Y411W (TAG1128TGG); |
| 39328-35 | Y35W (TAC103TGG); Y72W (TAC214TGG); Y116W (TAC316TGG); Y132W (TAC394TGG); Y158W (TAT472TGG); Y172W (TAC514TGG); |
| 39328-36 | Y72W (TAC214TGG); Y116W (TAC316TGG); P137W (CCT409TGG); Y158W (TAT472TGG); Y172W (TAC514TGG); P239W (CCA715TGG); Y249W (TAT745TGG); P265W (CCA793TGG); Y330W (TAC988TGG) |
| 39328-37 | Y35W (TAC103TGG); Y72W (TAC214TGG); Y116W (TAC316TGG); P137W (CCT409TGG); Y158W (TAT472TGG); Y172W (TAC514TGG); Y411W (TAC1128TGG); |
| 39328-38 | Y72W (TAC214TGG); Y116W (TAC316TGG); Y132W (TAC394TGG); Y158W (TAT472TGG); Y172W (TAC514TGG); P239W (CCA715TGG); Y249W (TAT745TGG); P265W (CCA793TGG); Y330W (TAC988TGG); Y411W (TAC1128TGG) |
| 39328-39 | Y35W (TAC103TGG); Y72W (TAC214TGG); Y116W (TAC316TGG); Y132W (TAC394TGG); P239W (CCA715TGG); Y249W (TAT745TGG); P265W (CCA793TGG); Y330W (TAC988TGG); Y346W (TAT1036TGG); Y411W (TAC1128TGG) |
| 39328-40 | Y72W (TAC214TGG); H88W (CAC262TGG); Y116W (TAC316TGG); Y132W (TAC394TGG); Y158W (TAT472TGG); Y172W (TAC514TGG); P239W (CCA715TGG); Y249W (TAT745TGG); P265W (CCA793TGG); Y330W (TAC988TGG); Y346W (TAT1036TGG); Y411W (TAC1128TGG) |
| 39328-41 | Y158W (TAT472TGG); Y172W (TAC514TGG); P239W (CCA715TGG); Y249W (TAT745TGG); Y330W (TAC988TGG); Y346W (TAT1036TGG); Y411W (TAC1128TGG) |
| 39328-42 | Y35W (TAC103TGG); Y72W (TAC214TGG); H88W (CAC262TGG); Y132W (TAC394TGG) |
| 39328-43 | H88W (CAC262TGG); Y116W (TAC316TGG); Y132W (TAC394TGG); Y172W (TAC514TGG); P239W (CCA715TGG); Y249W (TAT745TGG); P265W (CCA793TGG); Y330W (TAC988TGG); Y346W (TAT1036TGG); Y411W (TAC1128TGG) |
| 39328-44 | Y35W (TAC103TGG); Y72W (TAC214TGG); H88W (CAC262TGG); Y116W (TAC316TGG); Y158W (TAT472TGG); Y172W (TAC514TGG); P239W (CCA715TGG); Y249W (TAT745TGG); P265W (CCA793TGG); Y346W (TAT1036TGG); Y411W (TAC1128TGG) |
| 39328-45 | Y158W (TAT472TGG); Y172W (TAC514TGG); Y330W (TAC988TGG); Y346W (TAT1036TGG); Y411W (TAC1128TGG) |
| 39328-46 | Y158W (TAT472TGG); Y172W (TAC514TGG); P239W (CCA715TGG); Y249W (TAT745TGG); P265W (CCA793TGG); Y330W (TAC988TGG); Y346W (TAT1036TGG); Y411W (TAC1128TGG) |
| 39328-47 | Y116W (TAC316TGG); Y132W (TAC394TGG); Y158W (TAT472TGG); Y172W (TAC514TGG); P265W (CCA793TGG); Y346W (TAT1036TGG); Y411W (TAC1128TGG) |
| 39328-48 | P265W (CCA793TGG); Y330W (TAC988TGG); Y346W (TAT1036TGG); Y411W (TAC1128TGG) |
| 39328-49 | Y35W (TAC103TGG); Y72W (TAC214TGG); H88W (CAC262TGG); Y116W (TAC316TGG); Y158W (TAT472TGG); Y172W (TAC514TGG); P239W (CCA715TGG); Y249W (TAT745TGG); P265W (CCA793TGG); Y330W (TAC988TGG); Y346W (TAT1036TGG); Y411W (TAC1128TGG) |
| 39328-50 | Y35W (TAC103TGG); Y72W (TAC214TGG); H88W (CAC262TGG); Y116W (TAC316TGG); Y132W (TAC394TGG); P239W (CCA715TGG); Y249W (TAT745TGG); P265W (CCA793TGG); Y330W (TAC988TGG); Y346W (TAT1036TGG); Y411W (TAC1128TGG) |
| 39328-51 | Y132W (TAC394TGG); Y158W (TAT472TGG); Y172W (TAC514TGG); P239W (CCA715TGG); Y249W (TAT745TGG); P265W (CCA793TGG); Y330W (TAC988TGG); Y346W (TAT1036TGG); Y411W (TAC1128TGG) |
| 39328-52 | Y116W (TAC316TGG); Y330W (TAC988TGG); Y346W (TAT1036TGG); Y411W (TAC1128TGG) |
| 39328-53 | Y116W (TAC214TGG); P239W (CCA715TGG); Y249W (TAT745TGG); P265W (CCA793TGG); Y330W (TAC988TGG); Y346W (TAT1036TGG); Y411W (TAC1128TGG) |
| 39328-54 | P239W (CCA715TGG); Y249W (TAT745TGG); P265W (CCA793TGG); Y330W (TAC988TGG); Y346W (TAT1036TGG) |

-continued

| Mutant ID | Amino Acid and Nucleotide Substitutions |
|---|---|
| 39328-55 | Y116W (TAC316TGG); Y132W (TAC394TGG); Y158W (TAT472TGG); Y172W (TAC514TGG); P239W (CCA715TGG); Y330W (TAC988TGG); Y346W (TAT1035TGG); Y411W (TAC1128TGG) |
| 39328-57 | Y35W (TAC103TGG); Y72W (TAC214TGG); Y116W (TAC316TGG); Y132W (TAC394TGG); P137W (CCT409TGG); Y158W (TAT472TGG); Y172W (TAC514TGG); E200W (GAA598TGG); P265W (CCA793TGG); Y330W (TAC988TGG); Y346W (TAT1036TGG); Y411W (TAC1128TGG) |
| 39328-58 | Y35W (TAC103TGG); Y72W (TAC214TGG); Y116W (TAC316TGG); P137W (CCT409TGG); Y158W (TAT472TGG); Y172W (TAC514TGG) P265W (CCA793TGG); P324W (CCT970TGG); Y330W (TAC988TGG); Y346W (TAT1036TGG); Y411W (TAC1128TGG) |
| 39328-59 | Y35W (TAC103TGG); Y72W (TAC214TGG); Y116W (TAC316TGG); P137W (CCT409TGG); Y158W (TAT472TGG); Y172W (TAC514TGG) Y330W (TAC988TGG); Y411W (TAC1128TGG); Y133W (TAC397TGG) |
| 39328-60 | Y35W (TAC103TGG); Y72W (TAC214TGG); Y116W (TAC316TGG); P137W (CCT409TGG); Y158W (TAT472TGG); Y172W (TAC514TGG)Y330W (TAC988TGG); Y411W (TAC1128TGG); Y132W (TAC394TGG) |
| 39328-61 | Y35W (TAC103TGG); Y72W (TAC214TGG); Y116W (TAC316TGG); P137W (CCT409TGG); Y158W (TAT472TGG); Y172W (TAC514TGG) Y330W (TAC988TGG); Y411W (TAC1128TGG); P239W (CCA715TGG) |
| 39328-62 | Y35W (TAC103TGG); Y72W (TAC214TGG); Y116W (TAC316TGG); P137W (CCT409TGG); Y158W (TAT472TGG); Y172W (TAC514TGG) Y330W (TAC988TGG); Y411W (TAC1128TGG); Y249W (TAT745TGG) |
| 39328-63 | Y35W (TAC103TGG); Y72W (TAC214TGG); Y116W (TAC316TGG); P137W (CCT409TGG); Y158W (TAT472TGG); Y172W (TAC514TGG) Y330W (TAC988TGG); Y411W (TAC1128TGG); P265W (CCA793TGG) |
| 39328-64 | Y35W (TAC103TGG); Y72W (TAC214TGG); Y116W (TAC316TGG); P137W (CCT409TGG); Y158W (TAT472TGG); Y172W (TAC514TGG) Y330W (TAC988TGG); Y411W (TAC1128TGG); P324W (CCT970TGG) |
| 39328-65 | Y35W (TAC103TGG); Y72W (TAC214TGG); Y116W (TAC316TGG); P137W (CCT409TGG); Y158W (TAT472TGG); Y172W (TAC514TGG) Y330W (TAC988TGG); Y411W (TAC1128TGG); Y346W (TAT1036TGG) |
| 39328-66 | Y35W (TAC103TGG); Y72W (TAC214TGG); Y116W (TAC316TGG); P137W (CCT409TGG); Y158W (TAT472TGG); Y172W (TAC514TGG) Y330W (TAC988TGG); Y411W (TAC1128TGG); P265W (CCA793TGG); Y346W (TAT1036TGG) |

As an example of how the β-conglycinin β subunit coding sequence is modified to contain multiple tryptophan substitutions, a description of the generation of mutant ID 39328-57 follows: Plasmid pMON39328 is denatured by mixing 2 μg of DNA with 2M NaOH and 2 mM EDTA and incubating at room temperature for 10 minutes. Next, the the denatured template DNA is precipitated by adding 10 μl of 3 M sodium acetate (pH, 5.2) and 75 μl of 100% ethanol. After centrifugation, the DNA pellet is dissolved in 100 μl of TE buffer. The denatured DNA is immediately hybridized with the mutagenic primers as follows: 10 μl denatured pMON39328 is mixed with 1 μl top selection primer (2.9 ng/μl, from the kit), 1.25 pmol each of the following mutagenic primers, SEQ ID NO: 16, SEQ ID NO: 21, SEQ ID NO: 19, SEQ ID NO: 20, SEQ ID NO: 22, SEQ ID NO: 23, SEQ ID NO: 24, SEQ ID NO: 26, SEQ ID NO: 27, SEQ ID NO: 28, SEQ ID NO: 29, SEQ ID NO: 30, and SEQ ID NO: 32, 2 μl annealing 10×buffer and ddH20 in a 20 μl reaction. The reaction is heated at 75° C. for 5 minutes, then cooled slowly to 37° C. on the bench-top. The mutant strand is synthesized (and nicks in the newly synthesized DNA strand are ligated) in a 20 μl reaction containing 5 μl deionized water, 3 μl synthesis 10×buffer, 1 μl T4 DNA polymerase (5–10 U), and 1 μl DNA ligase (1–3 U). The reaction is carried out for 90 minutes at 37° C. Next, 1.5 μl of the reaction is transformed into E. coli strain BMH71-18 mutS (Promega Corporation, Madison, Wis.), and transformed cells are grown in 4 ml of LB containing 50 μl of GeneEditor Antibiotic Selection Mix (Promega Corporation, Madison, Wis.). Plasmid DNA is isolated (using Qiagen Miniprep Kit, Qiagen Inc. Valencia, Calif.) from a 1.5 ml aliquot of this culture. The isolated plasmid DNA is subsequently transformed into E. coli strain JM109, and individual colonies are grown on LB agar plates containing 125 μg/ml ampicillin and 50 μl of GeneEditor Antibiotic Selection Mix (Promega Corporation, Madison, Wis.). Plasmid DNA is isolated from 10 colonies (Qiagen Miniprep Kit, Qiagen Inc., Valencia, Calif.) and the sequence of the β-conglycinin β subunit coding region is determined. One of these sequences is identified as mutant ID 39328-32. Using 39328-32 as a template, a second round of mutagenesis is carried out using the following primers: SEQ ID NO: 20, SEQ ID NO: 25, SEQ ID NO: 28, SEQ ID NO: 31 and SEQ ID NO: 32. All the procedures are the same as described previously. Mutant ID 39328-57 is identified among the mutants generated during this round.

Example 8

Modification of the β-Conglycinin β Subunit Sequence to Encode Increased Levels of Isoleucine Site-directed mutagenesis reactions are carried out with the intention of substituting isoleucine codons at one or more of the following positions in the β-conglycinin β subunit coding sequence: N32; L36; F46; G51; L56; F59; Q65; L66; Y72; R73; V75; Q76; L85; H88; F94; L95; L96; F97; V98; L99; R102; L105; L107; N117; L118; D121; Q124; R125; P127; Y132; Y133; L134; V135; P137; L143; K147; L148; P151; Y158; F162; Q169; L173; L181; V209; P239; F240; P247; F256; E258; T264; P265; L267; F273; L274; L285; L286; H288; N290; V295; L297; V298; N300; L308; V309; K317; K319; P324; L334; V339; F340; V341; Y346; F348; V350; L356; F358; L359; F361; N368; F372; F393; Y411; F412; and V413.

The primers used in these reactions are listed in the table below, with sequence ID numbers and corresponding amino acid and codon subsititutions given in the right column, with notation according to that given in Example 7:

Primer Sequence for Each Isoleucine Substitution

| Sequence ID | Substitution Sites |
|---|---|
| SEQ ID NO:34 | N32I (AAC94ATT) |
| SEQ ID NO:35 | F36I (TTG106ATT) |
| SEQ ID NO:36 | G51I (GGT151ATT) |
| SEQ ID NO:37 | L56I (CTC166ATT) |
| SEQ ID NO:38 | L66I (CTT196ATT) |
| SEQ ID NO:39 | R73I (CGG217ATT) |
| SEQ ID NO:40 | V75I (GTC223ATT)/Q76I (CAG226ATT) |
| SEQ ID NO:41 | Q76I (CAG226ATT) |
| SEQ ID NO:42 | F77I (TTT229ATT) |
| SEQ ID NO:43 | L85I (CTT253ATT) |
| SEQ ID NO:44 | H88I (CAC262ATT) |
| SEQ ID NO:45 | L95I (CTC283ATT) |
| SEQ ID NO:46 | L95I (CTC283ATT)/L96I (CTC286ATT)/F97I (TTT289ATT)/V98I (GTC292ATT) |
| SEQ ID NO:47 | L99I (CTT295ATT) |
| SEQ ID NO:48 | R102I (AGA304ATT) |
| SEQ ID NO:49 | L105I (CTT313ATT) |
| SEQ ID NO:50 | L107I (TTG319ATT) |
| SEQ ID NO:51 | N117I (AAC349ATT) |
| SEQ ID NO:52 | L118I (CTT352ATT) |
| SEQ ID NO:53 | D122I (GAT364ATT) |
| SEQ ID NO:54 | Q124I (CAG370ATT) |
| SEQ ID NO:55 | L134I (TTG400ATT)/V135I (GTT403ATT) |
| SEQ ID NO:56 | P137I (CCT409ATT) |
| SEQ ID NO:57 | K147I (AAA439ATT) |
| SEQ ID NO:58 | L148I (CTT442ATT) |
| SEQ ID NO:59 | P151I (CCC451ATT) |
| SEQ ID NO:60 | V209I (GTG625ATT) |
| SEQ ID NO:61 | P247I (CCC739ATT) |
| SEQ ID NO:62 | F256I (TTC766ATT) |
| SEQ ID NO:63 | N264I (AAC790ATT)/P265I (CCA793ATT) |
| SEQ ID NO:64 | L267I (CTT799ATT) |
| SEQ ID NO:65 | L285I (CTT853ATT) |
| SEQ ID NO:66 | L285I (CTT853ATT)/L286I (CTA856ATT) |
| SEQ ID NO:67 | N290I (AAT868ATT) |
| SEQ ID NO:68 | L297I (CTA889ATT) |
| SEQ ID NO:69 | L297I (CTA889ATT)/V298I (GTG892ATT) |
| SEQ ID NO:70 | N300I (AAT898ATT) |

-continued

Primer Sequence for Each Isoleucine Substitution

| Sequence ID | Substitution Sites |
|---|---|
| SEQ ID NO:71 | L308I (CTT922ATT) |
| SEQ ID NO:72 | P324I (CCT970ATT) |
| SEQ ID NO:73 | L334I (TTG1000ATT) |
| SEQ ID NO:74 | V339I (GTA1015ATT) |
| SEQ ID NO:75 | V339I (GTA1015ATT)/F340I (TTT1018ATT) |
| SEQ ID NO:76 | F348I (TTT1042ATT) |
| SEQ ID NO:77 | V350I (GTC1048ATT) |
| SEQ ID NO:78 | L356I (CTC1066ATT) |
| SEQ ID NO:79 | L359I (CTT1075ATT) |
| SEQ ID NO:80 | F358I (TTC1072ATT)/L359I (CTT1075ATT)/F361I (TTT1081ATT) |
| SEQ ID NO:81 | N368I (AAC1102ATT) |
| SEQ ID NO:82 | F412I (TTT1234ATT) |
| SEQ ID NO:83 | V413I (GTT126ATT) |

Figure 3:
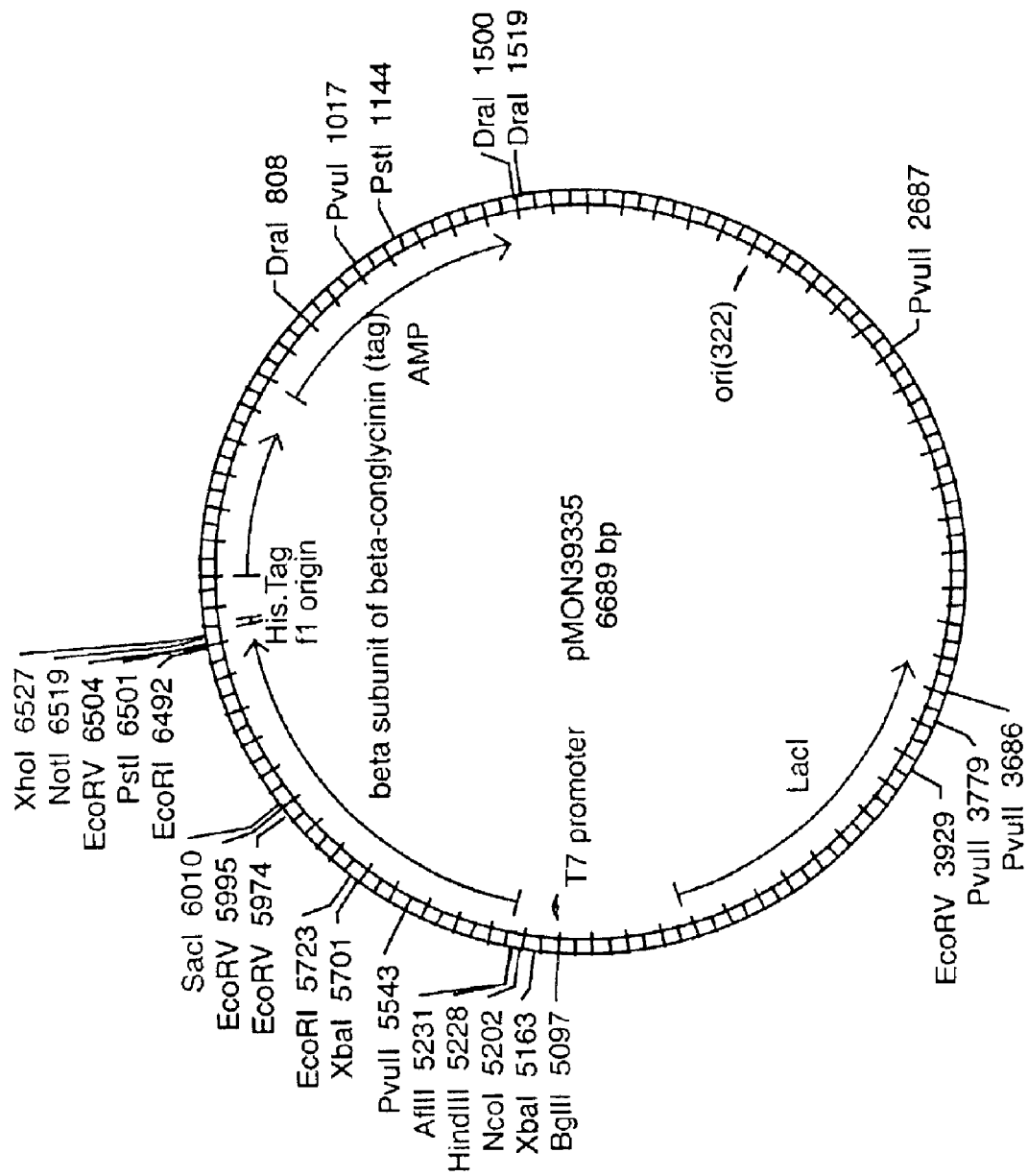
FIG. 3 is a map of pMON39335.

Mutant IDs 39328-67 through 39328-74 are made using pMON39328 as a template, and mutant IDs 39335-1 through 39335-81 are made by using pMON39335 as a template. Plasmid pMON39335 is identical to pMON39328, except that nucleotides encoding Leu24 in the β-conglycinin β subunit protein sequence (SEQ ID NO: 1) are mutated from TTA to CTT to create an AflIII restriction enzyme site. pMON39335 is shown in FIG. 3.

All of the mutants are made using the GeneEditor™ in vitro Site-Directed Mutagenesis System Kit (Promega Corporation, Madison, Wis.) essentially following the manufacturer's instructions. Each mutagenic primer is designed to incorporate nucleotides encoding an isoleucine residue at those positions listed above. Primers are obtained from Invitrogen (Invitrogen, Carlsbad, Calif.), and are phosphorylated at the 5' end and purified by polyacrylamide gel electrophoresis. Detailed mutagenesis procedures are the same as described above in Example 7 for introducing tryptophan substitutions.

The isoleucine mutants and the sites of mutation are given in the table below, with notation as given above in Example 7:

| Mutant ID | AA Substitution (Codon Substitution) |
|---|---|
| 39328-67 | D122I (GAT364ATT); P151I (CCC451ATT); P247I (CCC739ATT); N290I (AAT868ATT); N368I (AAC1102ATT) |
| 39328-68 | N32I (AAC94ATT); D122I (GAT364ATT); P151I (CCC451ATT); P247I (CCC739ATT); N264I (AAC790ATT); P265I (CCA793ATT); N290I (AAT868ATT); P324I (CCT970ATT); N368I (AAC1102ATT) |
| 39328-69 | D122I (GAT364ATT); P151I (CCC451ATT); P247I (CCC739ATT); N368I (AAC1102ATT) |
| 39328-70 | D122I (GAT364ATT); P247I (CCC739ATT); N290I (AAT868ATT); N368I (AAC1102ATT) |
| 39328-71 | P151I (CCC45IATT); P247I (CCC739ATT); N290I (AAT868ATT); N368I (AAC1102ATT) |
| 39328-72 | N32I (AAC94ATT); P151I (CCC451ATT); P247I (CCC739ATT); N264I (AAC790ATT); P265I (CCA793ATT); N290I (AAT868ATT); P324I (CCT970ATT); N368I (AAC1102ATT) |
| 39328-73 | P151I (CCC451ATT); P247I (CCC739ATT); N264I (AAC790ATT); P265I (CCA793ATT); N290I (AAT868ATT); P324I (CCT970ATT); N368I (AAC1102ATT) |
| 39328-74 | N32I (AAC94ATT); D122I (GAT364ATT); P247I (CCC739ATT) N264I (AAC790ATT); P265I (CCA793ATT); N290I (AAT868ATT); N368I (AAC1102ATT) |
| 39335-1 | L56I (CTC166ATT); L85I (CTT253ATT); N117I (AAC349ATT); K147I (AAA439ATT); V209I (GTG625ATT); F256I (TTC766ATT); N264I (AAC790ATT); P265I (CCA793ATT); L297I (CTA889ATT); V298I (GTG892ATT); L308I (CTT922ATT); P324I (CCT970ATT); F348I (TTT1042ATT); L356I (CTC1066ATT); N368I (AAC1102ATT); F412I (TTT1234ATT) |

-continued

| Mutant ID | AA Substitution (Codon Substitution) |
|---|---|
| 39335-2 | L56I (CTC166ATT); R73I (CGG217ATT); L85I (CTT253ATT); L95I (CTC283ATT); N117I (AAC349ATT); K147I (AAA439ATT) V209I (GTG625ATT); N264I (AAC790ATT); P265I (CCA793ATT); F348I (TTT1042ATT); L356I (CTC1066ATT); N368I (AAC1102ATT); F412I (TTT1234ATT) |
| 39335-3 | N32I (AAC94ATT); L56I (CTC166ATT); R73I (CGG217ATT); H88I (CAC262ATT); P151I (CCC451ATT); V209I (GTG625ATT); P247I (CCC739ATT); N300I (AAT898ATT) |
| 39335-4 | N32I (AAC94ATT); L56I (CTC166ATT); R73I (CGG217ATT); H88I (CAC262ATT); D122I (GAT364ATT); P137I (CCT409ATT) P151I (CCC451ATT); V209I (GTG625ATT); N300I (AAT898ATT) |
| 39335-5 | N32I (AAC94ATT); L56I (CTC166ATT); R73I (CGG217ATT); Q76I (CAG226ATT); H88I (CAC262ATT) P151I (CCC451ATT); V209I (GTG625ATT); N300I (AAT898ATT) |
| 39335-6 | N32I (AAC94ATT); L56I (CTC166ATT); R73I (CGG217ATT); H88I (CAC262ATT); D122I (GAT364ATT); P137I (CCT409ATT) P151I (CCC451ATT); V209I (GTG625ATT); P247I (CCC739ATT); N264I (AAC790ATT); P265I (CCA793ATT); N300I (AAT898ATT) |
| 39335-7 | L56I (CTC166ATT); L85I (CTT253ATT); L95I (CTC283ATT); L134I (TTG400ATT); V135I (GTT403ATT); F256I (TTC766ATT) |
| 39335-8 | L56I (CTC166ATT); L85I (CTT253ATT); L95I (CTC283ATT); L105I (CTT313ATT); L134I (TTG400ATT); V135I (GTT403ATT); F256I (TTC766ATT) |
| 39335-9 | L56I (CTC166ATT); L95I (CTC283ATT); L105I (CTT313ATT); L134I (TTG400ATT); V135I (GTT403ATT); F256I (TTC766ATT) |
| 39335-10 | L56I (CTC166ATT); R73I (CGG217ATT); L95I (CTC283ATT); L96I (CTC286ATT); L97I (TTT289ATT); L98I (GTC292ATT); D122I (GAT364ATT); L134I (TTG400ATT); V135I (GTT403ATT); L148I (CTT442ATT); F256I (TTC766ATT); L308I (CTT922ATT) F412I (TTT1234ATT) |
| 39335-11 | L36I (TTG106ATT); L56I (CTC166ATT); R73I (CGG217ATT); L85I (CTT253ATT); L95I (CTC283ATT); L96I (CTC286ATT) L97I (TTT289ATT); L98I (GTC292ATT); D122I (GAT364ATT); L134I (TTG400ATT); V135I (GTT403ATT); L148I (CTT442ATT); L308I (CTT922ATT); F412I (TTT1234ATT) |
| 39335-12 | L56I (CTC166ATT); R73I (CGG217ATT); L85I (CTT253ATT); L95I (CTC283ATT); L96I (CTC286ATT); L97I (TTT289ATT); L98I (GTC292ATT); L134I (TTG400ATT); V135I (GTT403ATT); L148I (CTT442ATT); F256I (TTC766ATT); L308I (CTT922ATT); F412I (TTT1234ATT) |
| 39335-13 | L56I (CTC166ATT); L85I (CTT253ATT); L95I (CTC283ATT); L96I (CTC286ATT); L97I (TTT289ATT); L98I (GTC292ATT) L118I (CTT352ATT); F256I (TTC766ATT); L148I (CTT442ATT); |
| 39335-14 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT); |
| 39335-15 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); F256I (TTC766ATT); L148I (CTT442ATT); |
| 39335-16 | L36I (TTG106ATT); G51I (GGT151ATT); L56I (CTC166ATT); L66I (CTT196ATT); R73I (CGG217ATT); L85I (CTT253ATT); L95I (CTC283ATT); L96I (CTC286ATT); L97I (TTT289ATT); L98I (GTC292ATT); D122I (GAT364ATT); L134I (TTG400ATT); V135I (GTT403ATT); L148I (CTT442ATT); L308I (CTT922ATT); F412I (TTT1234ATT) |
| 39335-17 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); L274I (CTC820ATT); L308I (CTT922ATT); F77I (TTT229ATT); L285I (CTT853ATT); V339I (GTA1015ATT); F340I (TTT1018ATT); F358I (TTC1072ATT); L359I (CTT1075ATT); F361I (TTT1081ATT) |
| 39335-18 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); L274I (CTC820ATT); L308I (CTT922ATT); |
| 39335-19 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); L274I (CTC820ATT); L308I (CTT922ATT); F77I (TTT229ATT); L285I (CTT853ATT); V339I (GTA1015ATT); F340I (TTT1018ATT); F358I (TTC1072ATT); L359I (CTT1075ATT); F361I (TTT1081ATT); L105I (CTT313ATT) |
| 39335-20 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); L274I (CTC820ATT); L308I (CTT922ATT); F77I (TTT229ATT); L285I (CTT853ATT); L105I (CTT313ATT); |
| 39335-21 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F77I (TTT229ATT); L285I (CTT853ATT); L308I (CTT922ATT); V350I (GTC1048ATT) |
| 39335-22 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); L274I (CTC820ATT); L308I (CTT922ATT); F77I (TTT229ATT); L285I (CTT853ATT); V339I |

| Mutant ID | AA Substitution (Codon Substitution) |
|---|---|
| | (GTA1015ATT); F340I (TTT1018ATT); L105I (CTT313ATT); L107I (TTG319ATT); V350I (GTC1048ATT) |
| 39335-23 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); F77I (TTT229ATT); L105I (CTT313ATT) F358I (TTC1072ATT); L359I (CTT1075ATT); F361I (TTT1081ATT) |
| 39335-25 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); L274I (CTC820ATT); L308I (CTT922ATT); L105I (CTT313ATT); L285I (CTT853ATT) |
| 39335-26 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F358I (TTC1072ATT); L359I (CTT1075ATT); F361I (TTT1081ATT); V339I (GTA1015ATT); F340I (TTT1018ATT) |
| 39335-27 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); L274I (CTC820ATT); L308I (CTT922ATT); F77I (TTT229ATT); L105I (CTT313ATT); L285I (CTT853ATT); V350I (GTC1048ATT); V339I (GTA1015ATT); F340I (TTT1018ATT) |
| 39335-28 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); L274I (CTC820ATT); L308I (CTT922ATT); L105I (CTT313ATT); L285I (CTT853ATT); F358I (TTC1072ATT); L359I (CTT1075ATT); F361I (TTT1081ATT) |
| 39335-29 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (GTT442ATT) F256I (TTC766ATT); L274I (CTC820ATT); L308I (CTT922ATT); L285I (CTT853ATT); F358I (TTC1072ATT); L359I (CTT1075ATT); F361I (TTT1081ATT) |
| 39335-30 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) V350I (GTC1048ATT) |
| 39335-31 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); L274I (CTC820ATT); L308I (CTT922ATT); L105I (CTT313ATT); L107I (TTG319ATT); L285I (CTT853ATT); V350I (GTC1048ATT); V339I (GTA1015ATT); F340I (TTT1018ATT) |
| 39335-33 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F358I (TTC1072ATT); L359I (CTT1075ATT); F361I (TTT1081ATT) |
| 39335-34 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) V339I (GTA1015ATT); F340I (TTT1018ATT) |
| 39335-35 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F256I (TTC766ATT); F77I (TTT229ATT); L105I (CTT313ATT); L107I (TTG319ATT) |
| 39335-36 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); L285I (CTT853ATT); L274I (CTC820ATT); L308I (CTT922ATT); V350I (GTC1048ATT) |
| 39335-37 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F77I (TTT229ATT) |
| 39335-38 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L285I (CTT853ATT) |
| 39335-39 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F77I (TTT229ATT); L105I (CTT313ATT) |
| 39335-40 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT) |
| 39335-41 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F77I (TTT229ATT); V339I (GTA1015ATT); F340I (TTT1018ATT); F358I (TTC1072ATT); L359I (CTT1075ATT); F361I (TTT1081ATT) |
| 39335-42 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F77I (TTT229ATT); Q124I (CAG370ATT); F256I (TTC766ATT); V339I (GTA1015ATT); F340I (TTT1018ATT) |
| 39335-43 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F256I (TTC766ATT); |

-continued

| Mutant ID | AA Substitution (Codon Substitution) |
|---|---|
| | V339I (GTA1015ATT); F340I (TTT1018ATT); F358I (TTC1072ATT); L359I (CTT1075ATT); F361I (TTT1081ATT) |
| 39335-44 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L274I (CTC820ATT); L308I (CTT922ATT); V339I (GTA1015ATT); F340I (TTT1018ATT); F77I (TTT229ATT) F358I (TTC1072ATT); L359I (CTT1075ATT); F361I (TTT1081ATT) |
| 39335-45 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L274I (CTC820ATT); L308I (CTT922ATT); V339I (GTA1015ATT); F340I (TTT1018ATT); F77I (TTT229ATT) L105I (CTT313ATT); L107I TTG319ATT); Q124I (CAG370ATT) |
| 39335-46 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L274I (CTC820ATT); V339I (GTA1015ATT); F340I (TTT1018ATT); F77I (TTT229ATT); L105I (CTT313ATT); L107I (TTG319ATT); F358I (TTC1072ATT); L359I (CTT1075ATT); F361I (TTT1081ATT) |
| 39335-47 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) Q124I (CAG370ATT); F77I (TTT229ATT); F358I (TTC1072ATT); L359I (CTT1075ATT); F361I (TTT1081ATT) |
| 39335-48 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); F358I (TTC1072ATT); L359I (CTT1075ATT); F361I (TTT1081ATT) |
| 39335-49 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L274I (CTC820ATT); V339I (GTA1015ATT); F340I (TTT1018ATT); F358I (TTC1072ATT); L359I (CTT1075ATT); F361I (TTT1081ATT) |
| 39335-50 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L308I (CTT922ATT); V339I (GTA1015ATT); F340I (TTT1018ATT); F358I (TTC1072ATT); L359I (CTT1075ATT); F361I (TTT1081ATT) |
| 39335-51 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT) F358I (TTC1072ATT); L359I (CTT1075ATT); F361I (TTT1081ATT) |
| 39335-52 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT); V350I (GTC1048ATT) |
| 39335-53 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); F77I (TTT229ATT); Q124I (CAG370ATT); F358I (TTC1072ATT); L359I (CTT1075ATT); F361I (TTT1081ATT) |
| 39335-54 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); F77I (TTT229ATT); Q124I (CAG370ATT) |
| 39335-55 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); F77I (TTT229ATT); Q124I (CAG370ATT) V339I (GTA1015ATT); V350I (GTC1048ATT); L359I (CTT1075ATT) |
| 39335-56 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); F77I (TTT229ATT); Q124I (CAG370ATT) V339I (GTA1015ATT); F340I (TTT1018ATT); V350I (GTC1048ATT); L359I (CTT1075ATT) F256I (TTC766ATT); L274I (CTC820ATT); F412I (TTT1234ATT) |
| 39335-57 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); F77I (TTT229ATT); Q124I (CAG370ATT) L274I (CTC820ATT); V339I (GTA1015ATT); V350I (GTC1048ATT); L359I (CTT1075ATT) |
| 39335-58 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); F77I (TTT229ATT); Q124I (CAG370ATT) V339I (GTA1015ATT); |

-continued

| Mutant ID | AA Substitution (Codon Substitution) |
|---|---|
| | F340I (TTT1018ATT); V350I (GTC1048ATT); F358I (TTC1072ATT); L359I (CTT1075ATT); F361I (TTT1081ATT) |
| 39335-59 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT); V350I (GTC1048ATT) L267I (CTT799ATT); L297I (CTA889ATT); L334I (TTG1000ATT) |
| 39335-60 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT); V350I (GTC1048ATT) L267I (CTT799ATT); L297I (CTA889ATT) |
| 39335-61 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT); V350I (GTC1048ATT); L66I (CTT196ATT) |
| 39335-62 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT); V350I (GTC1048ATT); V75I (GTC223ATT); Q76I (CAG226ATT) |
| 39335-63 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT); V350I (GTC1048ATT); L99I (CTT295ATT) |
| 39335-64 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT); V350I (GTC1048ATT); L285I (CTT853ATT); L286I (CTA856ATT) |
| 39335-65 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L105I (CTT313ATT); L107I (TTG319ATT); L308I (CTT922ATT); V339I (GTA1015ATT); F340I (TTT1018ATT); Q124I (CAG370ATT); F77I (TTT229ATT); L274I (CTC820ATT); V350I (GTC1048ATT); V413I (GTT1237ATT) |
| 39335-66 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F256I (TTC766ATT); F412I (TTT1234ATT) |
| 39335-67 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) G51I (GGT151ATT); L66I (CTT196ATT); L297I (CTA889ATT); V339I (GTA1015ATT); F340I (TTT1018ATT); F358I (TTC1072ATT); L359I (CTT1075ATT); F361I (TTT1081ATT); F412I (TTT1234ATT) |
| 39335-68 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) G51I (GGT151ATT); L66I (CTT196ATT); L297I (CTA889ATT); V339I (GTA1015ATT); F340I (TTT1018ATT); L267I (CTT799ATT); F358I (TTC1072ATT); L359I (CTT1075ATT); F361I (TTT1081ATT); F412I (TTT1234ATT) |
| 39335-69 | G51I (GGT151ATT); L66I (CTT196ATT); L297I (CTA889ATT); F36I (TTG106ATT); L267I (CTT799ATT); F412I (TTT1234ATT) |
| 39335-70 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L66I (CTT196ATT); L105I (CTT313ATT), L107I (TTG319ATT); L267I (CTT799ATT) V339I (GTA1015ATT); F340I (TTT1018ATT); F358I (TTC1072ATT); L359I (CTT1075ATT); F361I (TTT1081ATT) |
| 39335-71 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L66I (CTT196ATT); L267I (CTT799ATT); V339I (GTA1015ATT); F340I (TTT1018ATT); F358I (TTC1072ATT); L359I (CTT1075ATT); F361I (TTT1081ATT) |
| 39335-72 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L66I (CTT196ATT) |
| 39335-73 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L267I (CTT799ATT) |
| 39335-74 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) F412I (TTT1234ATT) |

-continued

| Mutant ID | AA Substitution (Codon Substitution) |
|---|---|
| 39335-75 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L297I (CTA889ATT) |
| 39335-76 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) L334I (TTG1000ATT) |
| 39335-77 | L56I (CTC166ATT); L85I (CTT253ATT); L95I (CTC283ATT); L96I (CTC286ATT); L97I (TTT289ATT); L98I (GTC292ATT); L118I (CTT352ATT); L134I (TTG400ATT); V135I (GTT403ATT); L148I (CTT442ATT) G51I (GGT151ATT) |
| 39335-78 | F36I (TTG106ATT); G51I (GGT151ATT); L56I (CTC166ATT); L66I (CTT196ATT); R73I (CGG217ATT); F77I (TTT229ATT); L85I (CTT253ATT); L95I (CTC283ATT); L96I (CTC286ATT); L97I (TTT289ATT); L98I (GTC292ATT); L118I (CTT352ATT); D122I (GAT364ATT); Q124I (CAG370ATT); L134I (TTG400ATT); V135I (GTT403ATT); L148I (CTT442ATT); F256I (TTC766ATT); L267I (CTT799ATT); L285I (CTT853ATT); L297I (CTA889ATT); L308I (CTT922ATT); V339I (GTA1015ATT); F340I (TTT(1018ATT); F412I (TTT1234ATT) L105I (CTT313ATT); L107I (TTG319ATT) L274I (CTC820ATT); F358I (TTC1072ATT); L359I (CTT1075ATT); F361I (TTT1081ATT) |
| 39335-79 | F36I (TTG106ATT); G51I (GGT151ATT); L56I (CTC166ATT); L66I (CTT196ATT); R73I (CGG217ATT); F77I (TTT229ATT); L85I (CTT253ATT); L95I (CTC283ATT); L96I (CTC286ATT); L97I (TTT289ATT); L98I (GTC292ATT); L118I (CTT352ATT); D122I (GAT364ATT); Q124I (CAG370ATT); L134I (TTG400ATT); V135I (GTT403ATT); L148I (CTT442ATT); F256I (TTC766ATT); L267I (CTT799ATT); L285I (CTT853ATT); L297I (CTA889ATT); L308I (CTT922ATT); V339I (GTA1015ATT); F340I (TTT(1018ATT); F412I (TTT1234ATT) |
| 39335-80 | F36I (TTG106ATT); G51I (GGT151ATT); L56I (CTC166ATT); L66I (CTT196ATT); R73I (CGG217ATT); F77I (TTT229ATT); L85I (CTT253ATT); L95I (CTC283ATT); L96I (CTC286ATT); L97I (TTT289ATT); L98I (GTC292ATT); L118I (CTT352ATT); D122I (GAT364ATT); Q124I (CAG370ATT); L134I (TTG400ATT); V135I (GTT403ATT); L148I (CTT442ATT); F256I (TTC766ATT); L267I (CTT799ATT); L285I (CTT853ATT); L297I (CTA889ATT); L308I (CTT922ATT); V339I (GTA1015ATT); F340I (TTT(1018ATT); F412I (TTT1234ATT) F358I (TTC1072ATT); L359I (CTT1075ATT); F361I (TTT1081ATT) |
| 39335-81 | F36I (TTG106ATT); G51I (GGT151ATT); L56I (CTC166ATT); L66I (CTT196ATT); R73I (CGG217ATT); F77I (TTT229ATT); L85I (CTT253ATT); L95I (CTC283ATT); L96I (CTC286ATT); L97I (TTT289ATT); L98I (GTC292ATT); L118I (CTT352ATT); D122I (GAT364ATT); Q124I (CAG370ATT); L134I (TTG400ATT); V135I (GTT403ATT); L148I (CTT442ATT); F256I (TTC766ATT); L267I (CTT799ATT); L285I (CTT853ATT); L297I (CTA889ATT); L308I (CTT922ATT); V339I (GTA1015ATT); F340I (TTT(1018ATT); F412I (TTT1234ATT) L274I (CTC820ATT); F358I (TTC1072ATT); L359I (CTT1075ATT); F361I (TTT1081ATT) |

As an example of how the β-conglycinin β subunit coding sequence is modified to contain multiple isoleucine substitutions, a description of the generation of mutant ID 39328-14 follows: Double-stranded plasmid pMON39335 is denatured and hybridized with the following mutagenic primers SEQ ID NO: 37, SEQ ID NO: 43, SEQ ID NO: 46, SEQ ID NO: 52, SEQ ID NO: 55, SEQ ID NO: 58 and SEQ ID NO: 62. An aliquot of the mutagenesis reaction is transformed into E. coli strain BMH 71-18 mutS, and plasmids isolated from cells resistant to the GeneEditor Antibiotic Selection Mix (Promega Corporation, Madison, Wis.) are then transformed into E. coli strain JM109. Mutant ID 39335-14 is one of the modified forms identified when plasmid DNA from transformants is sequenced.

As another example of modification of the β-conglycinin β subunit coding sequence to contain multiple isoleucine substitutions, a description of the generation of mutant ID 39328-33, using mutant ID 39335-14 as a template, follows: Before the plasmid (pMON39334-14) containing mutant ID 39335-14 could be used as a template for a second round of mutagenesis, the GeneEditor (Promega Corporation, Madison, Wis.) antibiotic mix-sensitive form of the ampicillin-resistance gene had to be restored (it is converted to the GeneEditor resistant form during the first round of mutagenesis). To accomplish this, the coding sequence for mutant ID 39335-14 is excised from pMON39335-14 on a 1.4 kb DNA fragment, and is used to replace the β subunit coding sequence in pMON39335. The resulting plasmid is used as a template in a mutagenesis reaction (as described above) using mutagenic primer SEQ ID NO: 80, resulting in the identification of mutant ID 39335-33.

Example 9

Confirmation that the β-Conglycinin β Subunit, Modified to Contain 1 or More Tryptophan or Isoleucine Residues, Folds and Self-Assembles in E. coli This example sets forth confirmation of the protein structure from the expression of modified β-conglycinin β subunit clones. The assembly properties of the following modified forms of the β subunit (indicated by mutant ID number), each containing a different tryptophan substitution, are determined as described in Example 6. Western blot analysis of sucrose gradient fractions is carried out as in Example 6 using anti-FLAG antibody. Results are shown in the tables below.

E. coli Assembly Results for Ile Mutants

| Mutant ID. | E. coli Assembly Results |
| --- | --- |
| 39328-67 | undefined |
| 39328-68 | undefined |
| 39335-1 | monomer |
| 39335-2 | monomer |
| 39335-3 | monomer |
| 39335-4 | undefined |
| 39335-5 | undefined |
| 39335-6 | monomer |
| 39335-7 | trimer |
| 39335-8 | trimer |
| 39335-9 | trimer |
| 39335-10 | monomer |
| 39335-11 | monomer |
| 39335-12 | monomer |
| 39335-13 | monomer |
| 39335-14 | trimer |
| 39335-15 | trimer |
| 39335-17 | monomer |
| 39335-18 | trimer |
| 39335-19 | monomer |
| 39335-20 | monomer |
| 39335-21 | monomer |
| 39335-22 | monomer |
| 39335-23 | monomer and trimer |
| 39335-24 | monomer and trimer |
| 39335-25 | monomer |
| 39335-26 | monomer |
| 39335-27 | monomer |
| 39335-28 | monomer |
| 39335-29 | monomer |
| 39335-30 | trimer |
| 39335-31 | monomer |
| 39335-32 | monomer |
| 39335-33 | trimer |
| 39335-34 | trimer |
| 39335-35 | trimer |
| 39335-36 | monomer |
| 39335-37 | trimer |
| 39335-38 | monomer |
| 39335-39 | trimer |
| 39335-40 | trimer |
| 39335-41 | monomer and trimer |
| 39335-42 | monomer |
| 39335-43 | monomer |
| 39335-44 | monomer and trimer |
| 39335-45 | monomer and trimer |
| 39335-46 | monomer |
| 39335-47 | monomer and trimer |
| 39335-48 | monomer and trimer |
| 39335-49 | monomer |
| 39335-50 | monomer and trimer |
| 39335-51 | monomer |
| 39335-52 | monomer and trimer |
| 39335-53 | monomer and trimer |
| 39335-54 | monomer and trimer |
| 39335-55 | monomer and trimer |
| 39335-56 | monomer |
| 39335-57 | monomer |
| 39335-58 | monomer and trimer |
| 39335-59 | monomer and trimer |
| 39335-60 | monomer and trimer |
| 39335-61 | monomer and trimer |
| 39335-62 | monomer and trimer |
| 39335-64 | monomer |
| 39335-65 | monomer and trimer |
| 39335-66 | monomer |
| 39335-67 | monomer |
| 39335-68 | monomer |
| 39335-69 | monomer |
| 39335-70 | monomer |
| 39335-71 | monomer |
| 39335-72 | monomer and trimer |
| 39335-73 | trimer |
| 39335-74 | monomer |
| 39335-75 | trimer |
| 39335-76 | monomer and trimer |
| 39335-77 | monomer |
| 39335-78 | monomer |
| 39335-79 | monomer |
| 39335-80 | monomer |
| 39335-81 | monomer |

E. coli Assembly Results for Trp Mutants

| Mutant ID. | E. coli Assembly Results |
| --- | --- |
| 39328-1 | trimer |
| 39328-2 | trimer |
| 39328-3 | monomer and trimer |
| 39328-4 | trimer |
| 39328-5 | trimer |
| 39328-6 | trimer |
| 39328-7 | trimer |
| 39328-8 | trimer |
| 39328-9 | trimer |
| 39328-10 | trimer |
| 39328-11 | trimer |
| 39328-12 | trimer |
| 39328-13 | trimer |
| 39328-14 | trimer |
| 39328-15 | trimer |
| 39328-16 | trimer |
| 39328-20 | trimer |
| 39328-23 | trimer |
| 39328-24 | trimer |
| 39328-25 | trimer |
| 39328-27 | monomer |
| 39328-32 | monomer and trimer |
| 39328-36 | monomer |
| 39328-37 | trimer |
| 39328-38 | undefined |
| 39328-39 | undefined |
| 39328-40 | undefined |
| 39328-47 | trimer |
| 39328-51 | undefined |
| 39328-57 | trimer |
| 39328-58 | undefined |
| 39328-59 | monomer |
| 39328-60 | monomer and trimer |
| 39328-61 | undefined |
| 39328-62 | undefined |
| 39328-63 | monomer |
| 39328-64 | monomer and trimer |
| 39328-65 | monomer |

Example 10

This example sets forth confirmation that a β-conglycinin β subunit, modified to contain multiple isoleucine residues, accumulates in the seeds of transformed plants.

Vector Construction

DNA sequences corresponding to the coding sequence of epitope (FLAG)-tagged β-conglycinin β subunit, and to the coding sequences of mutants 39335-14, 39335-41, 39335-58 and 39335-78 (SEQ ID NOs: 84–87, respectively, described above) were modified by placing the coding sequence for the first 25 residues of the β subunit upstream of the coding sequence for the FLAG epitope. The addition of these 25 residues restored the β subunit signal peptide, and targets the modified β-conglycinin β subunit to the protein storage vacuole in plant seeds. The resulting coding sequences were then cloned into a plant transformation vector under the control of the arcelin 5 promoter.

By way of example, the cloning technique used to generate pMON64015 is described briefly herein. The plasmid pMON39335-41 was digested with HindIII and PstI. The resulting 1.27 kb fragment, containing the β-conglycinin β subunit coding sequence with 16 isoleucine substitutions, was isolated from an agarose gel following electrophoresis. A shuttle vector, pMON68006, containing the Arcelin5 Promoter-FLAG-β CG-10-Ile-Arc 3'UTR expression cassette was also digested with HindIII and PstI to generate a 5.7 kb fragment. The 5.7 kb fragment lacks the coding sequence for the mature form of the β-conglycinin β subunit, but retains the coding sequence for the arcelin 5 promoter, the β subunit signal peptide, the FLAG epitope, and the arcelin 5 3'UTR. The 5.7 kb fragment was isolated from an agarose gel following electrophoresis. The 1.27 kb fragment from pMON39335-41 and the 5.7 kb fragment were then ligated to generate the vector pMON64017. The Arc5 Promoter-FLAG-β CG-16-Ile-Arc 3'UTR expression cassette was then isolated by digesting pMON64017 with NotI and the resulting 3.8 kb fragment was isolated from an agarose gel following electrophoresis. A plant transformation backbone vector for Agrobacterium mediated transformation, pMON38207, which contains the FMV promoter driving CP4 gene as a selectable marker, was then digested with NotI, and the 3.8 kb fragment from pMON64017 was ligated to generate the plasmid pMON64015.

Using the strategy described above for pMON64015, the following plant transformation vectors were generated:

| Plasmid | Mutant ID | Number of Ile subst. | Promoter |
| --- | --- | --- | --- |
| pMON69616 | wild-type | 0 | Arcelin 5 |
| pMON64016 | 39335-14 | 10 | Arcelin 5 |
| pMON64015 | 39335-41 | 16 | Arcelin 5 |
| pMON64019 | 39335-58 | 21 | Arcelin 5 |
| pMON69621 | 39335-78 | 31 | Arcelin 5 |

The sequences of the transgenes (arcelin 5 promoter-coding sequence-arcelin 5 3' untranslated region) and the corresponding protein coding sequences are given in the sequence listing. To more fully describe the constructs, the following keys corresponding to the nucleotide and amino acid sequences of the plasmids described above, are hereby given.

Description of pMON69616 Cassette DNA Sequence (SEQ ID NO: 88)
Nucleotides 1–3808: Entire expression cassette contained in pMON69616
Nucleotides 1–1161: Truncated Arcelin 5 promoter
Nucleotides 1174–2523: Beta-conglycinin coding sequence containing FLAG epitope
Nucleotides 2550–3808: Arcelin 5 3' untranslated region (UTR)
Description of pMON69616 Beta-Conglycinin Protein Sequence (SEQ ID NO: 89)
Amino acids 1–449: Complete beta-conglycinin coding sequence containing signal peptide and inserted FLAG epitope tag
Amino acids 1–25: First 25 amino acids from wild-type beta-conglycinin, including signal peptide
Amino acids 26–33: FLAG epitope
Amino acids 34–449: Mature form of wild-type (unmodified) beta-conglycinin Description of pMON64016 Cassette DNA Sequence (SEQ ID NO: 90)
Nucleotides 1–3808: Entire expression cassette contained in pMON64016
Nucleotides 1–1161: Truncated Arcelin 5 promoter
Nucleotides 1174–2523: Modified beta-conglycinin coding sequence containing FLAG epitope
Nucleotides 2550–3808: Arcelin 5 3' untranslated region (UTR)
Description of pMON64016 Beta-Conglycinin Protein Sequence (SEQ ID NO: 91)
Amino acids 1–449: Complete modified beta-conglycinin coding sequence containing signal peptide and inserted FLAG epitope tag
Amino acids 1–25: First 25 amino acids from beta-conglycinin, including signal peptide
Amino acids 26–33: FLAG epitope
Amino acids 34–449: Mature form of modified beta-conglycinin containing 10 isoleucine substitutions (corresponds to mutant 39335-14)
Description of pMON64015 Cassette DNA Sequence (SEQ ID NO: 92)
Nucleotides 1–3808: Entire expression cassette contained in pMON64015
Nucleotides 1–1161: Truncated Arcelin 5 promoter
Nucleotides 1174–2523: Modified beta-conglycinin coding sequence containing FLAG epitope
Nucleotides 2550–3809: Arcelin 5 3' untranslated region (UTR)
Description of pMON64015 Beta-Conglycinin Protein Sequence (SEQ ID NO: 93)
Amino acids 1–449: Complete modified beta-conglycinin coding sequence containing signal peptide and inserted FLAG epitope tag
Amino acids 1–25: First 25 amino acids from beta-conglycinin, including signal peptide
Amino acids 26–33: FLAG epitope
Amino acids 34–449: Mature form of modified beta-conglycinin containing 16 isoleucine substitutions (corresponds to mutant 39335-41)
Description of pMON64019 Cassette DNA Sequence (SEQ ID NO: 94)
Nucleotides 1–3808: Entire expression cassette contained in pMON64019
Nucleotides 1–1161: Truncated Arcelin 5 promoter
Nucleotides 1174–2523: Modified beta-conglycinin coding sequence containing FLAG epitope
Nucleotides 2550–3809: Arcelin 5 3' untranslated region (UTR)
Description of pMON64019 Modified Beta-Conglycinin Protein Sequence (SEQ ID NO:95)
Amino acids 1–449: Complete modified beta-conglycinin coding sequence containing signal peptide and inserted FLAG epitope tag
Amino acids 1–25: First 25 amino acids from beta-conglycinin, including signal peptide
Amino acids 26–33: FLAG epitope
Amino acids 34–449: Mature form of modified beta-conglycinin containing 21 isoleucine substitutions (corresponds to mutant 39335-58)
Description of pMON69621 Cassette DNA Sequence (SEQ ID NO: 96)
Nucleotides 1–3808: Entire expression cassette contained in pMON69621
Nucleotides 1–1161: Truncated Arcelin 5 promoter
Nucleotides 1174–2523: Modified beta-conglycinin coding sequence containing FLAG epitope Nucleotides 2550–3809: Arcelin 5 3' untranslated region (UTR)

Description of pMON69621 Beta-Conglycinin Protein Sequence (SEQ ID NO: 97)

Amino acids 1–449: Complete modified beta-conglycinin coding sequence containing signal peptide and inserted FLAG epitope tag Amino acids 1–25: First 25 amino acids from beta-conglycinin, including signal peptide Amino acids 26–33: FLAG epitope Amino acids 34–449: Mature form of modified beta-conglycinin containing 21 isoleucine substitutions (corresponds to mutant 39335-78)

Plant Transformation

Arabidopsis plants were transformed with the vectors described above using standard Agrobacterium tumefaciens-mediated plant transformation methods described by Bechtold et al., (CR Acad Sci Paris Sciences di la vie/life sciences 316: 1194–1199, 1993) or Clough, S. and Bent, A. (The Plant Journal 16(6), 735–743, 1998).

Briefly, Arabidopsis thaliana ecotype Columbia plants, 28–35 days old, are transformed by dipping the secondary bolts and rosettes in a solution of Agrobacterium tumefaciens (ABI) and swirling for 10–20 seconds. The Agrobacterium tumefaciens (ABI) is obtained from an overnight culture grown in YEP (5 g/L sodium chloride, 10 g/L yeast extract and 10 g/L peptone, pH 7.0) and diluted the following morning with inoculation media (5% sucrose plus 0.05% Silwet L77 surfactant) to achieve an optical density reading at 600 nm of about 0.8. Prior to transformation the plants are kept under high humidity conditions for 24 hours using a plant propagation dome, and withholding water for 5 days.

Plants are then grown under standard conditions of watering and fertilizing twice a week using sub-irrigation methods. The bolts are bagged in pollination bags to contain seeds. After the plants have set seed (approximately 4 weeks post dip), they are removed from the water and the seed is allowed to dry down for approximately one week prior to harvest. The seed is then surface sterilized overnight under a chlorine gas atmosphere, and plated onto selective media containing glyphosate (30–50 μM) or planted in soil and sprayed with Roundup Ultra (Monsanto Company, St. Louis, Mo.) to identify positive segregants. Selection plates are cultured for 48 hours at 4° C. and then transferred to a Percival growth chamber set at 23.5° C. (16:8 hour light cycle). Positive segregants with expanded primary and secondary leaves and branched roots are identified in about 18–21 days. The corresponding negative segregants have no expansion of primary and secondary leaves and stunted roots.

Seeds representing the T2 generation are harvested from individual glyphosate-resistant plants. Protein is extracted from seeds using standard techniques known in the art. The extracted protein is then analyzed by western blot analysis. The antiserum used for western blots is isolated from rabbits injected with a modified form (10 isoleucine substitutions with FLAG epitope incorporated at amino terminus) of β-conglycinin β subunit purified from E. coli transformed with pMON39335-14 (Cocalico Biologicals, Inc., Reamstown, Pa.). Wild-type β-conglycinin β subunit, and β subunit representing each modified form, are detected in transgenic seeds, however, the level of accumulation for each form varies. The relative accumulation levels of each form, as determined by examining band intensities on western blots, are summarized in the following table.

| Plasmid | Number of Ile subst. | Level of accumulation in Arabidopsis seeds |
| --- | --- | --- |
| pMON69616 | 0 | ++++ |
| pMON64016 | 10 | +++ |
| pMON64015 | 16 | ++ |
| pMON64019 | 21 | +++ |
| pMON69621 | 31 | + |

Soybean plants are transformed with pMON69616 and pMON64016 using Agrobacterium tumefaciens-mediated plant transformation methods such as described by Martinell et al. in U.S. Pat. No. 6,384,301. Individual seeds from the resulting transgenic plants are analyzed by SDS-PAGE, and by western blot analysis using antibodies that react with the FLAG epitope (Anti-FLAG M2 antibody; Stratagene) or with antiserum that reacts with β-conglycinin β subunit (described above). The epitope (FLAG)-tagged unmodified form and the modified form (10 isoleucine substitutions; mutant 39335-14) both accumulate at levels of more than 7% of total extractable protein as estimated by densitometry of SDS-PAGE gels following staining using a Colloidal Blue Stain Kit (Invitrogen). Densitometry is performed using a Biorad Gel Doc Instrument.

The transgenic seeds expressing modified β subunit (corresponding to mutant 39335-14) are analyzed by SDS-PAGE and visualized using a Colloidal Blue Stain Kit (Invitrogen). The results reveal that expression of the modified protein is correlated with the suppression of one or more of the group of endogenous β-conglycinin subunits (α subunit, α' subunit, β subunit). There is a strong inverse correlation observed between the level of accumulation of modified β subunit and the level of accumulation of endogenous β subunit. Thus, expression of modified β-conglycinin in seeds represents a method of reducing levels of endogenous β-conglycinin.

Example 11

Modification of the β-Conglycinin β Subunit Sequence to Encode Increased Levels of Threonine, Lysine and Methionine Site-directed mutagenesis reactions are carried out with the intention of substituting threonine codons at one or more of the following positions in the β-conglycinin β subunit coding sequence (SEQ ID NO: 1): S54, S225, S250, S251, S75, S90, S202, S16, S38, S139, S149, S197, S385, A65, A67, A78, A98, A124, A258, A279, A307, A327, A335, A268, A340, A367, V83, V284, V324, V186, V375, L171, L348, N275, N326, N346, N92, N216, N280, N332, N35, N168, Q53, Q303, Q32, R304, K201, K230, E276, E282, D68, D135, D89, D253, D389, D313, F136, P262, P62, P222, P318, P240.

Site-directed mutagenesis reactions are carried out with the intention of substituting lysine codons at one or more of the following positions in the β-conglycinin β subunit coding sequence (SEQ ID NO: 1): R169, R194, R243, R361, R377, R37, R357, R304, R45, R132, R179, R199, R205, R883, S75, S202, S13, S210, S329, S371, T328, N84, N117, N225, N339, Q192, Q149, Q241, Q116, Q142, Q145, H153, V363, L379, L300, I155, I208, I223, I286, D89, E157, E166, E191, E365, E376.

Site-directed mutagenesis reactions are carried out with the intention of substituting methionine codons at one or more of the following positions in the β-conglycinin β subunit coding sequence (SEQ ID NO: 1): L41, L156, L242, L245, L188, L379, I167, I193, I208, F34, Y386, N239, Q364, Q241.

All of the mutants are made using the GeneEditor™ in vitro Site-Directed Mutagenesis System Kit (Promega Corporation, Madison, Wis.) essentially following the manufacturer's instructions. Each mutagenic primer is designed to incorporate nucleotides encoding a threonine, lysine or methione residue at those positions listed above. Primers are obtained from Invitrogen (Invitrogen, Carlsbad, Calif.), and are phosphorylated at the 5' end and purified by polyacrylamide gel electrophoresis. Detailed mutagenesis procedures are the same as described above in Example 7 for introducing tryptophan substitutions.

References

Ainley et al., *Plant Mol. Biol.*, 14:949, 1990.
Altschul et al., *Journal of Molecular Biology*, 215:403–410, 1990.
Andreas et al., *Theor. Appl. Genet.*, 72:123–128, 1986.
Ausubel et al., *Current Protocols in Molecular Biology*, John Wiley and Sons, Inc., 1995.
Battraw and Hall, *Plant Sci.*, 86(2):191–202, 1992.
Back et al., *Plant Mol. Biol.*, 17:9, 1991.
Bauer et al., *Gene*, 37:73, 1985.
Becker and Guarente, In: Abelson and Simon (eds.), *Guide to Yeast Genetics and Molecular Biology, Methods Enzymol.*, Vol. 194, pp. 182–187, Academic Press, Inc., New York.
Bennett and LaSure (eds.), *More Gene Manipulations in Fungi*, Academic Press, CA, 1991.
Bent et al., *Science*, 265:1856–1860, 1994.
Bergeron et al., *TIBS*, 19:124–128, 1994.
Bol et al., *Ann. Rev. Phytophathol*, 28:13–138, 1990.
Bowles, *Ann. Rev. Biochem*, 59:873–907, 1990.
Braun and Hemenway, *Seeds*, 4(6):735–744, 1992.
Broekaert et al., *Critical Reviews in Plant Sciences*, 16(3):297–323, 1997.
Bustos et al., *EMBO J.*, 10:1469–1479, 1991.
Castresana et al., *EMBO J.*, 7:1929–1936, 1988.
Capecchi, *Cell*, 22(2):479–488, 1980.
Cashmore et al., *Gen. Eng. of Plants*, Plenum Press, New York, 29–38, 1983.
Cerda-Olmedo et al., *J. Mol. Biol.*, 33:705–719, 1968.
Chauetal., *Science*, 244:174–181. 1989.
Christensen et al., *Plant Mol. Biol.*, 18:675,689, 1992.
Christou et al., *Plant Physiol.*, 87:671–674, 1988.
Christou et al., *Bio/Technology*, 9:957, 1991.
Clapp, *Clin. Perinatol.*, 20(1):155–168, 1993.
Costa et al. *Methods Mol. Biol.*, 57:31–44, 1996.
Craik, *BioTechniques*, 3:12–19, 1985.
Craig, *Science*, 260:1902–1903, 1993.
Curiel et al., *Hum. Gen. Ther.*, 3(2):147–154, 1992.
Davey et al., *Symp. Soc. Exp. Biol.*, 40:85–120, 1986.
Davey et al., *Plant Mol. Biol.*, 13(3):273–285, 1989.
De Kathen and Jacobsen, *Seeds Rep.*, 9(5):276–9, 1990.
Dellaporta et al., *Stadler Symposium*, 11:263–282, 1988.
De la Pena et al., *Nature*, 325:274, 1987.
Demolder et al., *J. Biotechnology*, 32:179–189, 1994.
Deng and Nickloff, *Anal. Biochem.*, 200:81, 1992.
Doyle et al., *J. Biol. Chem.*, 261:9228–9238, 1986.
Eglitis and Anderson, *Biotechniques*, 6(7):608–614, 1988.
Ellis et al., *Proc. Natl. Acad. Sci. U.S.A.*, 92:4185, 1995.
Enderlin and Ogrydziak, *Yeast*, 10:67–79, 1994.
Feinbaum et al., *Mol. Gen. Genet.*, 226:449–456, 1991.
Fiedler et al., *Plant Molecular Biology*, 22:669–679, 1993.
Fitchen and Beachy, *Ann. Rev. Microbiol.*, 47:739–763, 1993.
Fraley et al., *Proc. Natl. Acad. Sci. U.S.A.*, 80:4803, 1983.
Frits Eckstein et al., *Nucleic Acids Research*, 10:6487–6497, 1982.
Fromm et al., *Proc. Natl. Acad. Sci. USA*, 82(17):5824–5828, 1985.
Fromm et al., *Bio/Technology*, 8:833, 1990.
Fuller et al., *Proc. Natl. Acad. Sci. (U.S.A.)*, 86:1434–1438, 1989.
Fynan et al., *Proc. Natl. Acad. Sci. USA*, 90(24):11478–11482, 1993.
Gasser and Fraley, *Science*, 244:1293, 1989.
Gething and Sambrook, *Nature*, 355:33–45, 1992.
Glick et al., *Methods in Plant Molecular Biology and Biotechnology*, CRC Press, Boca Raton, Fla., 1993.
Goossens et al., *Eur. J. Biochem.*, 225:787–95, 1994.
Goossens et al., *Plant Physiol.*, 120:1095–1104, 1999.
Gordon-Kamm et al., *Seeds*, 2:603, 1990.
Graham and Van der Eb, *Virology*, 54(2):536–539, 1973.
Grant et al., *Seeds Rep.*, 15(3/4):254–258 1995.
Grant et al., *Science*, 269:843–846, 1995.
Greener et al., *Mol. Biotechnol.*, 7:189–195, 1997.
Guerola et al., *Nature New Biol.*, 230:122–125, 1971.
Harlow and Lane, In: *Antibodies: A Laboratory Manual*, Cold Spring Harbor Press, Cold Spring Harbor, N.Y., 1988.
Hartl et al., *TIBS*, 19:20–25, 1994.
Hershey and Stoner, *Plant Mol. Biol.*, 17:679–690, 1991.
Hess, *Intern Rev. Cytol.*, 107:367, 1987.
Hinchee et al., *Bio/Technology*, 6:915–922, 1988.
Hinnen et al., *Proc. Natl. Acad. Sci. (U.S.A.)*, 75:1920, 1978.
Horsch et al., *Science*, 227:1229–1231, 1985.
Ikatu et al., *Bio/Technol.*, 8:241–242, 1990.
Ito et al., *J. Bacteriology*, 153:163, 1983.
Jarai and Buxton, *Current Genetics*, 26:2238–2244, 1994.
Jefferson (I), *Plant Mol. Biol, Rep.*, 5:387–405, 1987.
Jefferson (II) et al., *EMBO J.*, 6:3901–3907, 1987.
Johnston and Tang, *Methods Cell Biol.*, 43(A):353–365, 1994.
Jones et al., *Science*, 266:789–793, 1994.
Julius et al., *Cell*, 32:839–852, 1983.
Julius et al., *Cell*, 37:1075-10–89, 1984.
Kares et al., *Plant Mol. Biol.*, 15:905, 1990.
Katz et al., *J. Gen. Microbiol.*, 129:2703–2714, 1983.
Kawasaki, In: PCR™ Protocols, *A Guide to Methods and Applications*, Innis et al., Eds., Academic Press, San Diego, 21–27, 1990.
Kay et al., *Science*, 236:1299, 1987.
Keller et al., *EMBO L.*, 8:1309–1314, 1989.
Knutzon et al., *Proc. Natl. Acad. Sci U.S.A.*, 89:2624–2628, 1992.
Koziel et al., *Bio/Technology*, 11:194, 1993.
Kridl et al., *Seed Sci. Res.*, 1:209, 1991.
Kuby, *Immunology*, 2d Edition. W.H. Freeman and Company, New York, 1994.
Kudla et al., *EMBO*, 9:1355–1364, 1990.
Kuhlemeier et al., *Seeds*, 1:471, 1989.
Kunkel, *Proc. Natl. Acad. Sci. U.S.A.*, 82:488–492, 1985.
Kyte and Doolittle, *J. Mol. Biol.*, 157:105–132, 1982.
Lam and Chua, *J. Biol. Chem.*, 266:17131–17135, 1990.
Lam and Chua, *Science*, 248:471, 1991.
Laemmli, *Nature*, 227:680–685, 1970.
Lioi and Bollini, *Bean Improvement Cooperative*, 32:28, 1989.
Lipman and Pearson, *Science*, 227:1435–1441, 1985.
Lindstrom et al., *Developmental Genetics*, 11:160, 1990.
Linthorst, *Crit. Rev. Plant Sci.*, 10:123–150, 1991.

Logemann et al., *Seeds*, 1:151–158, 1989.
Lu et al., *J. Exp. Med.,* 178(6):2089–2096, 1993.
Luo et al., *Plant Mol Biol. Reporter,* 6:165, 1988.
MacKenzie et al., *Journal of Gen. Microbiol.,* 139:2295–2307, 1993.
Mahadevan, et al., *J. Animal Sci.* 50:723–728, 1980.
Malardier et al., *Gene,* 78:147–156, 1989.
Maloy et al., *Microbial Genetics* 2nd Edition, Jones and Barlett Publishers, Boston, Mass., 1994.
Mandel et al., *Plant Mol. Biol,* 29:995–1004, 1995.
Marraccini et al., *Plant Physiol. Biochem.* (Paris), 37(4):273–282, 1999.
McCabe et al., *Biotechnolgy,* 6:923, 1988.
McElroy et al., *Seeds,* 2:163–171, 1990.
Needleman and Wunsch, *Journal of Molecular Biology,* 48:443–453, 1970.
Neuhaus et al., *Theor. Appl. Genet.,* 75:30, 1987.
Odell et al., *Nature,* 313:810, 1985.
Osborn et al., *Theor. Appl. Genet.,* 71:847–55, 1986.
Osuna et al., *Critical Reviews In Microbiology,* 20:107–116, 1994.
Ou-Lee et al., *Proc. Natl. Acad. Sci U.S.A.,* 83:6815, 1986.
Ow et al., *Science,* 234:856–859, 1986.
Pearson and Lipman, *Proc. Natl. Acad. Sci. (U.S.A.),* 85:2444–2448, 1988.
Pearson, "Rapid and Sensitive Sequence Comparison with FASTP and FASTA." *Methods in Enzymology,* (R. Doolittle, ed.), 183, 63–98, Academic Press, San Diego, Calif., USA, 1990.
Pearson, *Protein Science,* 4:1145–1160, 1995.
Pena et al., *Nature,* 325:274, 1987.
Perlak et al., *Bio/Technology,* 8:939–943, 1990.
Perlak et al., *Plant Molecular Biology,* 22:313–321, 1993.
Pesole et al., *BioTechniques,* 25:112–123, 1998.
Poszkowski et al., *EMBO J.,* 3:2719, 1989.
Potrykus et al., *Ann. Rev. Plant Physiol. Plant Mol. Biol.,* 42:205, 1991.
Potrykus et al., *Mol. Gen. Genet.* 199:183–188, 1985.
Puig and Gilbert, *J. Biol. Chem.,* 269:7764–7771, 1994.
Pyee et al., *Plant J.,* 7:49–59, 1995.
Rhodes et al., *Science,* 240:204, 1988.
Richins et al., *Nucleic Acids Res.,* 20:8451, 1987.
Robinson et al., *Bio/Technology,* 1:381–384, 1994.
Rodriguez et al., *Vectors: A Survey of Molecular Cloning Vectors and Their Uses,* Butterworths, Boston, 1988.
Rogan and Bessman, *J. Bacteriol.,* 103:622–633, 1970.
Rogers et al., *Meth. In Enzymol,* 153:253–277, 1987.
Samac et al., *Seeds,* 3:1063–1072, 1991.
Sambrook et al., *Molecular Cloning: A Laboratory Manual,* Second Edition, Cold Spring Harbor Laboratory Press, Cold Spring Harbor, N.Y., 1989.
Schroeder et al., *Plant J.,* 2:161–172, 1992.
Schroeder et al., *Plant Physiol.,* 101 (3):751–757, 1993.
Schulze-Lefert et al., *EMBO J.,* 8:651, 1989.
Sequence Analysis Software Package Manual (Version 1.0; Genetics Computer Group, Inc., University of Wisconsin Biotechnology Center, Madison, Wis.)
Simpson, *Science,* 233:34, 1986.
Singer and Kusmierek, *Ann. Rev. Biochem.,* 52:655–693, 1982.
Slighton and Beachy, *Planta,* 172:356, 1987.
Smith, et al, In: *Genetic Engineering: Principles and Methods,* Setlow et al., Eds., Plenum Press, NY, 1–32, 1981.
Smith and Waterman, *Advances in Applied Mathematics,* 2:482–489, 1981.
Smith et al., *Nucleic Acids Research,* 11:2205–2220, 1983.
Somers et al., *Bio/Technology,* 10:1589, 1992.
Stalker et al., *J. Biol. Chem.,* 263:6310–6314, 1988.
Sutcliffe et al., *Proc. Natl. Acad. Sci. (U.S.A.),* 75:3737–3741, 1978.
Thillet et al., *J. Biol. Chem.,* 263:12500–12508, 1988.
Vandeyar et al. *Gene,* 65:129–133, 1988
Van Tunen et al., *EMBO J.,* 7:1257, 1988.
Vasil, *Biotechnology,* 6:397, 1988.
Vasil et al., *Bio/Technology,* 10:667, 1992.
Verdier, *Yeast,* 6:271–297, 1990.
Vodkin et al., *Cell,* 34:1023, 1983.
Vogel et al., *J. Cell Biochem., (Suppl)* 13D:312, 1989.
Wagner et al., *Proc. Natl. Acad. Sci. USA,* 89(13):6099–6103, 1992.
Wallace et al., *British J. Nutrition,* 50:345–355, 1983.
Wang and Tsou, *FASEB Journal,* 7:1515–1517, 1993.
Watkins, *Handbook of Insecticide Dust Diluents and Carriers,* Second Edition, Darland Books, Caldwell, N.J.
Weissbach and Weissbach, *Methods for Plant Molecular Biology,* (Eds.), Academic Press, Inc., San Diego, Calif., 1988.
Weisshaar et al, *EMBO J.,* 10:1777–1786, 1991.
Wenzler et al., *Plant Mol. Biol.,* 12:41–50, 1989.
Whitham et al., *Cell,* 78:1101–1115, 1994.
Williams, et al, *Biotechnology,* 10:540–543, 1992.
Winnacker-Kuchler, *Chemical Technology,* 4th Ed., Vol. 7, Hanser Verlag, Munich, 1986.
Wolf et al., *Compu. Appl. Biosci,* 4(1):187–91, 1988.
Wong and Neumann, *Biochim. Biophys. Res. Commun.,* 107(2):584–587, 1982.
Wu et al., *Seeds,* 7(9):1357–1368, 1995.
Yang et al., *Proc. Natl. Acad. Sci. USA,* 87:4144–48, 1990.
Yamaguchi-Shinozaki et al., *Plant Mol. Biol.,* 15:905, 1990.
Yelton et al., *Proc. Natl. Acad. Sci. (U.S.A.),* 81:1470–1474, 1984.
Zatloukal et al., *Ann. N.Y. Acad. Sci.,* 660:136–153, 1992.
Zhang and Wu, *Theor. Appl. Genet.,* 76:835, 1988.
Zhou et al., *Methods in Enzymology,* 101:433, 1983.
Zukowsky et al., *Proc. Natl. Acad. Sci. (U.S.A.),* 80:1101–1105, 1983.
U.S. Pat. Nos. 3,959,493; 4,533,557; 4,554,101; 4,683,195; 4,683,202; 4,713,245; 4,757,011; 4,769,061; 4,826,694; 4,940,835; 4,957,748; 4,971,908; 5,100,679; 5,219,596; 5,384,253; 5,689,052; 5,936,069; 6,005,076; 6,146,669 and 6,156,227.
EP Application Nos. 0 154 204; 0 218 571; 0 238 023; 0 255 378 and 0 385 962.

What is claimed is:

1. A modified polypeptide comprising a substitution of 1 or more essential amino acids selected from the group consisting of isoleucine and tryptophan into an unmodified polypeptide with the amino acid sequence of SEQ ID NO: 1; wherein said tryptophan is substituted into said unmodified polypeptide in place of at least one amino acid selected from the group consisting of N32, Y35, N40, N50, Y72, H88, Y116, H119, Y132, Y133, P137, Y158, Y172, E200, P239, Y249, P265, P324, Y330, Y346, N368, and Y411; and wherein said isoleucine is substituted into said unmodified polypeptide in place of at least one amino acid selected from the group consisting of N32, L36, F46, G51, L56, F59, Q65, L66, Y72, R73, V75, Q76, L85, H88, F94, L95, L96, F97, V98, L99, R102, L105, L107, N117, L118, D122, Q124, R125, P 127, Y132, Y133, L134, V135, P137, L143, K147, L148, P151, Y158, F162, Q169, L173, L181, V209, P239, F240, P247, F256, E258, N264, P265, L267, F273, L274, L285, L286, H288, N290, V295, L297, V298, N300, L308, V309, K317, K319, P324, L334, V339, F340, V341, Y346, F348, V350, L356, F358, L359, F361, N368, F372, F393, Y411, F412, and V413, wherein said modified polypeptide accumulates in a seed.

2. The modified polypeptide of claim 1, wherein 2 or more of said essential amino acids are added.

3. The modified polypeptide of claim 1, wherein said modified polypeptide comprises greater than a 0.25% (weight per weight) increase of said essential amino acids, relative to said unmodified polypeptide.

4. A modified polypeptide comprising a substitution of 1 or more essential amino acids selected from the group consisting of threonine, lysine, and methionine, into an unmodified polypeptide with the amino acid sequence of SEQ ID NO: 2; wherein said threonine is substituted into said unmodified polypeptide in place of at least one amino acid selected from the group consisting of S54, S225, S250, S251, S75, S90, S202, S16, S38, S139, S197, S385, A65, A67, A78, A98, A124, A258, A279, A307, A327, A335, A268, A340, A367, V83, V284, V324, V186, V375, L171, L348, N275, N326, N346, N92, N216, N280, N332, N35, N168, Q53, Q303, Q32, R304, K201, K230, E276, E282, D68, D135, D89, D253, D389, D313, F136, P262, P62, P222, P318, and P240; wherein said lysine is substituted into said unmodified [β-conglycinin] polypeptide in place of at least one amino acid selected from the group consisting of R169, R194, R243, R361, R377, R37, R357, R304, R45, R132, R179, R199, R205, R383, S75, S202, S13, S210, S329, S371, T328, N84, N117, N339, Q192, Q149, Q241, Q116, Q142, Q145, H153, V363, L379, L300, I155, I208, I223, I286, D89, E157, E166, E191, E365, and E376: and wherein said methionine is substituted into said unmodified [β-conglycinin] polypeptide in place of at least one amino acid selected from the group consisting of L41, L156, L242, L245, L188, L379, I167, I193, I208, F34, Y386, N239, Q364, and Q241, wherein said modified polypeptide accumulates in a seed.

* * * * *